United States Patent [19]

Otto

[11] Patent Number: 5,616,578
[45] Date of Patent: Apr. 1, 1997

[54] METHOD OF TREATING HUMAN IMMUNODEFICIENCY VIRUS INFECTION USING A CYCLIC PROTEASE INHIBITOR IN COMBINATION WITH A REVERSE TRANSCRIPTASE INHIBITOR

[75] Inventor: Michael J. Otto, West Chester, Pa.

[73] Assignee: The Dupont Merck Pharmaceutical Company, Wilmington, Del.

[21] Appl. No.: 110,603

[22] Filed: Aug. 26, 1993

[51] Int. Cl.$^6$ .......................... A61K 31/55; A61K 31/51; A61K 31/52; A61K 31/505
[52] U.S. Cl. .......................... 514/218; 514/264; 514/274
[58] Field of Search .......................... 514/218, 264, 514/274; 540/492

[56] References Cited

U.S. PATENT DOCUMENTS 4,835,177  5/1989  Durette .................................. 514/459

FOREIGN PATENT DOCUMENTS

| 443848 | 8/1991 | European Pat. Off. . |
| 9221647 | 12/1992 | WIPO . |
| 9307128 | 4/1993 | WIPO . |

OTHER PUBLICATIONS

Moore et al., Biochem, Biophys, Res. Comm., 159: pp. 420–425 (1989).
Dreyer et al., Proc. Nathl. Acad. Sci. USA, 86: 9752–9756 (1989).
Vacca et al., J. Med. Chem. 34: 1225–1228 (1991).
Roberts et al., Science 248: 358–361 (1990).
Grobelny et al., Biochem. Biophys. res. Commun. 169: 1111–1116 (1990).
Sham et al., Biochem. Biophys. res. Commun. 175: 914–916 (1991).
Pauwels et al., Nature 343: 470–474 (1990).
Merluzzi et al., Science 250: 1411–1413 (1990).
Goldman et al., Proc. Natl. Acad. Sci. (USA) 88: 6863–6867 (1991).
Chou and Talalay, Adv. Enzyme Regul. 22: 27–55 (1984).
Kempf et al., J. Med. Chem., 33: 2687–2689 (1990).
Mitsuya and Broder, Nature, 325: 773–778 (1987).
Mansuri et al., J. Med chem. 32: 461 (1989).
McQuade et al., Science 247: 454–456 (1990).
Schinazi et al., Antimicrob. Agents Chemother., 30: 491–498 (1986).
Kashman et al., J. Med. Chem, vol. 35, No. 15, Jul. 24, 1992, pp. 2735–2743.
Dagani, Chemical & Engineering News, vol. 65, No. 47, Nov. 23, 1987, pp. 41–49.
Lang, Arch. Pharm., 326(9), p. 574, (1993).

*Primary Examiner*—Richard L. Raymond
*Assistant Examiner*—Mary C. Cebulak
*Attorney, Agent, or Firm*—Blair Q. Ferguson; David H. Vance

[57] ABSTRACT

This invention relates to a method of treating human immunodeficiency virus (HIV) infection in a mammal comprising administering to the mammal a therapeutically effective amount of a combination of: (i) at least one cyclic HIV protease inhibitor and (ii) at least one HIV reverse transcriptase inhibitor.

26 Claims, 2 Drawing Sheets

METHOD OF TREATING HUMAN IMMUNODEFICIENCY VIRUS INFECTION USING A CYCLIC PROTEASE INHIBITOR IN COMBINATION WITH A REVERSE TRANSCRIPTASE INHIBITOR

FIELD OF THE INVENTION

This invention relates to a method of treating human immunodeficiency virus (HIV) infection in a mammal comprising administering to the mammal a therapeutically effective amount of a combination of: (i) at least one cyclic HIV protease inhibitor and (ii) at least one HIV reverse transcriptase inhibitor.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

AIDS is characaterized by a progressive depletion of T lymphocytes, particularly the helper-inducer subset having a CD4 surface antigen (CD4$^+$). CD4$^+$ lymphocytes are responsible for the induction of numerous functions of the human immune system.

No treatment is currently available to prevent or reverse the immunodeficiency of AIDS and ARC. Moreover, it is generally believed that an effective vaccine or therapy must be developed in order to prevent the transmission of HIV.

A number of compounds that interfere with viral replication have been developed to treat AIDS, including inhibitors of HIV reverse transcriptase (RT), such as nucleoside analogs including 3'-azido-3'-deoxythymidine (AZT, zidovidine) and 2', 3'-dideoxy nucleosides such as 2', 3'-dideoxyinosine (DDI, ddI) and 2', 3'-dideoxycytidine (DDC, ddC).

To date only AZT has been approved by the U.S. FDA for early treatment of HIV positive individuals as well as individuals with ARC and AIDS. However, AZT is frequently toxic, causing bone marrow suppression resulting in anemia, leukopenia and thrombocytopenia. Also, AZT-resistant HIV strains have been observed after six months of AZT treatment. DDI and DDC have been FDA approved for treatment of individuals with ARC and AIDS only in combination with AZT.

Consequently, there is a continuing need for new effective and safe treatments for HIV infection and the associated HIV disease, including AIDS.

The aspartic acid protease encoded by HIV is critical for replication of the virus (Kohl, et al., Proc. Natl. Acad. Sci. 85:4686–4690 (1988)). HIV protease is responsible for specific cleavages of the viral gag/pol gene products, which are precursors of essential viral structural proteins and essential enzymes including reverse transcriptase, integrase, and the protease itself (Ratner et al., Nature 316:277–284 (1985); Schneider and Kent, Cell 54:363–368 (1988); Darke et al., Biochem. Biophys. Res. Commun. 156: 297–303 (1988)). Inhibition of HIV protease by synthetic inhibitors during infection of cells in cell culture leads to a reduction in the amount of infectious virus particles produced (McQuade et al., Science 247: 454– 456 (1990)). This inhibition of HIV by HIV protease inhibitors is presumably due primarily to the insufficient processing of the p55 gag polyprotein to the essential structural gag proteins p24, p17, p7 and p6.

To date, most inhibitors of the HIV aspartic acid protease have been transition state mimetics. These have included reduced amides (Moore et al., Biochem. Biophys. Res. Commun. 159:420–425 (1989); Dreyer et al., Proc. Natl. Acad. Sci. 86:9752–9756 (1989)), hydroxyethylene isosteres (Dreyer et al., Proc. Natl. Acad. Sci. 86:9752–9756 (1989); Vacca et al., J. Med. Chem. 34:1225–1228 (1991); Tomasselli et al., J. Biol. Chem. 265: 14675–14683 (1990); Roberts et al., Science 248:358–361 (1990)), statine analogs (Dreyer et al., 1989), phosphinic acid derivatives (Grobelny et al., Biochem. Biophys. Res. Commun. 169:1111–1116 (1990)) and difluoroketone derivatives (Dreyer et al., 1989; Sham et al., Biochem. Biophys. Res. Commun. 175: 914–916 (1991)).

HIV reverse transcriptase (RT) inhibitors can be grouped into two classes of compounds, nucleoside analogs and non-nucleoside RT inhibitors. Inhibition by either type of compounds results in the inhibition of virus replication in infected cells. Several nucleoside analogs, AZT, ddI, ddC, d4T and 3TC are currently in clinical trials or are approved for the treatment of HIV disease. These compounds act as competitive substrate inhibitors for the HIV RT following phosphorylation by cellular enzymes. Currently, no non-nucleoside RT inhibitors are approved but several, including TIBO (Pauwels et al., Nature 343:470–474 (1990)), nevirapine (Merluzzi et al., Science 250:1411–1413 (1990)), and L-697,661 (Goldman et al., Proc. Nat. Acad. Sci. (USA) 88: 6863–6867 (1991)) are being clinically evaluated. These compounds are non-competitive allosteric inhibitors or HIV RT.

SUMMARY OF THE INVENTION

The present invention provides a method of treating human immunodeficiency virus (HIV) infection in a mammal comprising administering to the mammal a therapeutically effective amount of a combination of: (i) at least one cyclic HIV protease inhibitor, said cyclic HIV protease inhibitor being a compound of Formula I (shown below), and (ii) at least one HIV reverse transcriptase inhibitor.

In the present invention, it has been discovered that the administration of a cyclic HIV protease inhibitor of Formula I (component (i)) in combination with an HIV reverse transciptase inhibitor (component (ii)) resulted in an unexpected synergistic effect in inhibiting the replication of HIV. Thus, the HIV inhibitory effects of the cyclic HIV protease inhibitor administered in combination with the RT inhibitor was greater than the additive effect of each agent when administered alone. Remarkably, the undesirable cytotoxic effect of the cyclic HIV protease inhibitor administered in combination with the RT inhibitor was less than the additive cytotoxic effect of each agent when administered alone.

BRIEF DESCRIPTION OF THE DRAWINGS

FIG. 1 shows a plot of the combination index value for the inhibition of HIV (RF strain in MT-2 human T-cells) replication for dosage combinations of a representative of a representative cyclic HIV protease inhibitor (Ex. No. 5U) and a representative HIV RT inhibitor (AZT).

DETAILED DESCRIPTION OF THE INVENTION

Figure 2B:
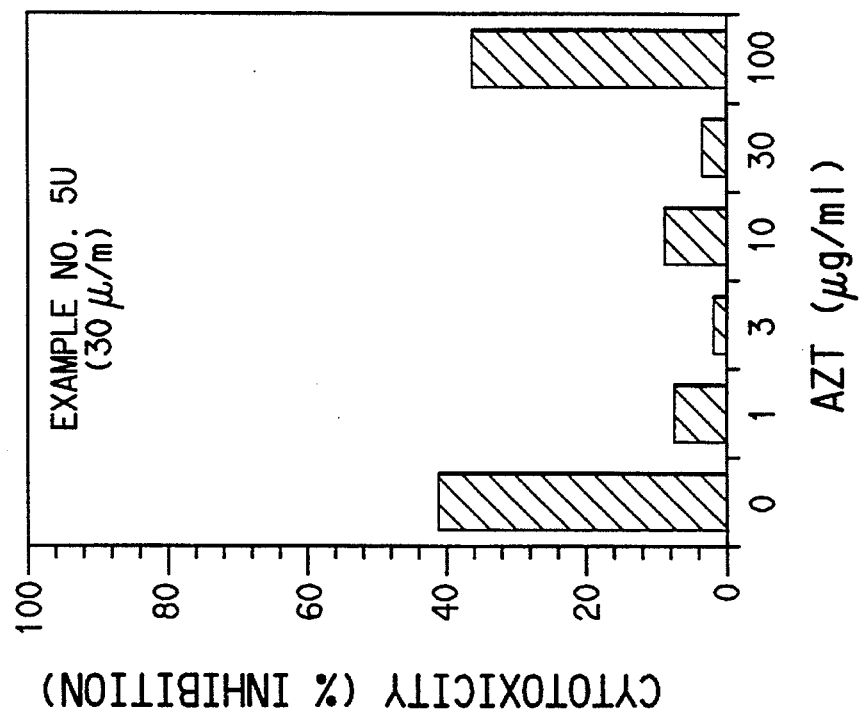
FIGS. 2A and 2B show the cytotoxicity effects on MT-2 human T-cells of dosage combinations of a representative cyclic HIV protease inhibitor (Ex. No. 5U) and a representative HIV RT inhibitor (AZT).

The present invention provides a method of treating human immunodeficiency virus (HIV) infection in a mammal comprising administering in combination to the mammal a therapeutically effective amount of: (i) at least one cyclic HIV protease inhibitor, said cyclic HIV protease inhibitor being a compound of Formula I (shown below) and (ii) at least one HIV reverse transcriptase inhibitor.

In the present invention, it has been discovered that the administration of a cyclic HIV protease inhibitor of Formula I (component (i)) in combination with an HIV reverse transciptase inhibitor (component (ii)) resulted in an unexpected synergistic effect in inhibiting the replication of HIV. Thus, the HIV inhibitory effects of the cyclic HIV protease inhibitor administered in combination with the RT inhibitor was greater than the additive effect of each agent when administered alone. Moreover, remarkably the undesirable cytotoxic effect of the cyclic HIV protease inhibitor administered in combination with the RT inhibitor was less than the additive cytotoxic effect of each agent when administered alone.

Thus, it has been discovered that the cyclic HIV protease inhibitor of the present invention can be administered in combination with an HIV RT inhibitor, thereby to reduce the doses of each drug required to achieve the effective inhibition of HIV replication. Moreover, it has been discovered that the use of the compounds of component (i) and component (ii) of the invention in combination results in a greater than additive anti-HIV effect, coupled with a less than additive adverse cytotoxic effect. Thus, the combination treatment of the present invention permits the use of lower doses of each component; with reduced adverse, toxic effects of each component. A lower dosage minimizes the potential of side effects of the compounds, thereby providing an increased margin of safety relative to the margin of safety for each component when used as a single agent.

As used herein, the term "cyclic HIV protease inhibitor" refers to a compound of Formula (I) described below. The cyclic HIV protease inhibitor compounds of Formula (I) are described in PCT International Patent Application Publication Number WO 93/07128, published Apr. 15, 1993 and in copending, commonly assigned U.S. patent application U.S. Ser. No. 08/047,330.

By "therapeutically effective amount" it is meant an amount of component (i) and component (ii) that when administered alone or in combination to a cell or mammal is effective to inhibit the replication of HIV.

By "administered in combination" or "combination" when refering to component (i) and component (ii) of the present invention, it is meant that the components are administered concurrently to the cell or mammal being treated. When administered in combination each component may be administered at the same time or sequentially in any order at different points in time. Thus, component (i) and component (ii) may be administered separately but sufficiently closely in time so as to provide the desired HIV inhibitory effect.

This invention also includes pharmaceutical kits comprising or consisting essentially of a pharmaceutical composition comprising the cyclic HIV protease inhibitor compounds of Formula I together with a pharmaceutical composition comprising an HIV RT inhibitor, and to methods of using such pharmaceutical kits for the inhibition of HIV and treatment of HIV infection.

This invention also includes combination products comprising pharmaceutical compositions comprising a cyclic HIV protease inhibitor compounds of Formula I in physical combination or in a single dosage unit with an HIV RT inhibitor, to pharmaceutical kits containing these combination products, and to methods of using these combination products for the inhibition of HIV and treatment of HIV infection.

In the method of the present invention, the cyclic HIV protease inhibitor compounds of Formula I is administered in combination with an HIV RT inhibitor to achieve a synergistic anti-HIV effect. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds.

The method of the present invention provides for an enhanced antiviral effect of the two drugs when administered in combination without the expected concomitant increase in the adverse undesired toxic effects. Thus, the claimed combination treatment allows for the use of lowered clinical doses with reduced side effects. In view of the toxicity associated with the presently approved therapies for HIV, such as AZT, the present invention provides an important advantage over current therapies for HIV.

Reverse transcriptase (RT) inhibitors useful in the method, combination products, and pharmaceutical kits of the present invention include, but are not limited to, AZT, ddI, ddC, d4T and 3TC, and non-nucleoside reverse transcriptase inhibitors including, but not limited to: TIBO derivatives; BI-RG-587 and derivatives thereof; nevirapine; L-697,661 and derivatives thereof; LY 73497; and Ro 18,893 (Roche).

As disclosed in PCT International Patent Application Publication Number WO 93/07128, published Apr. 15, 1993 and in copending, commonly assigned U.S. patent application U.S. Ser. No. 08/047,330, compounds of the cyclic protease inhibitors of Formula I represents a new class of HIV protease inhibitors which are useful for the treatment of HIV infection. These cyclic HIV protease inhibitors lack the amide bonds found in previous inhibitors, but retain the symmetry of the potent C-2 symmetrical diols.

In the present invention it has been found that therapeutic agents component (i) and component (ii) when administered in combination exert a synergistic antiviral effect without a corresponding increase in toxicity. These results indicate that such combination treatment might allow the use of lowered clinical doses with reduced side effects.

[1] The cyclic HIV protease inhibitors of component (ii) useful in this invention include cyclic compounds of the Formula (I):

or a pharmaceutically acceptable salt thereof, wherein:

$R^4$ and $R^7$ are independently selected from the following groups:
hydrogen;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or $R^{12}$;

a 5- to 10-membered heterocyclic ring system containing 1 to 4 heteroatoms independently selected from oxygen, nitrogen or sulfur, said heterocyclic ring system being substituted with 0–2 $R^{12}$;
—$OR^{13}$; —$SR^{13}$; $CO_2R^{13}$;

$R^{4A}$ and $R^{7A}$ are independently selected from the following groups:
hydrogen;
$C_1$–$C_4$ alkyl substituted with halogen or $C_1$–$C_2$ alkoxy;
benzyl substituted with halogen or $C_1$–$C_2$ alkoxy;
—$OR^{13}$; —$SR^{13}$; $CO_2R^{13}$;

$R^4$ and $R^{4A}$ can alternatively join to form a 5–7 membered carbocyclic ring substituted with 0–2 $R^{12}$;

$R^7$ and $R^{7A}$ can alternatively join to form a 5–7 membered carbocyclic ring substituted with 0–2 $R^{12}$;

n is 0, 1, or 2;

$R^5$ is selected from H; halogen; $C_1$–$C_6$ alkyl substituted with 0–3 $R^{11}$; —$N(R^{20})_2$; —$SR^{20}$; or —$OR^{20}$;

$R^6$ is independently selected from: hydrogen, halogen, $C_1$–$C_6$ alkyl substituted with 0–3 $R^{11}$, —$N(R^{20})_2$, —$SR^{20}$, or —$OR^{21}$;

$R^5$ and $R^6$ can alternatively join to form an epoxide or aziridine ring; —$OCH_2SCH_2O$—; —$OS(=O)O$—; —$OC(=O)O$—; —$OCH_2O$—; —$OC(=S)O$—; —$OC(=O)C(=O)O$—; —$OC(CH_3)_2O$—; —$OC((CH_2)_3NH_2)(CH_3)O$—; —$OC(OCH_3)(CH_2CH_2CH_3)O$—; —$OS(=O)O$—; —$NHC(=O)NH$—; —$OC(=O)NH$—; —$NHC(=O)O$—; —$NHCH_2O$—; —$OCH_2NH$—; —$NHC(=S)O$—; —$OS(=O)NH$—; —$NHC(=O)C(=O)O$—; —$OC(=O)C(=O)NH$—; —$NHC(=O)C(=O)NH$—; —$OC(CH_3)_2O$—; —$NHC(CH_3)_2O$—; —$OC(CH_3)_2NH$— or any group that, when administered to a mammalian subject, cleaves to form a free dihydroxyl or diamino or hydroxyl and amino;

$R^{5a}$ is selected from hydrogen, halogen, $C_1$–$C_6$ alkyl, —$N(R^{20})_2$, —$SR^{20}$ or —$OR^{20}$;

$R^{6a}$ is selected from: hydrogen, halogen, $C_1$–$C_6$ alkyl, —$N(R^{20})_2$, $SR^{20}$ or —$OR^{21}$;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
$C_1$–$C_6$ alkylaminocarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$; or
any group that, when administered to a mammalian subject, cleaves to form a free hydroxyl, amino or sulfhydryl;

$R^{11}$ is selected from one or more of the following:
H, keto, halogen, cyano, —$CH_2NR^{13}R^{14}$, —$NR^{13}R14$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;

1–3 amino acids linked together via amide bonds, and linked to $R^4$, $R^7$, $R^{20}$, or $R^{21}$ via the amine or carboxylate terminus;

—($C_1$–$C_3$ alkyl)aryl substituted with 0–2 $R^{12}$;

a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:
H, keto, halogen, cyano, —$CH_2NH_2$, —$NH_2$, —$CO_2H$, —$OC(=O)(C_1$–$C_3$ alkyl), —OH, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ aklylcarbonylamino, —$OCH_2CO_2H$, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system;

$R^{12}$ when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy, —$C(R^{14})=N(OR^{14})$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6-membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{12}$ is attached to a saturated carbon atom, it may be =O or =S;

$R^{12}$ when a substituent on nitrogen, is selected from one or more of the following:

phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})$=$N(OR^{14})$;

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_1$–$C_6$ alkylcarbonyl substituted with 0–3 $R^{11A}$;
$C_1$–$C_6$ alkoxycarbonyl substituted with 0–3 $R^{11A}$;
$C_1$–$C_6$ alkylaminocarbonyl substituted with 0–3 $R^{11A}$;
$C_3$–$C_6$ alkoxyalkyl substituted with 0–3 $R^{11A}$;
an amine protecting group when $R^{13}$ is bonded to N;
a hydroxy protecting group when $R^{13}$ is bonded to O;

$R^{14}$ is OH; H; $CF_3$; $C_1$–$C_6$ alkyl substituted with 0–3 groups selected from OH, $C_1$–$C_4$ alkoxy, halogen, $NH_2$; $C_1$–$C_6$ alkoxy; $NH_2$; $C_2$–$C_6$ alkenyl; benzyl; an amine protecting group when $R^{14}$ is bonded to N; a hydroxy protecting group when $R^{14}$ is bonded to O;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

W is selected from:
—$N(R^{22})C(=Z)N(R^{23})$—;
—$OC(=Z)O$—;
—$N(R^{22})C(=Z)O$—;
—$C(R^{25})(R^{26})C(=Z)C(R^{27})(R^{28})$—;
—$N(R^{22})C(=Z)C(R^{27})(R^{28})$—;
—$C(R^{25})(R^{26})C(=Z)O$—;
—$N(R^{22})C(=Z)C(=Z)N(R^{23})$—;
—$C(R^{25})(R^{26})C(F_2)C(R^{27})(R^{28})$—;
—$C(R^{25})(R^{26})N(CH_3)(O)C(R^{27})(R^{28})$—;
—$C(R^{25})(R^{26})N(OR^{29})C(R^{27})(R^{28})$—;
—$C(R^{25})(R^{26})C(=Z)S$—;
—$N(R^{22})S(=Z')N(R^{23})$—;
—$N(R^{22})S(=Z')_2N(R^{23})$—;
—$N(R^{22})P(=O)(R^{24a})N(R^{23})$—;
—$C(R^{25})(R^{26})S(=Z')C(R^{27})(R^{28})$—;
—$C(R^{25})(R^{26})S(=Z')_2C(R^{27})(R^{28})$—;
—$C(R^{25})(R^{26})P(=O)(R_{24}a)C(R^{27})(R^{28})$—;
—$C(R^{25})(R^{26})S(=Z,)N(R^{23})$—;
—$C(R^{25})(R^{26})S(=Z')_2N(R^{23})$—;
$C(R^{25})(R^{26})S(=O)_2O$—;
—$C(R^{25})(R^{26})P(=O)(R_{24a})N(R^{23})$—;
—$C(R^{25})(R^{26})P(=O)(R^{24a})O$—;
—$C(R^{25})C(F_2)C(=O)N(R^{23})$—;
—$C(R^{25})C(F_2)S(=O)_2N(R^{23})$—;
—$SC(=z)$—;
—$C(R^{25})(R^{26})C(R^{34})(R^{35})C(R^{27})(R^{28})$—;
—$N(R^{22})C(R^{34})(R^{35})N(R^{23})$—;
—$N=C(R^{36})N(R^{23})$—;
—$N^+(R^{22})=C(R^{36})N(R^{23})$—;
—$N(R^{22})P(R^{24a})N(R^{23})$—;
—$C(=z)$—;
—$P(=O)(R^{24a})$—;
—$S(=Z')$—;
—$S(=Z')_2$—;
—$N(R^{22})C(=C(R^{36a})(R^{36b}))N(R^{23})$—
—$N(R^{22})C(=Z)N(R^{23})C(=Z)$— wherein:

Z is O, S, $NR^{24}$;

Z' is O or $NR_{24}$;

$R^{22}$ and $R^{23}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or R32;
a 5- to 10-membered heterocyclic ring system containing 1 to 4 heteroatoms independently selected from oxygen, nitrogen or sulfur, said heterocyclic ring system being substituted with 0–2 $R^{32}$;
—$OR^{22a}$; —$N(R^{22a})(R^{22b})$;

$R^{22a}$ and $R^{22b}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

$R^{24}$ is selected from: hydrogen; hydroxy; amino; $C_1$–$C_4$ alkyl; $C_1$–$C_4$ alkoxy; mono- or di-($C_1$–$C_6$alkyl)amino; cyano; nitro; benzyloxy; —$NHSO_2$aryl, aryl being optionally substituted with ($C_1$–$C_6$)alkyl;

$R^{24a}$ is selected from: hydroxy; amino; $C_1$–$C_4$ alkyl; $C_1$–$C_4$ alkoxy; mono- or di-($C_1$–$C_6$ alkyl)amino; cyano; nitro; benzyloxy; or phenoxy;

$R^{25}$ and $R^{27}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–3 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;
—$OR^{13}$; —$SR^{13}$;

$R^{26}$ and $R^{28}$ are independently selected from:
hydrogen;
halogen;
$C_1$–$C_4$ alkyl substituted with 0–3 halogen or $C_1$–$C_2$ alkoxy;
benzyl substituted with 0–3 halogen or $C_1$–$C_2$ alkoxy;
—$OR^{13}$; —$SR^{13}$;

$R^{29}$ is selected from:
hydrogen;
$C_1$–$C_4$ alkyl substituted with 0–3 halogen or $C_1$–$C_2$ alkoxy;
benzyl substituted with 0–3 halogen or $C_1$—$C_2$ alkoxy;

alternatively, $R^{22}$, $R^{25}$, or $R^{26}$, independently can join with $R^4$ or $R^{4A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$, $R^{27}$, or $R^{28}$, independently, can join with $R^7$ or $R^{7A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$, $R^{25}$, $R^{26}$, $R^{23}$, $R^{27}$, $R^{28}$, $R^{34}$, or $R^{35}$ can join with $R^5$ or $R^6$ to form a 0- to 7-membered bridge to form a carbocyclic or heterocyclic ring, said bridge being substituted with 0–2 $R^{12}$ and said bridge containing 0–3 heteroatoms independently selected from N, S, or O(i.e., a 0-membered bridge is formed when $R^{22}$, $R^{25}$, $R^{26}$, $R^{23}$, $R^{27}$, $R^{28}$ $R^{34}$, or $R^{35}$ are taken together with $R^5$ or $R^6$ to form a direct bond);

alternatively R28 or R23 can join with R7A to form a direct bond;

alternatively R26 or R22 can join with R4A to form a direct bond;

$R^{31}$ is selected from one or more of the following:
  keto, halogen, cyano, $-CH_2NR^{13}R^{14}$, $-NR^{13}R^{14}$, $-CO_2R^{13}$, $-C(=O)R^{11}$, $-OC(=O)R^{13}$, $-OR^{13}$, $C_2-C_6$ alkoxyalkyl, $-S(O)mR^{13}$, $-NHC(=NH)NHR^{13}$, $-C(=NH)NHR^{13}$, $-C(=O)NR^{13}R^{14}$, $-NR^{14}C(=O)R^{13}$, $=NOR^{14}$, $-NR^{14}C(=O)OR^{14}$, $-OC(=O)NR^{13}R^{14}$, $-NR^{13}C(=O)NR^{13}R^{14}$, $-NR^{14}SO_2NR^{13}R^{14}$, $-NR^{14}SO_2R^{13}$, $-SO_2NR^{13}R^{14}$, $C_1-C_4$, alkyl, $C_2-C_4$ alkenyl, $C_3-C_{10}$ cycloalkyl, $C_3-C_6$ cycloalkylmethyl, benzyl, phenethyl, phenoxy, benzyloxy, nitro, $C_7-C_{10}$ arylalkyl, hydroxamic acid, hydrazide, oxime, boronic acid, sulfonamide, formyl, $C_3-C_6$ cycloalkoxy, $C_1-C_4$ alkyl substituted with $-NR^{13}R^{14}$, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, $-OCH_2CO_2R^{13}$, 2-(1-morpholino)ethoxy, azido, $-C(R^{14})=N(OR^{14})$; or 1–3 amino acids, linked together via amide bonds, and linked to $R^{22}$, $R^{23}$, $R^{25}$, or $R^{27}$ via the amine or carboxylate terminus;

a $C_5-C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$ when a substituent on carbon, is selected from one or more of the following:
  phenethyl, phenoxy, $C_3-C_{10}$ cycloalkyl, $C_3-C_6$ cycloalkylmethyl, $C_7-C_{10}$ arylalkyl, hydrazide, oxime, boronic acid, $C_1-C_6$ alkoxyalkyl, methylenedioxy, ethylenedioxy, $C_1-C_4$ alkylcarbonyloxy, $-NHSO_2R^{14}$, benzyloxy, halogen, 2-(1-morpholino)ethoxy, $-CO_2R^{13}$, hydroxamic acid, $-CONR^{13}NR^{13}R^{14}$, cyano, boronic acid, sulfonamide, $-CHO$, $C_3-C_6$ cycloalkoxy, $-NR^{13}R^{14}$, $-C(R^{14})=N(OR^{14})$, $NO_2$, $-OR^{13}$, $-NR^{40}R^{41}$, $-SO_mR^{13}$, $-SO_mNR^{13}R^{14}$, $-C(=O)NR^{13}R^{14}$, $-OC(=O)NR^{13}R^{14}$, $-C(=O)R^{11}$, $-OC(=O)R^{11}$, $-OCO_2R^{13}$, phenyl, $-C(=O)NR^{13}-(C_1-C_4$ alkyl$)-NR^{13}R^{14}$, $-C(=O)NR^{40}R^{41}$, $C_1-C_4$ haloalkyl, $C_1-C_4$ haloalkoxy, $C_2-C_4$ haloalkenyl, $C_1-C_4$ haloalkynyl, or
  $-C(=O)NR^{13}C(R^{11})_2NR^{13}R^{14}$;—
  $C(=O)NR^{13}C(R^{11})_2NR^{13}NR^{14}$;
  $-C(=O)NR^{13}C(R^{11})_2NR^{13}CO_2R^{13}$;
  $-C(=O)NR^{13}-(C_1-C_4$ alkyl$)-NR^{13}CO_2R^{13}$;
  $-C(=O)N(R^{13})-(C_1-C_4$ alkyl$)-R^{11}$; or
  $-C(=O)C(R^{11})_2NR^{13}R^{14}$;
  $-C(=O)C(R^{11})_2NR^{13}NR^{14}$;
  $-C(=O)C(R^{11})_2NR^{13}CO_2R^{13}$;—$C(=O)-(C_1-C_4$ alkyl$)-NR^{13}R^{14}$;
  $-C(=O)-(C_1-C_4$ alkyl$)-NR^{13}CO_2R^{13}$; or $C_1-C_4$ alkoxy substituted with 0–4 groups selected from: $R^{11}$, $C_3-C_6$ cycloalkyl, $-CO_2R^{13}$, $-C(=O)NR^{13}R^{14}$, $-NR^{13}R^{14}$ or OH;

$C_1-C_4$ alkyl substituted with 0–4 groups selected from: $R^{11}$, $=NR^{14}$, $=NNR^{13}C(=O)NR^{13}R^{14}$ or $-NR^{13}R^{14}$;

$C_2-C_4$ alkenyl substituted with 0–4 $R^{11}$;
  $C_2-C_4$ alkynyl substituted with 0–4 $R^{11}$;
  a 5- or 6-membered heterocyclic ring containing from 1 to 4 heteroatoms independently selected from oxygen, nitrogen or sulfur;

or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1-C_4$ alkyl, $C_1-C_4$ alkoxy, hydroxy, or $-NR^{13}R^{14}$; or, when $R^{32}$ is attached to a saturated carbon atom, it may be $=O$ or $=S$;

$R^{32}$, when a substituent on nitrogen, is selected from one or more of the following:
  phenyl, benzyl, phenethyl, hydroxy, $C_1-C_4$ hydroxyalkyl, $C_1-C_4$ alkoxy, $C_1-C_4$ alkyl, $C_3-C_6$ cycloalkyl, $C_3-C_6$ cycloalkylmethyl, $-CH_2NR^{13}R^{14}$, $-NR^{13}R^{14}$, $C_1-C_6$ alkoxyalkyl, $C_1-C_4$ haloalkyl, $C_1-C_4$ alkoxycarbonyl, $-CO_2H$, $C_1-C_4$ alkylcarbonyloxy, $C_1-C_4$ alkylcarbonyl, $-C(R^{14})=N(OR^{14})$;

$R^{34}$ is selected from:
  hydrogen;
  $OR^{13}$;
  $SR^{13}$;
  halogen;
  $N(R^{38})(R^{39})$
  $C_1-C_6$ alkyl substituted with 0–3 $R^{11}$;
  $C_1-C_6$ alkoxy substituted with 0–3 $R^{11}$;
  $C_1-C_6$ thioalkyl substituted with 0–3 $R^{11}$;

$R^{35}$ is selected from:
  hydrogen;
  $OR^{13}$;
  $SR^{13}$;
  halogen;
  $N(R^{38})(R^{39})$
  $C_1-C_6$ alkyl substituted with 0–3 $R^{11}$;
  $C_1-C_6$ alkoxy substituted with 0–3 $R^{11}$;
  $C_1-C_6$ thioalkyl substituted with 0–3 $R^{11}$;

$R^{34}$ and $R^{35}$ can be taken together to form a ketal ring, a 3- to 8-membered carbocyclic ring, or a 5- or 6-membered heterocyclic ring containing 1–3 heteroatoms independently selected from the group O, N, or S, said ring substituted with 0–5 $R^{11}$;

$R^{36}$ is selected from:
  H
  $C_1-C_6$ alkyl substituted with 0–3 $R^{11}$;
  $-COR^{37}$;
  $-NR^{38}R^{39}$;
  $-CN$;
  $-NO_2$ $R^{37}$ is selected from:
  hydrogen; $C_1-C_6$ alkyl substituted with 0–3 $R^{11}$;
  hydroxyl;
  $C_1-C_6$ alkoxy substituted with 0–3 $R^{11}$; $-NR^{38}R^{39}$;

$R^{38}$ and $R^{39}$ are independently selected from:
hydrogen;
$C_1$–$C_6$ alkyl substituted with 0–3 $R^{11}$; or
an amine protecting group;

$R^{40}$ is selected from: H, $C_1$–$C_3$ alkyl;

$R^{41}$ is selected from:
—C(=O)$NR^{13}R^{14}$;
—C(=O)$NR^{13}NR^{14}$;
—C(=O)C($R^{11}$)$_2$$NR^{13}R^{14}$;
—C(=O)C($R^{11}$)$_2$$NR^{13}NR^{14}$;
—C(=O)C($R^{11}$)$_2$$NR^{13}CO_2R^{13}$;
—C(=O)H;
—C(=O)$R^{11}$;
—C(=O)—($C_1$–$C_4$ alkyl)—$NR^{13}R^{14}$;
—C(=O)—($C_1$–$C_4$ alkyl)—$NR^{13}CO_2R^{13}$;
1–3 amino acids linked together via amide bonds, and linked to the N atom via the carboxylate terminus;
provided that:
$R^4$, $R^{4A}$, $R^7$ and $R^{7A}$ are not all hydrogen;
when W is —OC(=Z)O—, —SC(=Z)—, —C(=Z)—, —P(=O)($R^{24a}$)—, —S(=Z')— or —S(=Z')$_2$—, $R^4$ and $R^7$ are not hydrogen;
when $R^4$ $R^{4A}$ are hydrogen, at least one of the following is not hydrogen: $R^{22}$, $R^{25}$, and $R^{26}$.

[2] Preferred compounds of component(i) useful in the method of the present invention are compounds of Formula (I) wherein:

$R^4$ and $R^7$ are independently selected from the following groups:
hydrogen;
$C_1$–$C_4$ alkyl substituted with 0–3 $R^{11}$;
$C_3$–$C_4$ alkenyl substituted with 0–3 $R^{11}$;
$C_3$–$C_4$ alkynyl substituted with 0–3 $R^{11}$;

$R^{4A}$ and $R^{7A}$ are hydrogen;

n is 0, 1, or 2;

$R^5$ is selected from fluoro or —$OR^{20}$;

$R^6$ is independently selected from: hydrogen, fluoro or —$OR^{21}$;

$R^5$ and $R^6$ can alternatively join to form an epoxide or aziridine ring; —OCH$_2$SCH$_2$O—; —OS(=O)O—; —OC(=O)O—; —OCH$_2$O—; —OC(=S)O—; —OC(=O)C(=O)O—; —OC(CH$_3$)$_2$O—; —OC(OCH$_3$)(CH$_2$CH$_2$CH$_3$)O—; or any group that, when administered to a mammalian subject, cleaves to form a free dihydroxyl;

$R^{5a}$ is selected from hydrogen or fluoro;

$R^{6a}$ is selected from: hydrogen or fluoro;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
hydrogen;
$C_1$–$C_6$ alkylcarbonyl;
$C_1$–$C_6$ alkoxycarbonyl;
benzoyl; or
any group that, when administered to a mammalian subject, cleaves to form a free hydroxyl;

$R^{11}$ is selected from one or more of the following:
H, keto, halogen, cyano, —CH$_2$$NR^{13}R^{14}$, —$NR^{13}R^{14}$ —CO$_2$$R^{13}$, —OC(=O)$R^{13}$, —$OR^{13}$, $C_2$–$C_4$ alkoxyalkyl, —S(O)$_m$$R^{13}$, $C_1$–$C_4$ alkyl, $C_2$–$C_4$ alkenyl, $C_3$–$C_{10}$ cycloalkyl;
a $C_5$–$C_{14}$ saturated or partially unsaturated carbocyclic residue substituted with 0–3 $R_{12}$;
aryl($C_1$–$C_3$ alkyl) substituted with 0–2 $R^{12}$;
aryl substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl,
$C_1$–$C_4$ alkoxy, —CO$_2$H, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(O)$_m$$R^{13}$, —SO$_2$$NR^{13}R^{14}$, —NHSO$_2$$R^{14}$; or a 5- or 6-membered heterocyclic ring containing from 1 to 4 heteroatoms independently selected from oxygen, nitrogen or sulfur;

or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$;
or, when $R^{12}$ is attached to a saturated carbon atom, it may be =O or =S;

$R^{12}$ when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$$NR^{13}R^{14}$, —$NR^{13}R^{14}$, $C_1$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, —CO$_2$H;

$R^{13}$ is H, $C_1$–$C_6$ alkyl, $C_3$–$C_6$ alkoxyalkyl, $C_2$–$C_4$ alkenyl, phenyl, or benzyl;

$R^{14}$ is OH, H, CF$_3$, $C_1$–$C_4$ alkyl, $C_1$–$C_4$ alkoxy, NH$_2$, $C_2$–$C_4$ alkenyl, phenyl, or benzyl;

$R^{13}$ and $R^{14}$ can alternatively join to form —(CH$_2$)$_4$—, —(CH$_2$)$_5$—, —CH$_2$CH$_2$N($R^{15}$)CH$_2$CH$_2$—, or —CH$_2$CH$_2$OCH$_2$CH$_2$—;

$R^{15}$ is H or CH$_3$;

m is 0, 1 or 2;

W is selected from:
—N($R^{22}$)C(=Z)N($R^{23}$)—;
—N($R^{22}$)C(=Z)O—;
—C($R^{25}$)($R^{26}$)C(=Z)C($R^{27}$)($R^{28}$)—;
—N($R^{22}$)C(=Z)C($R^{27}$)($R^{28}$)—;
—C($R^{25}$)($R^{26}$)C(=Z)O—;
—N($R^{22}$)C(=O)C(=O)N($R^{23}$)—;
—C($R^{25}$)($R^{26}$)C(F$_2$)C($R^{27}$)($R^{28}$)—;
—C($R^{25}$)($R^{26}$)N(CH$_3$)(O)C($R^{27}$)($R^{28}$)—;
—C($R^{25}$)($R^{26}$)N(O$R^{29}$)C($R^{27}$)($R^{28}$)—;
—C($R^{25}$)($R^{26}$)C(=Z)S—;
—N($R^{22}$)S(=Z')N($R^{23}$)—;
—N($R^{22}$)S(=Z')$_2$N($R^{23}$)—;
—N($R^{22}$)P(=O)($R^{24a}$)(N($R^{23}$)—;
—C($R^{25}$)($R^{26}$)S(=Z')C($R^{27}$)($R^{28}$)—;
—C($R^{25}$)($R^{26}$)S(=Z')$_2$C($R^{27}$)($R^{28}$)—;
—C($R^{25}$)($R^{26}$)P(=O)($R_{24a}$)C($R^{27}$)($R^{28}$)—;

—C($R^{25}$)($R^{26}$)S(=Z')N($R^{23}$)—;
—C($R^{25}$)($R^{26}$)S(=Z')$_2$N($R^{23}$)—;
—C($R^{25}$)($R^{26}$)S(=O)$_2$O—;
—C($R^{25}$)($R^{26}$)P(=O)($R_{24a}$)N($R^{23}$)—;
—C($R^{25}$)($R^{26}$)P(=O)($R_{24a}$)O—;
—C($R^{25}$)C(F$_2$)C(=O)N($R^{23}$)—;
—C($R_{25}$)C(F$_2$)S(=O)$_2$N($R^{23}$)—;
—C($R^{25}$)($R^{26}$)C($R^{34}$)($R^{35}$)C($R^{27}$)($R^{28}$)—;
—N=C($R^{36}$)N($R^{23}$)—;   —N($R^{22}$)p($R_{24a}$)N($R^{23}$)—;
—C(=Z)—;   —P(=O)($R^{24a}$)—;   —S(=Z')—;
—S(=Z')$_2$—;

wherein:

Z is O, S, N—CN, N—OH, N—OCH$_3$;

Z' is oxygen:

$R^{22}$ and $R^{23}$ are independently selected from the following:
 hydrogen;
 $C_1$–$C_8$ alkyl substituted with 0–3 $R^{31}$;
 $C_3$–$C_8$ alkenyl substituted with 0–3 $R^{31}$;
 $C_3$–$C_8$ alkynyl substituted with 0–3 $R^{31}$;
 $C_3$–$C_6$ cycloalkyl substituted with 0–3 $R^{31}$;

$R^{24a}$ is selected from —OH, $C_1$–$C_4$ alkoxy, mono- or di-($C_1$–$C_6$ alkyl)amino;

$R^{25}$ and $R^{27}$ are independently selected from the following:
 hydrogen;
 $C_1$–$C_8$ alkyl substituted with 0–3 $R^{31}$;
 $C_2$–$C_8$ alkenyl substituted with 0–3 $R^{31}$;
 $C_3$–$C_8$ alkynyl substituted with 0–3 $R^{31}$;

$R^{26}$ and $R^{28}$ are hydrogen or halogen;

$R^{29}$ is selected from:
 hydrogen;
 $C_1$–$C_2$ alkyl substituted with 0–2 $C_1$–$C_2$ alkoxy; benzyl substituted with 0–2 halogen or $C_1$–$C_2$ alkoxy;

$R^{31}$ is selected from one or more of the following:
 keto, halogen, cyano, —CH$_2$NR$^{13}$R$^{14}$, —NR$^{13}$R$^{14}$, —CO$_2$R$^{13}$, —OC(=O)R$^{13}$, —OR$^{13}$, $C_2$–$C_4$ alkoxyalkyl —S(O)$_m$R$^{13}$, $C_1$–$C_4$ alkyl, $C_2$–$C_4$ alkenyl, $C_3$–$C_{10}$ cycloalkyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —NR$^{13}$R$^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$CO$_2$H, 2-(1-morpholino)ethoxy, —C(R$^{14}$)=N(OR$^{14}$); or
 a $C_5$–$C_{14}$ saturated or partially unsaturated carbocyclic residue substituted with 0–3 $R^{32}$;
 aryl substituted with 0–3 $R^{32}$; or
 a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$ when a substituent on carbon, is selected from one or more of the following:
 phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —NHSO$_2$R$^{14}$, benzyloxy, halogen, 2-(1-morpholino)ethoxy, —CO$_2$R$^{13}$, hydroxamic acid, —CONR$^{13}$NR$^{13}$R$^{14}$, cyano, boronic acid, sulfonamide, —CHO, $C_3$–$C_6$ cycloalkoxy, —NR$^{13}$R$^{14}$, —C(R$^{14}$)=N(OR$^{14}$), NO$_2$, —OR$^{13}$, —NR$^{40}$R$^{41}$,
—SO$_m$R$^{13}$, —SO$_m$NR$^{13}$R$^{14}$, —C(=O)NR$^{13}$R$^{14}$,
—OC(=O)NR$^{13}$R$^{14}$, —C(=O)R$^{11}$,
—OC(=O)R$^{11}$, —OCO$_2$R$^{13}$, phenyl,
—C(=O)NR$^{13}$—($C_1$–$C_4$ alkyl)—NR$^{13}$R$^{14}$,
—C(=O)NR$^{40}$R$^{41}$, $C_1$–$C_4$ haloalkyl, $C_1$–$C_4$ haloalkoxy, $C_2$–$C_4$ haloalkenyl, $C_1$–$C_4$ haloalkynyl, or
—C(=O)NR$^{13}$C(R$^{11}$)$_2$NR$^{13}$R$^{14}$;
 —C(=O)NR$^{13}$C(R$^{11}$)$_2$NR$^{13}$NR$^{14}$;
 —C(=O)NR$^{13}$C(R$^{11}$)$_2$NR$^{13}$CO$_2$R$^{13}$;
 —C(=O)NR$^{13}$—($C_1$–$C_4$ alkyl)—NR$^{13}$CO$_2$R$^{13}$; or
 —C(=O)C(R$^{11}$)$_2$NR$^{13}$R$^{14}$;
 —C(=O)C(R$^{11}$)$_2$NR$^{13}$NR$^{14}$;
 —C(=O)C(R$^{11}$)$_2$NR$^{13}$CO$_2$R$^{13}$;   —C(=O)—($C_1$–$C_4$ alkyl)—NR$^{13}$R$^{14}$; —C(=O)—($C_1$–$C_4$ alkyl)—NR$^{13}$CO$_2$R$^{13}$; or $C_1$–$C_4$ alkoxy substituted with 0–3 groups selected from: $R^{11}$, $C_3$–$C_6$ cycloalkyl, —CO$_2$R$^{13}$, —C(=O)NR$^{13}$R$^{14}$ —NR$^{13}$R$^{14}$ or OH;

$C_1$–$C_4$ alkyl substituted with 0–3 groups selected from: $R^{11}$, =NR$^{14}$, =NNR$^{13}$C(=O)NR$^{13}$R$^{14}$ or —NR$^{13}$R$^{14}$;

$C_2$–$C_4$ alkenyl substituted with 0–3 $R^{11}$;

$C_2$–$C_4$ alkynyl substituted with 0–3 $R^{11}$;

a 5- or 6-membered heterocyclic ring containing from 1 to 4 heteroatoms independently selected from oxygen, nitrogen or sulfur;

or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —NR$^{13}$R$^{14}$; or, when $R^{32}$ is attached to a saturated carbon atom, it may be =O or =S;

$R^{32}$ when a substituent on nitrogen, is selected from one or more of the following:
 phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —CH$_2$NR$^{13}$R$^{14}$, —NR$^{13}$R$^{14}$, $C_1$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, —CO$_2$H, —C(R$^{14}$)=N(OR$^{14}$);

$R^{34}$ is selected from:
 hydrogen;
 $C_1$–$C_2$ alkyl substituted with 0–1R$^{11}$
 $C_1$–$C_2$ alkoxy substituted with 0–1R$^{11}$ $R^{35}$ is selected from:
 hydrogen
 $C_1$–$C_2$ alkyl substituted with 0–1 $R^{11}$
 $C_1$–$C_2$ alkoxy substituted with 0–1R$^{11}$ $R^{34}$ and $R^{35}$ can be taken together to form a ketal ring, a 3- to 8-membered carbocyclic ring, or a 5- or 6-membered heterocyclic ring containing 1–3 heteroatoms independently selected from the group O, N, or S;

$R^{36}$ is selected from:
 $C_1$–$C_2$ alkyl substituted with 0–3 $R^{11}$;
 COR$^{37}$;
 NR$^{38}$R$^{39}$;
 CN;

$R^{37}$ is selected from:
 hydrogen;
 $C_1$–$C_2$ alkyl substituted with 0–1R$^{11}$;
 hydroxyl;
 $C_1$–$C_2$ alkoxy substituted with 0–1R$^{11}$;
 NR$^{38}$R$^{39}$;

$R^{38}$ and $R^{39}$ are independently selected from:
  hydrogen;
  $C_1-C_2$ alkyl substituted with 0–3 $R^{11}$; or
  an amine protecting group;

$R^{40}$ is selected from: H, $C_1-C_3$ alkyl;

$R^{41}$ is selected from:
  —C(=O)NR$^{13}$R$^{14}$;
  —C(=O)NR$^{13}$NR$^{14}$;
  —C(=O)C(R$^{11}$)$_2$NR$^{13}$R$^{14}$;
  —C(=O)C(R$^{11}$)$_2$NR$^{13}$NR$^{14}$;
  —C(=O)C(R$^{11}$)$_2$NR$^{13}$CO$_2$R$^{13}$;
  —C(=O)H;
  —C(=O)R$^{11}$;
  —C(=O)—(C$_1$–C$_4$ alkyl)—NR$^{13}$R$^{14}$;
  —C(=O)—(C$_1$–C$_4$ alkyl)—NR$^{13}$CO$_2$R$^{13}$;
  1–3 amino acids linked together via amide bonds, and linked to the N atom via the carboxylate terminus;

provided that:
  $R^4$, $R^{4A}$, $R^7$, and $R^{7A}$ are not all hydrogen;
  when W is —OC(=Z)O—, —C(=Z)—, —P(=O)(R$^{24a}$)—, —S(=Z')— or —S(=Z')$_2$—, $R^4$ and $R^7$ are not hydrogen;
  when $R^4$ and $R^{4A}$ are hydrogen, at least one of the following is not hydrogen: $R^{22}$, $R^{25}$, and $R^{26}$.

[3] More preferred compounds of component(i) useful in the present invention include compounds of Formula (II):

$$R^4 \underset{R^5 \quad R^6}{\overset{W}{\diagdown}} R^7 \qquad (II)$$

or a pharmaceutically acceptable salt thereof, wherein:

$R^4$ and $R^7$ are independently selected from the following groups:
  hydrogen;
  $C_1-C_3$ alkyl substituted with 0–1R$^{11}$;

$R^5$ is —OR$_{20}$;

$R^6$ is hydrogen or —OR$_{21}$;

$R^{20}$ and $R^{21}$ are independently hydrogen or any group that, when administered to a mammalian subject, cleaves to form a free hydroxyl;

$R^{11}$ is selected from one or more of the following:
  H; halogen; —OR$^{13}$;
  $C_3-C_{10}$ cycloalkyl substituted with 0–2 $R^{12}$;
  $C_1-C_4$ alkyl substituted with 0–2 $R^{12}$;
  aryl($C_1-C_3$ alkyl) substituted with 0–2 $R^{12}$;
  aryl substituted with 0–2 $R^{12}$; or
  a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{12}$ when a substituent on carbon, is selected from one or more of the following:
  benzyloxy, halogen, methyl, $C_1-C_4$ alkoxy, $CF_3$, 2-(1-morpholino)ethoxy, —CO$_2$H, hydroxamic acid, hydrazide, —C(R$^{14}$)=N(OR$^{14}$), cyano, boronic acid, sulfonamide, formyl, $C_3-C_6$ cycloalkoxy, $C_1-C_4$ alkyl substituted with —NR$^{13}$R$^{14}$, —NR$^{13}$R$^{14}$, hydroxy, hydroxymethyl; or $R^{12}$, when a substituent on nitrogen, is methyl;

$R^{13}$ is H, $C_1-C_4$ alkyl, $C_2-C_4$ alkenyl, or benzyl;

$R^{14}$ is OH, H, $CF_3$, $C_1-C_4$ alkyl, $C_1-C_4$ alkoxy, NH$_2$, $C_2-C_4$ alkenyl, or benzyl;

$R^{13}$ and $R^{14}$ can alternatively join to form —(CH$_2$)$_4$—, —(CH$_2$)$_5$—, —CH$_2$CH$_2$N(R$^{15}$)CH$_2$CH$_2$—, or —CH$_2$CH$_2$OCH$_2$CH$_2$—;

$R^{15}$ is H or $CH_3$;

W is selected from:
  —N(R$^{22}$)C(=Z)N(R$^{23}$)—;
  —N(R$^{22}$)C(=Z)O—;
  —C(R$^{25}$)(R$^{26}$)C(=Z)C(R$^{27}$)(R$^{28}$)—;
  —N(R$^{22}$)S(=Z')N(R$^{23}$)—;
  —N(R$^{22}$)S(=Z')$_2$N(R$^{23}$)—;
  —C(R$^{25}$)(R$^{26}$)C(R$^{34}$)(R35)C(R$^{27}$)(R$^{28}$)—;
  —N=C(R$^{36}$)N(R$^{23}$)—;
  —C(=Z)—;

Z is O, S, or N—CN;

Z' is O;

$R^{22}$ and $R^{23}$ are independently selected from the following:
  hydrogen;
  $C_1-C_8$ alkyl substituted with 0–3 $R^{31}$;
  $C_2-C_6$ alkenyl substituted with 0–3 $R^{31}$;
  $C_2-C_4$ alkynyl substituted with 0–3 $R^{31}$;

$R^{25}$ and $R^{27}$ are independently selected from the following:
  hydrogen;
  $C_1-C_4$ alkyl substituted with 0–3 $R^{31}$;
  $C_3-C_4$ alkenyl substituted with 0–3 $R^{31}$;

$R^{26}$ and $R^{28}$ are hydrogen or halogen;

$R^{31}$ is selected from one or more of the following:
  halogen, —OR$^{13}$, $C_1-C_4$ alkyl, $C_3-C_{10}$ cycloalkyl, —C(R$^{14}$)=N(OR$^{14}$), —CO$_2$R$^{13}$, —S(O)$_m$R$^{13}$;
  aryl substituted with 0–5 $R^{32}$; or
  a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;

$R^{32}$, when a substituent on carbon, is selected from one or more of the following:
  benzyloxy, halogen, 2-(1-morpholino)ethoxy, —CO$_2$R$^{13}$ hydroxamic acid, —CONR$^{13}$NR$^{13}$R$^{14}$, cyano, boronic acid, sulfonamide, —CHO, $C_3-C_6$ cycloalkoxy, —NR$^{13}$R$^{14}$, —C(R$^{14}$)=N(OR$^{14}$), NO$_2$, —OR$^{13}$, —NR$^{40}$R$^{41}$, —SO$_m$R$^{13}$, —SO$_m$NR$^{13}$R$^{14}$, —C(=O)NR$^{13}$R$^{14}$, —OC(=O)NR$^{13}$R$^{14}$, —C(=O)R$^{11}$, —OC(=O)R$^{11}$, —OCO$_2$R$^{13}$, phenyl, —C(=O)NR$^{13}$—(C$_1$–C$_4$ alkyl)—NR$^{13}$R$^{14}$, —C(=O)NR$^{40}$R$^{41}$, $C_1-C_4$ haloalkyl, $C_1-C_4$ haloalkoxy, $C_2-C_4$ haloalkenyl, $C_1-C_4$ haloalkynyl, —C(=O)NR$^{13}$R$^{14}$; —C(=O)C(R$^{11}$)$_2$NR$^{13}$R$^{14}$; —C(=O)C(R$^{11}$)$_2$NR$^{13}$NR$^{14}$; —C(=O)C(R$^{11}$)$_2$NR$^{13}$CO$_2$R$^{13}$; —C(=O)—(C$_1$–C$_4$ alkyl)—NR$^{13}$R$^{14}$; —C(=O)—(C$_1$–C$_4$ alkyl)—NR$^{13}$CO$_2$R$^{13}$; or
  $C_1-C_4$ alkoxy substituted with 0–3 groups selected from: $R^{11}$, $C_3-C_6$ cycloalkyl, —C(=O)NR$^{13}$R$^{14}$, —NR$^{13}$R$^{14}$ or OH;
  $C_1-C_4$ alkyl substituted with 0–3 groups selected from: $R^{11}$, =NR$^{14}$, =NNR$^{13}$C(=O)NR$^{13}$R$^{14}$ or —NR$^{13}$R$^{14}$;
  $C_2-C_4$ alkenyl substituted with 0–3 $R^{11}$;
  $C_2-C_4$ alkynyl substituted with 0–3 $R^{11}$;
  a 5- or 6-membered heterocyclic ring containing from 1 to 4 heteroatoms independently selected from oxygen, nitrogen or sulfur;

$R^{32}$, when a substituent on nitrogen, is methyl;

m is 0, 1, or 2;

$R^{34}$ is selected from:
hydrogen;
$C_1$–$C_2$ alkyl;
$C_1$–$C_2$ alkoxy;

$R^{35}$ is selected from:
hydrogen;
$C_1$–$C_2$ alkyl;
$C_1$–$C_2$ alkoxy;

$R^{36}$ is selected from: $C_1$–$C_2$ alkyl; $COR^{37}$; $NR^{38}R^{39}$; CN; $CCl_3$;

$R^{37}$ is selected from:
hydrogen;
$C_1$–$C_2$ alkyl substituted with 0–1 $R^{11}$;
hydroxyl;
$C_1$–$C_2$ alkoxy substituted with 0–1 $R^{11}$;
—$NR^{38}R^{39}$;

$R^{38}$ and $R^{39}$ are independently selected from:
hydrogen;
$C_1$–$C_2$ alkyl substituted with 0–3 $R^{11}$; or an amine protecting group;

$R^{40}$ is selected from: H, $C_1$–$C_3$ alkyl;

$R^{41}$ is selected from:
—C(=O)$NR^{13}R^{14}$;
—C(=O)$NR^{13}NR^{14}$;
—C(=O)$C(R^{11})_2NR^{13}R^{14}$;
—C(=O)$C(R^{11})_2NR^{13}NR^{14}$;
—C(=O)$C(R^{11})_2NR^{13}CO_2R^{13}$;
—C(=O)H;
—C(=O)$R^{11}$;
—C(=O)—($C_1$–$C_4$ alkyl)—$NR^{13}R^{14}$;
—C(=O)—($C_1$–$C_4$ alkyl)—$NR^{13}CO_2R^{13}$;
1–3 amino acids linked together via amide bonds, and linked to the N atom via the carboxylate terminus;

provided that:
$R^4$ and $R^7$ are not both hydrogen;
when W is —C(=Z)—, $R^4$ and $R^7$ are not hydrogen;
when $R^4$ is hydrogen, at least one of the following is not hydrogen: $R^{22}$, $R^{25}$, $R^{26}$ and $R^{28}$.

[4] Preferred compounds of component(ii) of Formula (II) of the present invention are compounds described above, wherein:

$R^4$ and $R^7$ are selected from benzyl, fluorobenzyl, pyrrolylmethyl, methoxybenzyl, isobutyl, nitrobenzyl or aminobenzyl;

$R^5$ is —OH;

$R^6$ is hydrogen or —OH;

$R^{13}$ is H, $C_1$—$C_4$ alkyl, $C_2$–$C_4$ alkenyl, or benzyl;

$R^{14}$ is OH, H, $CF_3$, $C_1$-$C_4$ alkyl, $C_1$-$C_4$ alkoxy, $NH_2$, $C_2$–$C_4$ alkenyl, or benzyl;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

W is selected from:
—$N(R^{22})C(=O)N(R^{23})$—;
—$N(R^{22})C(=N—CN)N(R^{23})$—;
—$N(R^{22})S(=O)_2N(R^{23})$—;
—C(=O)—;
—$N(R^{22})C(=S)N(R^{23})$—; or
—C(=N—CN)—;

$R^{22}$ and $R^{23}$ are independently selected from the following:
hydrogen;
$C_1$–$C_8$ alkyl substituted with 0–2 $R^{31}$;

$C_1$–$C_6$ alkenyl substituted with 0–2 $R^{31}$;
$C_2$–$C_4$ alkynyl substituted with 0–2 $R^{31}$;

$R^{31}$ is selected from one or more of the following:
halogen, —$OR^{13}$, $C_1$–$C_4$ alkyl, $C_3$–$C_{10}$ cycloalkyl, —$C(R^{14})=N(OR^{14})$, —$CO_2R^{13}$, —$S(O)_mR^{13}$;
aryl substituted with 0–5 $R^{32}$; or
a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;

$R^{32}$, when a substituent on carbon, is selected from one or more of the following:
—$CONH_2$, —$CO_2H$, —CHO, —$CH_2NHOH$, —$CH_2NR^{13}R^{14}$, —$NR^{13}R^{14}$, hydroxy, hydroxymethyl, —$C(R^{14})=N(OR^{14})$, halogen, methoxy, methyl, nitro, cyano, allyloxy, —$CO_2CH_3$, —NHCHO, —$NHCOCH_3$, —$OCO_2CH_3$, —CH=$NCH_2CH_2OH$, —$OCONHCH_2C_6H_5$, —$OCONHCH_3$, oxazolidinyl, —C≡C—$CH_2OH$, —$COCH_3$, hydroxyethyl, $C_1$–$C_3$ alkyl (said alkyl substituted with 0–4 halogen, or OH), tetrazolyl, —$OCH_2CONH_2$, —$CONHNH_2$, —CH=$NNHCONH_2$, —$CONHOCH_3$, —$CH_2CH(OH)CH_2OH$, adamantamido, hydroxyethoxy, dihydroxyethyl, —$C(NH_2)=NH$, —$CONHCH_3$, —$B(OH)_2$, benzyloxy, —$CONHCH_2CH_3$, —$CON(CH_2CH_3)_2$, methylthio, —$SO_2CH_3$, —$NHCONH_2$, —$NHCONHCH_3$, —$NHCOCH_2N(CH_3)_2$, —$NHCOCH_2NHCH_3$, —$NHCOCH_2NHCO_2CH_2C_6H_5$, —$NHCOCH_2NH_2$, —$NHCOCH(CH_3)NHCO_2CH_2C_6H_5$, —$NHCOCH(CH_2C_6H_5)NHCO_2CH_2C_6H_5$, —$NHCOCH(CH_3)NH_2$, —$NHCOCH(CH_2C_6H_5)NH_2$, —$CO_2CH_2CH_3$, —$CONHCH_2CH^3$, —$CONHCH(CH_3)_2$, —$CH_2$-imidazole, —$COC(CH_3)_3$, —$CH(OH)CF_3$, —CO-imidazole, —CO-pyrazolyl, oxadiazolidinonyl, —$COCF_3$, —$COCH_2CH_3$, —$COCH_2CH_2CH_3$, pyrazolyl, —$SO_2NH_2$, —$C(CH_2CH_3)=N(OH)$ or —$C(CF_3)=N(OH)$, phenyl, acetoxy, hydroxyamino, —$N(CH_3)(CHO)$, cyclopropylmethoxy, —$CONR^{13}R^{14}$—, CONHOH, (diethylaminoethyl)aminocarbonyl, (N-ethyl, N-methylaminoethyl)aminocarbonyl, (4-methylpiperazinylethyl)aminocarbonyl, pyrrolidinylethyl)aminocarbonyl, (piperidinylethyl)aminocarbonyl, —$NHCOCH_2NHCH_3$, N-(2-(4-morpholino)ethyl)aminocarbonyl, N-(2-(N, N-dimethylamino)ethyl)aminocarbonyl;

$R^{32}$, when a substituent on nitrogen, is methyl.

[5] Preferred compounds of component(i) of the invention are compounds of Formula (II) having the formula:

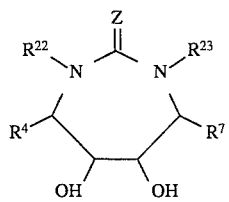

wherein:
Z is O, S, or N—CN;

$R^4$ and $R^7$ are independently selected from: benzyl, fluorobenzyl, pyrrolylmethyl, methoxybenzyl, isobutyl, nitrobenzyl or aminobenzyl;

$R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N, N-dimethylaminocarbonylbenzyl, $(HOCH_2CH(OH)CH_2O)$benzyl, hydroxyethoxybenzyl(oxazolidinyl)—benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N, N-dimethylaminomethylbenzyl, N-methylaminomethylbenzyl, glycylaminobenzyl, N, N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, $(CH_3CH_2NHC(=O))$-benzyl, N, N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, $(H_2NSO_2)$-benzyl, dihydroxyethylbenzyl, $(MeHNC(=O)NH)$-benzyl, $(H_2NC(=O)NH)$-benzyl, $(HC(=O)NH)$-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl)benzyl, $(CF_3C(=NOH))$-benzyl, (N-methylglycyl)aminobenzyl, ((4-morpholino)ethyl)aminocarbonylbenzyl, (N, N-dimethylaminoethyl)aminocarbonylbenzyl, (N, N-diethylaminoethyl)aminocarbonylbenzyl, (4-methylpiperazin-1-ylethyl)aminocarbonylbenzyl, (benzyl-NHC(=O)O)benzyl, $(CH_3NHC(=O)O)$benzyl, $(NH_2C(=O)CH_2O)$benzyl, $(NH_2C(=NH))$benzyl, ((N-phenylmethoxycarbonyl)glycylamino)benzyl, (imidazolylmethyl)benzyl, $((CH_3)_3C—C(=O))$benzyl, (N-methyl-N-ethylaminoethyl)aminocarbonylbenzyl, (pyrrolidinylethyl)aminocarbonylbenzyl, (piperidinylethyl)aminocarbonylbenzyl.

[6] Preferred compounds of component(i) of the invention are compounds of Formula (IIa):

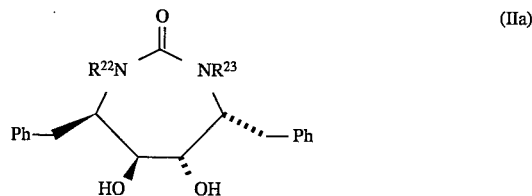

(IIa)

wherein $R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyloxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxine)benzyl, $(CH_3O_2CO)$-benzyl, $(HOCH_2CH_2N=CH)$, benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N, N-dimethylaminocarbonylbenzyl, $(HOCH_2CH(OH)CH_2O)$-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N, N-dimethylaminomethylbenzyl, N-methylaminomethylbenzyl, glycylaminobenzyl, N, N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, $(CH_3CH_2NHC(=O))$-benzyl, N, N-diethylaminocarbonylbenzyl, N-ethylaminocarbonylbenzyl, N-propylaminocarbonylbenzyl, N,N-diisopropylaminocarbonylbenzyl, N, N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl (oxadiazolidinonyl)benzyl, trifluoroacetylbenzyl, (pyrazolyl)benzyl, $(H_2NSO_2$ )-benzyl, dihydroxyethylbenzyl, $(MeHNC(=O)NH)$-benzyl, $(H_2NC(=O)NH)$-benzyl, $(HC(=O)NH)$-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl-)benzyl, (CF$_3$C(=NOH))-benzyl, (N-methylglycyl)aminobenzyl, (4-morpholino)ethyl )aminocarbonylbenzyl, (N, N-dimethylaminoethyl )aminocarbonylbenzyl, (N, N-diethylaminoethyl )aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

[7] Specifically preferred compounds of component(i) of the invention are compounds having the Formula (IIa):

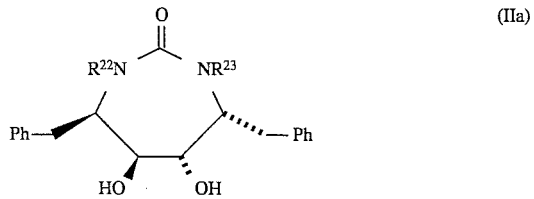

selected from the group consisting of:

the compound of Formula (IIa) wherein R$^{22}$ is allyl and R$^{23}$ is allyl;

the compound of Formula (IIa) wherein R$^{22}$ is propyl and R$^{23}$ is propyl;

the compound of Formula (IIa) wherein R$^{22}$ is cyclopropylmethyl and R$^{23}$ is cyclopropylmethyl;

the compound of Formula (IIa) wherein R$^{22}$ is n-hexyl and R$^{23}$ is n-hexyl;

the compound of Formula (IIa) wherein R$^{22}$ is n-butyl and R$^{23}$ is n-butyl;

the compound of Formula (IIa) wherein R$^{22}$ is CH$_2$CH=C(CH$_3$)$_2$ and R$^{23}$ is CH$_2$CH=C(CH$_3$)$_2$;

the compound of Formula (IIa) wherein R$^{22}$ is CH$_2$CH=C(CH$_3$)$_2$ and R$^{23}$ is H;

the compound of Formula (IIa) wherein R$^{22}$ is i-pentyl and R$^{23}$ is i-pentyl;

the compound of Formula (IIa) wherein R$^{22}$ is 2-methallyl and R$^{23}$ is 2-methallyl;

the compound of Formula (IIa) wherein R$^{22}$ is n-pentyl and R$^{23}$ is n-pentyl;

the compound of Formula (IIa) wherein R$^{22}$ is benzyl and R$^{23}$ is benzyl;

the compound of Formula (IIa) wherein R$^{22}$ is i-hexyl and R$^{23}$ is i-hexyl;

the compound of Formula (IIa) wherein R$^{22}$ is allyl and R$^{23}$ is isoprenyl;

the compound of Formula (IIa) wherein R$^{22}$ is 1-cinnamyl and R$^{23}$ is 1-cinnamyl;

the compound of Formula (IIa) wherein R$^{22}$ is 4-fluorobenzyl and R$^{23}$ is 4-fluorobenzyl;

the compound of Formula (IIa) wherein R$^{22}$ is cyclopropylmethyl and R$^{23}$ is benzyl;

the compound of Formula (IIa) wherein R$^{22}$ is allyl and R$^{23}$ is benzyl;

the compound of Formula (IIa) wherein R$^{22}$ is CH$_2$CH=C(CH$_3$)$_2$ and R$^{23}$ is cyclopropylmethyl;

the compound of Formula (IIa) wherein R$^{22}$ is 2-naphthylmethyl and R$^{23}$ is 2-napthylmethyl;

the compound of Formula (IIa) wherein R$^{22}$ is n-butyl and R$^{23}$ is benzyl;

the compound of Formula (IIa) wherein R$^{22}$ is allyl and R$^{23}$ is cyclopropylmethyl;

the compound of Formula (IIa) wherein R$^{22}$ is n-butyl and R$^{23}$ is cyclopropylmethyl;

the compound of Formula (IIa) wherein R$^{22}$ is CH$_2$CH=C(CH$_3$)$_2$ and R$^{23}$ is benzyl;

the compound of Formula (IIa) wherein R$^{22}$ is benzyl and R$^{23}$ is ethyl;

the compound of Formula (IIa) wherein R$^{22}$ is benzyl and R$^{23}$ is 4-pyridinylmethyl;

the compound of Formula (IIa) wherein R$^{22}$ is cyclopropylmethyl and R$^{23}$ is 4-pyridinylmethyl;

the compound of Formula (IIa) wherein R$^{22}$ is benzyl and R$^{23}$ is cyclopentylmethyl;

the compound of Formula (IIa) wherein R$^{22}$ is cyclopropylmethyl and R$^{23}$ is cyclopentylmethyl;

the compound of Formula (IIa) wherein R$^{22}$ is benzyl and R$^{23}$ is n-propyl;

the compound of Formula (IIa) wherein R$^{22}$ is cyclopropylmethyl and R$^{23}$ is cinnamyl;

the compound of Formula (IIa) wherein R$^{22}$ is cyclopropylmethyl and R$^{23}$ is 2-naphthylmethyl;

the compound of Formula (IIa) wherein R$^{22}$ is cyclopentylmethyl and R$^{23}$ is 2-naphthylmethyl;

the compound of Formula (IIa) wherein R$^{22}$ is benzyl and R$^{23}$ is 2-naphthylmethyl;

the compound of Formula (IIa) wherein R$^{22}$ is cyclopropylmethyl and R$^{23}$ is 2-pyridinylmethyl;

the compound of Formula (IIa) wherein R$^{22}$ is 3-cyanobenzyl and R$^{23}$ is 3-cyanobenzyl;

the compound of Formula (IIa) wherein R$^{22}$ is allyl and R$^{23}$ is 2-naphthylmethyl;

the compound of Formula (IIa) wherein R$^{22}$ is n-propyl and R$^{23}$ is 2-naphthylmethyl;

the compound of Formula (IIa) wherein R$^{22}$ is n-butyl and R$^{23}$ is 2-naphthylmethyl;

the compound of Formula (IIa) wherein R$^{22}$ is hydrogen and R$^{23}$ is 2-naphthylmethyl;

the compound of Formula (IIa) wherein R$^{22}$ is 4-pyridinylmethyl and R$^{23}$ is 2-naphthylmethyl;

the compound of Formula (IIa) wherein R$^{22}$ is allyl and R$^{23}$ is cyclopentylmethyl;

the compound of Formula (IIa) wherein R$^{22}$ is allyl and R$^{23}$ is 2-quinolinylmethyl;

the compound of Formula (IIa) wherein R$^{22}$ is 3-pyridinylmethyl and R$^{23}$ is cyclopropylmethyl;

the compound of Formula (IIa) wherein R$^{22}$ is 3-pyridinylmethyl and R$^{23}$ is 2-naphthylmethyl;

the compound of Formula (IIa) wherein R$^{22}$ is 3-hydroxybenzyl and R$^{23}$ is 3-hydroxybenzyl;

the compound of Formula (IIa) wherein R$^{22}$ is vinylbenzyl and R$^{23}$ is vinylbenzyl;

the compound of Formula (IIa) wherein R$^{22}$ is 3-allyloxybenzyl and R$^{23}$ is 3-hydroxybenzyl;

the compound of Formula (IIa) wherein R$^{22}$ is 2-pyridinylmethyl and R$^{23}$ is 3-pyridinylmethyl;

the compound of Formula (IIa) wherein R$^{22}$ is 2-naphthylmethyl and R$^{23}$ is 4-fluorobenzyl;

the compound of Formula (IIa) wherein R$^{22}$ is 4-hydroxybenzyl and R$^{23}$ is 4-hydroxybenzyl;

the compound of Formula (IIa) wherein $R^{22}$ is 3-hydroxymethylbenzyl and $R^{23}$ is 3-hydroxymethylbenzyl;

the compound of Formula (IIa) wherein $R^{22}$ is 3-carbomethoxybenzyl and $R^{23}$ is 3-carbomethoxybenzyl;

the compound of Formula (IIa) wherein $R^{22}$ is 4-hydroxymethylbenzyl and $R^{23}$ is 4-hydroxymethylbenzyl;

the compound of Formula (IIa) wherein $R^{22}$ is 3-formylbenzyl and $R^{23}$ is 3-formylbenzyl;

the compound of Formula (IIa) wherein $R^{22}$ is 4-cyanobenzyl and $R^{23}$ is 4-cyanobenzyl;

the compound of Formula (IIa) wherein $R^{22}$ is 4-formylbenzyl and $R^{23}$ is 4-formylbenzyl;

the compound of Formula (IIa) wherein $R^{22}$ is 4-hydroxybenzyl and $R^{23}$ is 2-propyl;

the compound of Formula (IIa) wherein $R^{22}$ is 3-hydroxybenzyl and $R^{23}$ is 2-propyl;

the compound of Formula (IIa) wherein $R^{22}$ is 3-carboxybenzyl and $R^{23}$ is 3-carboxybenzyl;

the compound of Formula (IIa) wherein $R^{22}$ is 3-formaldoximebenzyl and $R^{23}$ is 3-formaldoximebenzyl;

the compound of Formula (IIa) wherein $R^{22}$ is cyclopropylmethyl and $R^{23}$ is 3-hydroxybenzyl;

the compound of Formula (IIa) wherein $R^{22}$ is cyclopropylmethyl and $R^{23}$ is 4-hydroxybenzyl;

the compound of Formula (IIa) wherein $R^{22}$ is cyclobutylmethyl and $R^{23}$ is cyclobutylmethyl;

the compound of Formula (IIa) wherein $R^{22}$ is cyclopentylmethyl and $R^{23}$ is cyclopentylmethyl;

the compound of Formula (IIa) wherein $R^{22}$ is 3n-butyl and $R^{23}$ is $CH_2CH=C(CH_3)_2$;

the compound of Formula (IIa) wherein $R^{22}$ is n-butyl and $R^{23}$ is cyclopentylmethyl;

the compound of Formula (IIa) wherein $R^{22}$ is benzyl and $R^{23}$ is H;

the compound of Formula (IIa) wherein $R^{22}$ is 3-fluorobenzyl and $R^{23}$ is 3-fluorobenzyl;

the compound of Formula (IIa) wherein $R^{22}$ is 3-methoxybenzyl and $R^{23}$ is 3-methoxybenzyl;

the compound of Formula (IIa) wherein $R^{22}$ is 3,4-difluorobenzyl and $R^{23}$ is 3,4-difluorobenzyl;

the compound of Formula (IIa) wherein $R^{22}$ is 4-methylbenzyl and $R^{23}$ is 4-methylbenzyl;

the compound of Formula (IIa) wherein $R^{22}$ is 4-chlorobenzyl and $R^{23}$ is 4-chlorobenzyl;

the compound of Formula (IIa) wherein $R^{22}$ is cyclopropylmethyl and $R^{23}$ is 4-fluorobenzyl;

the compound of Formula (IIa) wherein $R^{22}$ is 3-chlorobenzyl and $R^{23}$ is 3-chlorobenzyl;

the compound of Formula (IIa) wherein $R^{22}$ is 3-nitrobenzyl and $R^{23}$ is 3-nitrobenzyl;

the compound of Formula (IIa) wherein $R^{22}$ is 3-methylbenzyl and $R^{23}$ is 3-methylbenzyl;

the compound of Formula (IIa) wherein $R^{22}$ is 3-bromobenzyl and $R^{23}$ is 3-bromobenzyl;

the compound of Formula (IIa) wherein $R^{22}$ is 4-fluorobenzyl and $R^{23}$ is H;

the compound of Formula (IIa) wherein $R^{22}$ is cyclopropylmethyl and $R^{23}$ is 3-chlorobenzyl;

the compound of Formula (IIa) wherein $R^{22}$ is 3-aminobenzyl and $R^{23}$ is 3-aminobenzyl;

the compound of Formula (IIa) wherein $R^{22}$ is 3-nitrobenzyl and $R^{23}$ is H;

the compound of Formula (IIa) wherein $R^{22}$ is 3-(NHCHO) benzyl and $R^{23}$ is 3-(NHCHO)benzyl;

the compound of Formula (IIa) wherein $R^{22}$ is 3-(NHCOCH$_3$)benzyl and $R^{23}$ is 3-(NHCOCH$_3$)benzyl;

the compound of Formula (IIa) wherein $R^{22}$ is 3,4-dihydroxybenzyl and $R^{23}$ is 3,4-dihydroxybenzyl;

the compound of Formula (IIa) wherein $R^{22}$ is 3-formaldoximebenzyl and $R^{23}$ is 3-(N-hydroxy)aminomethylbenzyl;

the compound of Formula (IIa) wherein $R^{22}$ is 3-(N-hydroxy)aminomethylbenzyl and $R^{23}$ is 3-(N-hydroxy)aminomethylbenzyl;

the compound of Formula (IIa) wherein $R^{22}$ is 3-(CH$_3$OC(=O)O—)benzyl and $R^{23}$ is 3-(CH$_3$OC(=O)O—)benzyl;

the compound of Formula (IIa) wherein $R^{22}$ is 3-(1-hydroxyethyl)benzyl and $R^{23}$ is 3-(1-hydroxyethyl)benzyl;

the compound of Formula (IIa) wherein $R^{22}$ is 3-(HOCH$_2$CH$_2$N=CH)benzyl and $R^{23}$ is 3-(HOCH$_2$CH$_2$N=CH)benzyl;

the compound of Formula (IIa) wherein $R^{22}$ is 3-(HOCH$_2$CH$_2$N=CH)benzyl and $R^{23}$ is 3-(2-oxazolidinyl)benzyl;

the compound of Formula (IIa) wherein $R^{22}$ is 3-(C$_6$H$_5$CH$_2$NHC(=O)O)benzyl and $R^{23}$ is 3-(C$_6$H$_5$CH$_2$NHC(=O)O)benzyl;

the compound of Formula (IIa) wherein $R^{22}$ is 3-(CH$_3$NHC(=O)O)benzyl and $R^{23}$ is 3-(CH$_3$NHC(=O)O)benzyl;

the compound of Formula (IIa) wherein $R^{22}$ is 3-(HOCH$_2$CC)benzyl and $R^{23}$ is 3-bromobenzyl;

the compound of Formula (IIa) wherein $R^{22}$ is 3-acetylbenzyl and $R^{23}$ is 3-bromobenzyl;

the compound of Formula (IIa) wherein $R^{22}$ is 3-acetylbenzyl and $R^{23}$ is 3-acetylbenzyl;

the compound of Formula (IIa) wherein $R^{22}$ is 3-(CH$_3$C(=NOH)benzyl and $R^{23}$ is 3-(CH$_3$C(=NOH))benzyl;

the compound of Formula (IIa) wherein $R^{22}$ is 3-(1hydroxyethyl)benzyl and $R^{23}$ is 3-bromobenzyl;

the compound of Formula (IIa) wherein $R^{22}$ is 3-(chloromethyl)benzyl and $R^{23}$ is 3-(chloromethyl)benzyl;

the compound of Formula (IIa) wherein $R^{22}$ is 3-(5-tetrazolyl)benzyl and $R^{23}$ is cyclopropylmethyl;

the compound of Formula (IIa) wherein $R^{22}$ is 3-cyanobenzyl and $R^{23}$ is 3-formylbenzyl;

the compound of Formula (IIa) wherein $R^{22}$ is 4-acetoxybenzyl and $R^{23}$ is 4-hydroxybenzyl;

the compound of Formula (IIa) wherein $R^{22}$ is 3-aminocarbonylbenzyl and $R^{23}$ is 3-aminocarbonylbenzyl;

the compound of Formula (IIa) wherein $R^{22}$ is 3-(H$_2$NCOCH$_2$)benzyl and $R^{23}$ is 3-(H$_2$NCOCH$_2$O)benzyl;

the compound of Formula (IIa) wherein $R^{22}$ is 3-hydroxybenzyl and $R^{23}$ is H;

the compound of Formula (IIa) wherein $R^{22}$ is 3-methylbenzyl and $R^{23}$ is 3-hydroxybenzyl;

the compound of Formula (IIa) wherein $R^{22}$ is 2-naphthylmethyl and $R^{23}$ is 3-hydroxybenzyl;

the compound of Formula (IIa) wherein $R^{22}$ is 3-($H_2$NNHC(=O))-benzyl and $R^{23}$ is 3-($H_2$NNHC(=O))-benzyl;

the compound of Formula (IIa) wherein $R^{22}$ is 4-($H_2$NNHC(=O))-benzyl and $R^{23}$ is 4-($H_2$NNHC(=O))-benzyl;

the compound of Formula (IIa) wherein $R^{22}$ is 4-hydroxymethylbenzyl and $R^{23}$ is 3-hydroxybenzyl;

the compound of Formula (IIa) wherein $R^{22}$ is 3-($H_2$NC(=O)NHN=CH)-benzyl and $R^{23}$ is 3-($H_2$NC(=O)NHN=CH)—benzyl;

the compound of Formula (IIa) wherein $R^{22}$ is 3-[(N-methoxy)aminocarbonyl]-benzyl and $R^{23}$ is 3-[(N-methoxy)aminocarbonyl]-benzyl:

the compound of Formula (IIa) wherein $R^{22}$ is 4-[(N-methoxy)aminocarbonyl]-benzyl and $R^{23}$ is 4-[(N-methoxy)aminocarbonyl]-benzyl;

the compound of Formula (IIa) wherein $R^{22}$ is 3-(HOCH$_2$CH(OH)CH$_2$O)benzyl and $R^{23}$ is 3-(HOCH$_2$CH(OH)CH$_2$O)benzyl;

the compound of Formula (IIa) wherein $R^{22}$ is 3-(2-hydroxyethoxy)benzyl and $R^{23}$ is 3-(2hydroxyethoxy)benzyl;

the compound of Formula (IIa) wherein $R^{22}$ is 3-(1,2-dihydroxyethyl)benzyl and $R^{23}$ is 4-(1,2-dihydroxyethyl)benzyl;

the compound of Formula (IIa) wherein $R^{22}$ is 3-aminocarbonylbenzyl and $R^{23}$ is 3-($H_2$NC(=NH))benzyl;

the compound of Formula (IIa) wherein $R^{22}$ is 4-hydroxybenzyl and $R^{23}$ is 3-formyl-4-hydroxybenzyl;

the compound of Formula (IIa) wherein $R^{22}$ is 3-carbomethoxybenzyl and $R^{23}$ is 3-(N-methylaminocarbonyl)benzyl;

the compound of Formula (IIa) wherein $R^{22}$ is 3-(N-methylaminocarbonyl)benzyl and $R^{23}$ is 3-(N-methylaminocarbonyl)benzyl;

the compound of Formula (IIa) wherein $R^{22}$ is benzyl and $R^{23}$ is 3-hydroxybenzyl;

the compound of Formula (IIa) wherein $R^{22}$ is 2-naphthylmethyl and $R^{23}$ is 4-hydroxymethylbenzyl;

the compound of Formula (IIa) wherein $R^{22}$ is 3-(1,2-dihydroxyethyl)benzyl and $R^{23}$ is 3-(1,2-dihydroxyethyl)benzyl;

the compound of Formula (IIa) wherein $R^{22}$ is 4-(1,2-dihydroxyethyl)benzyl and $R^{23}$ is 4-(1,2-dihydroxyethyl)benzyl;

the compound of Formula (IIa) wherein $R^{22}$ is 3-hydroxymethylbenzyl and $R^{23}$ is 3-(N-methylaminocarbonyl)benzyl;

the compound of Formula (IIa) wherein $R^{22}$ is 4-hydroxymethylbenzyl and $R^{23}$ is hydrogen;

the compound of Formula (IIa) wherein $R^{22}$ is 3-(boronic acid)benzyl and $R^{23}$ is 3-(boronic acid)benzyl;

the compound of Formula (IIa) wherein $R^{22}$ is 3-nitrobenzyl and $R^{23}$ is 3-benzyloxybenzyl;

the compound of Formula (IIa) wherein $R^{22}$ is 3-aminobenzyl and $R^{23}$ is 3-hydroxybenzyl;

the compound of Formula (IIa) wherein $R^{22}$ is 3-(N-ethylaminocarbonyl)benzyl and $R^{23}$ is 3-(N-ethylaminocarbonyl)benzyl;

the compound of Formula (IIa) wherein $R^{22}$ is 3-carbomethoxybenzyl and $R^{23}$ is 3-(N,N-diethylaminocarbonyl)benzyl;

the compound of Formula (IIa) wherein $R^{22}$ is 3-carbomethoxybenzyl and $R^{23}$ is 3-(N-ethylaminocarbonyl)benzyl;

the compound of Formula (IIa) wherein $R^{22}$ is 6-hydroxy-1-hexyl and $R^{23}$ is hydrogen;

the compound of Formula (IIa) wherein $R^{22}$ is 6-hydroxy-1-hexyl and $R^{23}$ is 6-hydroxy-1-hexyl;

the compound of Formula (IIa) wherein $R^{22}$ is cyclopropylmethyl and $R^{23}$ is 6-hydroxy-1-hexyl;

the compound of Formula (IIa) wherein $R^{22}$ is 5-carboxy-1-pentyl and $R^{23}$ is 5-carboxy-1-pentyl;

the compound of Formula (IIa) wherein $R^{22}$ is 3-iodobenzyl and $R^{23}$ is 3-iodobenzyl;

the compound of Formula (IIa) wherein $R^{22}$ is benzyl and $R^{23}$ is 2-(hydroxymethyl)-cyclopropylmethyl;

the compound of Formula (IIa) wherein $R^{22}$ is 3-(thiomethyl)benzyl and $R^{23}$ is 3-(thiomethyl)benzyl;

the compound of Formula (IIa) wherein $R^{22}$ is 3-(methylsulfonyl)benzyl and $R^{23}$ is 3-(methylsulfonyl)benzyl;

the compound of Formula (IIa) wherein $R^{22}$ is 6-hexenyl and $R^{23}$ is 6-hexenyl;

the compound of Formula (IIa) wherein $R^{22}$ is 6-bromo-5-hydroxy-1-hexyl and $R^{23}$ is 6-bromo-5-hydroxy-1hexyl;

the compound of Formula (IIa) wherein $R^{22}$ is 5-hydroxy-1-pentyl and $R^{23}$ is 5-hydroxy-1-pentyl;

the compound of Formula (IIa) wherein $R^{22}$ is 3-aminobenzyl and $R^{23}$ is 4-hydroxymethylbenzyl;

the compound of Formula (IIa) wherein $R^{22}$ is 3-($H_2$NC(=O)NH)benzyl and $R^{23}$ is 3-($H_2$NC(=O)NH)benzyl;

the compound of Formula (IIa) wherein $R^{22}$ is 3-(N-methylamino)benzyl and $R^{23}$ is 3-(N-methylamino)benzyl;

the compound of Formula (IIa) wherein $R^{22}$ is cyclopropylmethyl and $R^{23}$ is 3-aminobenzyl;

the compound of Formula (IIa) wherein $R^{22}$ is cyclopropylmethyl and $R^{23}$ is 3-nitrobenzyl;

the compound of Formula (IIa) wherein $R^{22}$ is 3-(N,N-dimethylamino)benzyl and $R^{23}$ is 3-(N,N-dimethylamino)benzyl;

the compound of Formula (IIa) wherein $R^{22}$ is 3-nitrobenzyl and $R^{23}$ is 4-hydroxymethylbenzyl;

the compound of Formula (IIa) wherein $R^{22}$ is 3-aminobenzyl and $R^{23}$ is 3-(CH$_3$NHC(=O)NH)benzyl;

the compound of Formula (IIa) wherein $R^{22}$ is 3-(CH$_3$NHC(=O)NH)benzyl and $R^{23}$ is 3-(CH$_3$NHC(=O)NH)benzyl;

the compound of Formula (IIa) wherein $R^{22}$ is 3-(N-methylamino)benzyl and $R^{23}$ is 4-hydroxymethylbenzyl;

the compound of Formula (IIa) wherein $R^{22}$ is 3-(N,N-dimethyaminoglycyl)amino)benzyl and $R^{23}$ is 3-((N,N-dimethylaminoglycyl)amino)benzyl;

the compound of Formula (IIa) wherein $R^{22}$ is 3-((N-methylaminoglycyl)amino)benzyl and $R^{23}$ is 3-((N-methylaminoglycyl)amino)benzyl;

the compound of Formula (IIa) wherein $R^{22}$ is 3-((N,N-dimethylaminoglycyl)amino)benzyl and $R^{23}$ is 4-hydroxymethylbenzyl;

the compound of Formula (IIa) wherein $R^{22}$ is 3-((N-phenylmethoxycarbonylaminoglycyl)amino)benzyl and R²³ is 3-((N-phenylmethoxycarbonylaminoglycyl)amino)benzyl;

the compound of Formula (IIa) wherein R²² is 3-(glycylamino)benzyl and R²³ is 3-(glycylamino)benzyl;

the compound of Formula (IIa) wherein R²² is 3-(glycylamino)benzyl and R²³ is 4-hydroxymethylbenzyl;

the compound of Formula (IIa) wherein R²² is 3-((N-phenylmethoxycarbonylamino-L-alanyl)amino)benzyl and R²³ is 3-((N-phenylmethoxycarbonylamino-L-alanyl)amino)benzyl;

the compound of Formula (IIa) wherein R²² is 3-((N-phenylmethoxycarbonylamino-L-phenylalanyl)amino)benzyl and R²³ is 3-((N-phenylmethoxycarbonylamino-L-phenylalanyl)amino)benzyl;

the compound of Formula (IIa) wherein R²² is 3-(L-alanyl)amino)benzyl and R²³ is 3-(L-alanyl)amino)benzyl;

the compound of Formula (IIa) wherein R²² is 3-(L-phenylalanyl) amino)benzyl and R²³ is 3-(L-phenylalanyl)amino)benzyl;

the compound of Formula (IIa) wherein R²² is 5-hydroxy-1-pentyl and R²³ is hydrogen;

the compound of Formula (IIa) wherein R²² is 5-hydroxy-1-pentyl and R²³ is 2-naphthylmethyl;

the compound of Formula (IIa) wherein R²² is 5-hydroxy-1-pentyl and R²³ is benzyl;

the compound of Formula (IIa) wherein R²² is 5-hydroxy-1-pentyl and R²³ is 4-hydroxymethylbenzyl;

the compound of Formula (IIa) wherein R²² is 6-hydroxy-1-hexyl and R²³ is 2-naphthylmethyl;

the compound of Formula (IIa) wherein R²² is 5-hydroxy-1-pentyl and R²³ is 3-hydroxybenzyl;

the compound of Formula (IIa) wherein R²² is 5-hydroxy-1-pentyl and R²³ is(5-methylsulfonyl)-1-pentyl;

the compound of Formula (IIa) wherein R²² is 5-hydroxy-1-pentyl and R²³ is 5-($CH_3S(O)$)-1-pentyl;

the compound of Formula (IIa) wherein R²² is 5-hydroxy-1-pentyl and R²³ is cyclopropylmethyl;

the compound of Formula (IIa) wherein R²² is 5-hydroxy-1-pentyl and R²³ is 5-methoxy-1-pentyl;

the compound of Formula (IIa) wherein R²² is 5-hydroxy-1-pentyl and R²³ is 3-cyanobenzyl;

the compound of Formula (IIa) wherein R²² is 5-hydroxy-1-pentyl and R²³ is 3-carboethoxybenzyl;

the compound of Formula (IIa) wherein R²² is 4-hydroxy-1-hexyl and R²³ is 4-hydroxy-1-hexyl;

the compound of Formula (IIa) wherein R²² is 4-hydroxy-1-hexyl and R²³ is 2-naphthylmethyl;

the compound of Formula (IIa) wherein R²² is 4-oxime-1-hexyl and R²³ is 4-oxime-1-hexyl;

the compound of Formula (IIa) wherein R²² is 5-hydroxy-1-pentyl and R²³ is 3-hydroxymethylbenzyl;

the compound of Formula (IIa) wherein R²² is amino-1-hexyl and R²³ is 4-hydroxymethylbenzyl;

the compound of Formula (IIa) wherein R²² is 3-(N,N-diethylaminocarbonyl)benzyl and R²³ is 3-(N,N-diethylaminocarbonyl)benzyl;

the compound of Formula (IIa) wherein R²² is 3-carbomethoxybenzyl and R²³ is 3-(N,N-diethylaminocarbonyl)benzyl;

the compound of Formula (IIa) wherein R²² is 3-carbomethoxybenzyl and R²³ is 3-(N-ethylaminocarbonyl)benzyl;

the compound of Formula (IIa) wherein R²² is 3-hydroxymethylbenzyl and R²³ is hydrogen;

the compound of Formula (IIa) wherein R²² is 3-hydroxymethylbenzyl and R²³ is 3-(N,N-diethylaminocarbonyl)benzyl;

the compound of Formula (IIa) wherein R²² is 3-hydroxymethylbenzyl and R²³ is 3-(N-ethylaminocarbonyl)benzyl;

the compound of Formula (IIa) wherein R²² is 3-(N-propylaminocarbonyl)benzyl and R²³ is 3-(N-propylaminocarbonyl)benzyl;

the compound of Formula (IIa) wherein R²² is 3-($HO_2C$)benzyl and R²³ is 3-(N-isopropylaminocarbonyl)benzyl;

the compound of Formula (IIa) wherein R²² is 3-($HO_2C$)benzyl and R²³ is 3-(N-propylaminocarbonyl)benzyl;

the compound of Formula (IIa) wherein R²² is 3-($HO_2C$)benzyl and R²³ is benzyl;

the compound of Formula (IIa) wherein R²² is 3-($HO_2C$)benzyl and R²³ is cyclopropylmethyl;

the compound of Formula (IIa) wherein R²² is 4-hydroxymethylbenzyl and R²³ is 3-($HO_2C$)benzyl;

the compound of Formula (IIa) wherein R²² is 3-hydroxymethylbenzyl and R²³ is 3-pyridinylmethyl;

the compound of Formula (IIa) wherein R²² is 4-hydroxymethylbenzyl and R²³ is 3-aminocarbonylbenzyl;

the compound of Formula (IIa) wherein R²² is 3-aminobenzyl and R²³ is 2-naphthylmethyl;

the compound of Formula (IIa) wherein R²² is cyclopropylmethyl and R²³ is 3-aminocarbonylbenzyl;

the compound of Formula (IIa) wherein R²² is 3-aminocarbonylbenzyl and R²³ is hydrogen;

the compound of Formula (IIa) wherein R²² is 3-hydroxymethylbenzyl and R²³ is 3-(N-ethylaminocarbonyl)benzyl;

the compound of Formula (IIa) wherein R²² is 3-hydroxymethylbenzyl and R²³ is 3-(N-methylamino)benzyl;

the compound of Formula (IIa) wherein R²² is 3-(N-methylamino)benzyl and R²³ is 2-naphthylmethyl;

the compound of Formula (IIa) wherein R²² is 4-formylbenzyl and R²³ is 4-hydroxymethylbenzyl;

the compound of Formula (IIa) wherein R²² is 3-(1-hydroxy-1-ethyl)benzyl and R²³ is 3-(1-hydroxyethyl)benzyl;

the compound of Formula (IIa) wherein R²² is 3-pyridinylmethyl and R²³ is 4-hydroxymethylbenzyl;

the compound of Formula (IIa) wherein R²² is 3-(N-imidazolylmethyl)benzyl and R²³ is 3-(N-imidazolylmethyl)benzyl;

the compound of Formula (IIa) wherein R²² is 3-(2,2-dimethyl-1-propionyl)benzyl and R²³ is 3-(2,2-dimethyl-1-propionyl)benzyl;

the compound of Formula (IIa) wherein R²² is 3-(2,2,2-trifluoro-1-hydroxyethyl)benzyl and R²³ is 3-(2,2,2-trifluoro-1-hydroxyethyl)benzyl;

the compound of Formula (IIa) wherein R²² is 3-(2-imidazolyl-C(=O)benzyl and R²³ is 3-(2-imidazolyl-C(=O))benzyl;

the compound of Formula (IIa) wherein R²² is 3-(3-hydroxy-1-propyn-1-yl)benzyl and R²³ is 3-(3-hydroxy-1-propyn-1-yl)benzyl;

the compound of Formula (IIa) wherein $R^{22}$ is 3-(2,2,2-trifluoroacetyl)benzyl and $R^{23}$ is 3-(2,2,2-trifluoroacetyl)benzyl;

the compound of Formula (IIa) wherein $R^{22}$ is 3-propionylbenzyl and $R^{23}$ is 3-propionylbenzyl;

the compound of Formula (IIa) wherein $R^{22}$ is 3-(4-pyrazolyl)benzyl and $R^{23}$ is 3-(4-pyrazolyl)benzyl;

the compound of Formula (IIa) wherein $R^{22}$ is 3-($CH_3CH_2C(=N-OH$)benzyl and $R^{23}$ is 3-($CH_3CH_2C(=N-OH$))benzyl;

the compound of Formula (IIa) wherein $R^{22}$ is 3-sulfonamidobenzyl and $R^{23}$ is 3-sulfonamidobenzyl;

the compound of Formula (IIa) wherein $R^{22}$ is 3-($CF_3CH_2C(=N-OH$)benzyl and $R^{23}$ is 3-($CF_3CH_2C(=NO-H$))benzyl;

the compound of Formula (IIa) wherein $R^{22}$ is 4-fluoromethylbenzyl and $R^{23}$ is 4-fluoromethylbenzyl;

the compound of Formula (IIa) wherein $R^{22}$ is 4-(1-hydroxyethyl)benzyl and $R^{23}$ is 4-(1-hydroxyethyl)benzyl;

the compound of Formula (IIa) wherein $R^{22}$ is 3-(5-methyl-1,2,3-oxadiazolyl)benzyl and $R^{23}$ is 3-(5-methyl-1,2,3-oxadiazolyl)benzyl;

[8] Specifically preferred compounds of component(i) of the invention are compounds of Formula (IIaa):

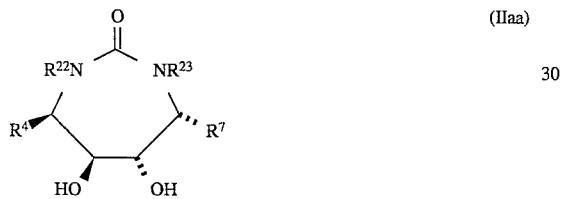

or a pharmaceutically acceptable salt or prodrug form thereof wherein:

$R^4$ and $R^7$ are independently selected from: benzyl, fluorobenzyl, pyrrolylmethyl, methoxybenzyl, isobutyl, nitrobenzyl or aminobenzyl;

$R^{22}$ and $R^{23}$ are independently selected from:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminom-ethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl )benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl)benzyl, ($CF_3C(=NOH)$)-benzyl, (N-methylglycyl)aminobenzyl, ((4-morpholino)ethyl )aminocarbonylbenzyl, (N,N-dimethylaminoethyl )aminocarbonylbenzyl, (N,N-diethylaminoethyl )aminocarbonylbenzyl, (4-methylpiperazin-1-yl-ethyl )aminocarbonylbenzyl, (benzyl-NHC(=O)O)benzyl, ($CH_3NHC(=O)O$)benzyl, ($NH_2C(=O)CH_2O$)benzyl, ($NH_2C(=NH)$)benzyl, ((N-phenylmethoxycarbonyl)glycylamino)benzyl, (imidazolylmethyl)benzyl, (($CH_3)_3C-C(=O)$))benzyl, (N-methyl-N-ethylaminoethyl)aminocarbonylbenzyl, (pyrrolidinylethyl)aminocarbonylbenzyl, (piperidinylethyl)aminocarbonylbenzyl.

[9] Specifically preferred compounds of component (i) of the invention are compounds of Formula (IIaa):

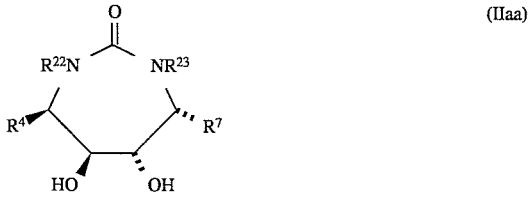

selected from the group consisting of:

the compound of Formula (IIaa) wherein $R^4$ and $R^7$ are isobutyl, $R^{22}$ and $R^{23}$ are cyclopropylmethyl;

the compound of Formula (IIaa) wherein $R^4$ and $R^7$ are isobutyl, $R^{22}$ and $R^{23}$ are allyl;

the compound of Formula (IIaa) wherein $R^4$ is 4-nitrobenzyl, $R^7$ is 2-nitrobenzyl, $R^{22}$ and $R^{23}$ are cyclopropylmethyl;

the compound of Formula (IIaa) wherein $R^4$ and $R^7$ are 4-nitrobenzyl, $R^{22}$ and $R^{23}$ are cyclopropylmethyl;

the compound of Formula (IIaa) wherein $R^4$ is 4-nitrobenzyl, $R^7$ is 2-nitrobenzyl, $R^{22}$ and $R^{23}$ are n-butyl;

the compound of Formula (IIaa) wherein $R^4$ is 4-aminobenzyl, $R^7$ is 2-aminobenzyl, $R^{22}$ and $R^{23}$ are cyclopropylmethyl;

the compound of Formula (IIaa) wherein $R^4$ and $R^7$ are 4-fluorobenzyl, $R^{22}$ and $R^{23}$ are 3-hydroxybenzyl;

the compound of Formula (IIaa) wherein $R^4$ and $R^7$ are 4-fluorobenzyl, $R^{22}$ and $R^{23}$ are cyclopropylmethyl;

the compound of Formula (IIaa) wherein $R^4$ and $R^7$ are 4-fluorobenzyl, $R^{22}$ and $R^{23}$ are 4-hydroxymethylbenzyl;

the compound of Formula (IIaa) wherein $R^4$ and $R^7$ are 4-fluorobenzyl, $R^{22}$ and $R^{23}$ are 3-aminocarbonylbenzyl;

the compound of Formula (IIaa) wherein $R^4$ and $R^7$ are 4-fluorobenzyl, $R^{22}$ and $R^{23}$ are 3-acetylbenzyl;

the compound of Formula (IIaa) wherein $R^4$ and $R^7$ are 4-fluorobenzyl, $R^{22}$ and $R^{23}$ are 3-butyrylbenzyl;

the compound of Formula (IIaa) wherein $R^4$ and $R^7$ are 4-fluorobenzyl, $R^{22}$ and $R^{23}$ are 3-hydroxymethylbenzyl;

the compound of Formula (IIaa) wherein $R^4$ and $R^7$ are 4-fluorobenzyl, $R^{22}$ and $R^{23}$ are 3-($CH_3C(=N-OH)$)benzyl;

the compound of Formula (IIaa) wherein $R^4$ and $R^7$ are 3-methoxybenzyl, $R^{22}$ and $R^{23}$ are benzyl.

[10] Also specifically preferred compounds of component (i) of the invention are compounds of Formula (IIb):

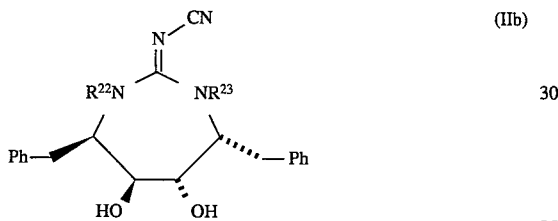

or a pharmaceutically acceptable salt or prodrug form thereof wherein:

$R^{22}$ and $R^{23}$ are independently selected from the group consisting of: hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyloxazolinylmethyl, naphthylmethyl, methyloxazolinylmethyl, vinyloxyethyl, pentafluorobenzyl, quinolinylmethyl, carboxybenzyl, chlorothienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzylformaldoxime)benzyl, (O-methylformaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxyaminobenzyl, phenylmethyl-boronic acid, N-hydroxyaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl)phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)-benzyl, (trifluorohydroxyethyl)benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$)benzyl, ($NH_2C(=O)CH_2O$)benzyl, ($NH_2C(=NH)$)benzyl, ((N-phenylmethoxycarbonyl)glycylamino)benzyl, (imidazolylmethyl)benzyl, (($CH_3)_3C-C(=O)$))benzyl, (N-methyl-N-ethylaminoethyl)aminocarbonylbenzyl, (pyrrolidinylethyl)aminocarbonylbenzyl, (piperidinylethyl)aminocarbonylbenzyl.

[11] Specifically preferred compounds of component (i) of the invent ion are compounds of Formula (IIb):

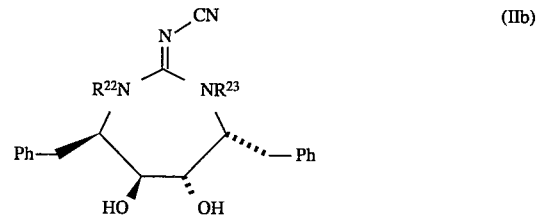

or a salt thereof, selected from the group consisting of:

the compound of Formula (IIb) wherein $R^{22}$ is 4-hydroxybenzyl and $R^{23}$ is 4-hydroxybenzyl;

the compound of Formula (IIb) wherein $R^{22}$ is cyclopentylmethyl and $R^{23}$ is cyclopentylmethyl;

the compound of Formula (IIb) wherein $R^{22}$ is n-butyl and $R^{23}$ is n-butyl;

the compound of Formula (IIb) wherein $R^{22}$ is 3-hydroxybenzyl and $R^{23}$ is 3-hydroxybenzyl;

the compound of Formula (IIb) wherein $R^{22}$ is 3-aminobenzyl and $R^{23}$ is 3-aminobenzyl;

the compound of Formula (IIb) wherein $R^{22}$ is cyclohexylmethyl and $R^{23}$ is cyclohexylmethyl;

the compound of Formula (IIb) wherein $R^{22}$ is cyclobutylmethyl and $R^{23}$ is cyclobutylmethyl;

the compound of Formula (IIb) wherein $R^{22}$ is 3-hydroxymethylbenzyl and $R^{23}$ is 3-hydroxymethylbenzyl;

the compound of Formula (IIb) wherein $R^{22}$ is 3-formylbenzyl and $R^{23}$ is 3-formylbenzyl;

the compound of Formula (IIb) wherein $R^{22}$ is 3-formaldoximebenzyl and $R^{23}$ is 3-formaldoximebenzyl;

[12] Specifically preferred compounds of component (i) of the invention are compounds of Formula (Ibb):

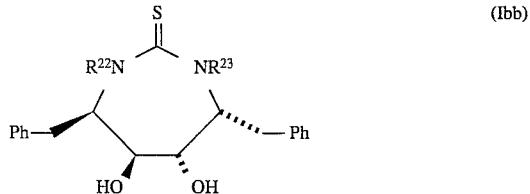

or a pharmaceutically acceptable salt or prodrug form thereof wherein:

$R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl(oxazolidinyl)- benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl carbonyl)alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)benzyl, (trifluorohydroxyethyl)benzyl, ($CF_3C(=NOH)$)-benzyl, (N-methylglycyl)aminobenzyl, ((4-morpholino)ethyl )aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$)benzyl, ($NH_2C(=O)CH_2O$)benzyl, ($NH_2C(=NH)$)benzyl, ((N-phenylmethoxycarbonyl)glycylamino)benzyl, (imidazolylmethyl)benzyl, (($(CH_3)_3C$—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

[13] Specifically preferred compounds of component(i)of the invention are compounds of Formula (Ibb):

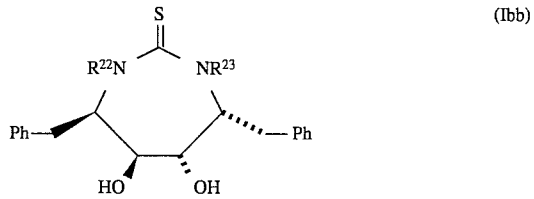

or a salt thereof, selected from the group consisting of:

the compound of Formula (Ibb) wherein $R^{22}$ is benzyl and $R^{23}$ is hydrogen;

the compound of Formula (Ibb) wherein $R^{22}$ is cyclopropylmethyl and $R^{23}$ is cyclopropylmethyl;

the compound of Formula (Ibb) wherein $R^{22}$ is benzyl and $R^{23}$ is benzyl;

the compound of Formula (Ibb) wherein $R^{22}$ is m-hydroxybenzyl and $R^{23}$ is m-hydroxybenzyl;

[14] Specifically preferred compounds of component(i)of the invention are compounds of Formula (Ic):

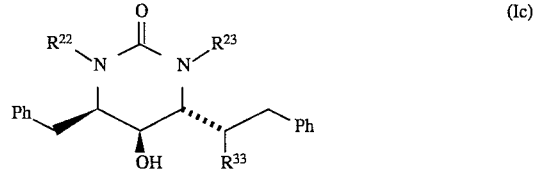

or a pharmaceutically acceptable salt or prodrug form thereof wherein:

$R^{33}$ is OH, halogen, H, $N_3$ or can alternatively be taken together with $R^{23}$ to form a direct bond;

wherein $R^{22}$ and $R^{23}$ are independently selected from the group consisting of:

hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)benzyl, (trifluorohydroxyethyl)benzyl, ($CF_3C(=NOH)$)-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, ($CH_3NHC(=O)O$)benzyl, ($NH_2C(=O)CH_2O$)benzyl, ($NH_2C(=NH)$)benzyl, ((N-phenylmethoxycarbonyl)glycylamino)benzyl, (imidazolylmethyl)benzyl, (($CH_3)_3C-C(=O)$)benzyl, (N-methyl-N-ethylaminoethyl)aminocarbonylbenzyl, (pyrrolidinylethyl)aminocarbonylbenzyl, (piperidinylethyl)aminocarbonylbenzyl.

[15] Specifically preferred compounds of component(i) of the invention are compounds of Formula (Ic):

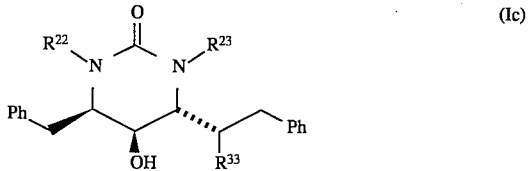

selected from the group consisting of:
the compound of Formula (Ic) wherein $R^{22}$ is 3-hydroxybenzyl, $R^{23}$ is 3-hydroxybenzyl and $R^{33}$ is hydrogen;
the compound of Formula (Ic) wherein $R^{22}$ is 3-acetylbenzyl, $R^{23}$ is 3-acetylbenzyl and $R^{33}$ is hydrogen;
the compound of Formula (Ic) wherein $R^{22}$ is 3-hydroxymethylbenzyl, $R^{23}$ is 3-hydroxymethylbenzyl and $R^{33}$ is hydrogen.

[16] Specifically preferred compounds of component(i) of the invention are compounds of Formula (IId):

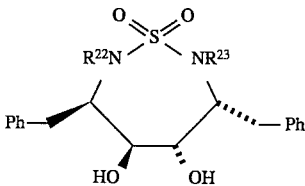

or a pharmaceutically acceptable salt or prodrug form thereof wherein:

$R^{22}$ and $R^{23}$ are independently selected from the group consisting of:
hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, ($H_2NC(=O)$)-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, ($CH_3O_2CO$)-benzyl, ($HOCH_2CH_2N=CH$)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, ($CH_3C(=NOH)$)-benzyl, ($H_2NNHC(=O)$)-benzyl, ($H_2NC(=O)NHN=CH$)-benzyl, ($CH_3ONHC(=O)$)-benzyl, ($HONHC(=O)$)-benzyl, ($CH_3NHC(=O)$)-benzyl, N,N-dimethylaminocarbonylbenzyl, ($HOCH_2CH(OH)CH_2O$)-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, ($CH_3CH_2NHC(=O)$)-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))benzyl, (pyridylmethylaminocarbonyl)benzyl, (oxadiazolidinonyl)benzyl, trifluoroacetylbenzyl, (pyrazolyl)benzyl, ($H_2NSO_2$)-benzyl, dihydroxyethylbenzyl, (MeHNC(=O)NH)-benzyl, ($H_2NC(=O)NH$)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, ($CH_3CH_2C(=NOH)$)benzyl, (trifluorohydroxyethyl)benzyl, ($CF_3C(=NOH)$)-benzyl, (N-methylglycyl)aminobenzyl, ((4-morpholino)ethyl )aminocarbonylbenzyl, (N,N-dimethylaminoethyl)aminocarbonylbenzyl, (N,N-diethylaminoethyl)aminocarbonylbenzyl, (4-methylpiperazin-1-ylethyl )aminocarbonylbenzyl, (benzyl-NHC(=O)O)benzyl, ($CH_3NHC(=O)O$)benzyl, ($NH_2C(=O)CH_2O$)benzyl, ($NH_2C(=NH)$)benzyl, ((N-phenylmethoxycarbonyl)glycylamino)benzyl, (imidazolylmethyl)benzyl, (($CH_3)_3C$-C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

[17] Specifically preferred compounds of component(i) of the invention are compounds of Formula (IId):

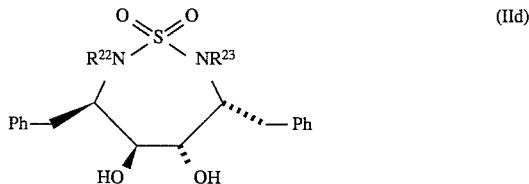

or a salt thereof, selected from the group consisting of:

the compound of Formula (IId) wherein $R^{22}$ is 4-hydroxymethylbenzyl and $R^{23}$ is 4-hydroxymethylbenzyl;

the compound of Formula (IId) wherein $R^{22}$ is 3-hydroxybenzyl and $R^{23}$ is 3-hydroxybenzyl;

the compound of Formula (IId) wherein $R^{22}$ is cyclopropylmethyl and $R^{23}$ is cyclopropylmethyl;

the compound of Formula (IId) wherein $R^{22}$ is 2-naphthylmethyl and $R^{23}$ is 2-naphthylmethyl;

the compound of Formula (IId) wherein $R^{22}$ is 4-hydroxybenzyl and $R^{23}$ is 4-hydroxybenzyl;

the compound of Formula (IId) wherein $R^{22}$ is 3-aminobenzyl and $R^{23}$ is 3-aminobenzyl;

the compound of Formula (IId) wherein $R^{22}$ is 3-hydroxymethylbenzyl and $R^{23}$ is 3-hydroxymethylbenzyl;

the compound of Formula (IId) wherein $R^{22}$ is 3-($Me_2NCH_2C(=O)NH$)-benzyl and $R^{23}$ is 3-($Me_2NCH_2C(=O)NH$)-benzyl;

the compound of Formula (IId) wherein $R^{22}$ is 3-formaldoximebenzyl and $R^{23}$ is 3-formaldoximebenzyl;

the compound of Formula (IId) wherein $R^{22}$ is 3-($CH_3C(=N-OH)$)-benzyl and $R^{23}$ is 3-($CH_3C(=N—OH)$)-benzyl.

Component (i) of the present invention includes pharmaceutical compositions comprising an therapeutically effective amount of a compound of Formulae I, II, II, IV, V or VI and a pharmaceutically acceptable carrier are useful in the method of the present invention.

Other cyclic HIV protease inhibitors of component (i) expected to be useful in the methods, pharmaceutical kits, and combination products of the present invention are described in and prepared by methods set forth in PCT International Patent Application Publication Number WO 93/07128, published Apr. 15, 1993 and in copending, commonly assigned U.S. Patent Application U.S. Ser. No. 08/047,330, filed Apr. 15, 1993.

The cyclic HIV protease inhibitors of Formula (I) useful in the method and combination products of the present invention are described in and prepared by methods set forth in PCT International Patent Application Publication Number WO 93/07128, published Apr. 15, 1993 and in copending, commonly assigned U.S. patent application U.S. Ser. No. 08/047,330, filed Apr. 15, 1993.

The preparation of AZT is described by Chu et al., Tetrahedron Letters 29, 5349 (1988). AZT is available commercially as "Retrovir®", for which the product information, including dosage and administration, is given in Physicians' Desk Reference, 46th Edition, 1992, pp. 802–808.

The preparation of DDI is described by Webb et al. in Nucleosides Nucleotides 7, 147 (1988).

The preparation of DDC is described by Horwitz et al. in J. Org. Chem. 32, 817 (1967).

The preparation of TIBO derivatives is described by Pauwels et al. in Nature 343, 470 (1990).

The preparation and RT inhibitory activity of BI-RG-587 is described by Merluzzi et al. in Science 250, 1411 (1990).

The preparation and RT inhibitory activity of L-697,661 and derivatives thereof is described by Goldman et al. in Proc. Natl. Acad. Sci. USA 88, 6863 (1991).

The preparation and RT inhibitory activity of d4T is described by Mansuri et al. in J. Med. Chem. 32, 461 (1989).

The preparation of 3TC is described by Storer et al. in Nucloesides Nucleotides 12, 225 (1993).

The disclosures of all of the references cited herein are hereby incorporated herein by reference in their entirety.

Dosage and Formulation

The cyclic HIV protease inhibitor(component (i)) and HIV RT inhibitor(component (ii)) combination treatment of the invention can be administered by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chose route of administration and standard pharmaceutical practice.

The dosage administered will, of course vary depending on ther use and known factors such as the pharmacodynamic characteristics of the particular agent, and its mode and route of administration; age, health, and weight of the recipient; nature and extent of symptoms, kind of concurrent treatment, frequency of treatment, and the effect desired.

For use in the treatment of inhibition of the replication of HIV, by way of general guidance, a daily oral dosage of active ingredient can be about 0.001 to 1000 mg/kg of body weight. Ordinarily a dose of 0.1 to 500 mg/kg per day in divided doses one to four times a day or in sustained release form is effective to obtain the desired results.

Dosage forms (compositions) suitable for administration contain about 1 milligram to 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers and methods of preparing pharmaceutical dosage forms are described in *Remington's Pharmaceutical Sciences*, Mack Publishing Company, a standard reference text in this field.

Useful pharmaceutical compositions(dosage forms) for administration of the compounds of this invention can be illustrated as follows:
Capsules A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.
Soft Gelatin Capsules A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.
Tablets A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.
Suspension An aqueous suspension is prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.
Injectable A parenteral composition suitable for administration by injection is prepared by stirring 1.5% by weight of active ingredient in 10% by volume propylene glycol and water. The solution is sterilized by commonly used techniques.

Each therapeutic agent component of this invention can independently be in any dosage form, such as those described above, and can also be administered in various ways, as described above. The component (i) and (ii) of the invention may be formulated together, in a single dosage unit (that is, combined together in one capsule, tablet, powder, or liquid, etc.) as a combination product. When component (i) and (ii) are not formulated together in a single dosage unit, the cyclic HIV protease inhibitor component (i) may be administered at the same time as the HIV RT inhibitor component (ii) or in any order; for example component (i) of this invention may be administered first, followed by administration of component (ii), or they may be administered in the reverse order. When not administered at the same time, preferably the administration of component (i) and (ii) of this invention occurs less than about one hour apart. Preferably, the route of administration of component (i) and (ii) of the invention is oral. The terms oral agent, oral inhibitor, oral compound, or the like, as used herein, denote compounds which may be orally administered. Although it is preferable that component (i) and component (ii) of the invention are both administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (i) and (ii) in this invention will be readily ascertainable by a medical practitioner skilled in the art, based upon the present disclosure. By way of general guidance, typically a daily dosage may be about 100 milligrams to about 1.5 grams of each component. By way of general guidance, when the compounds of component (i) and component (ii) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the Formulation of a combination product in which the one component is coated with a sustained and/or enteric release polymer, and the other component is also coated with a polymer such as a lowviscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (i) and a compound of component (ii), in one or more sterile containers, are also within the ambit of the present invention. Sterilization of the container may be carried out using conventional sterilization methodology well known to those skilled in the art. Component (i) and component (ii) may be in the same sterile container or in separate sterile containers. The sterile containers of materials may comprise separate containers, or one or more multi-part containers, as desired. Component (i) and component (ii), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The tests described below may be used to demonstrate the synergistic anti-HIV effect of a cyclic HIV protease inhibitor of Formula (I)administered in combination with an HIV RT inhibitor. The tests and the results described below demonstrate that a representative cyclic HIV protease inhibitor of Formula (I), Ex. No. 5U, acts synergistically with a representative HIV RT inhibitor, AZT, to inhibit HIV replication and proliferation in human cells. Ex. No. 5U is the compound of Example Number 5U described in PCT International Patent Application Publication Number WO 93/07128, published Apr. 15, 1993 and in copending, commonly assigned U.S. patent application U.S. Ser. No. 08/047,330.

HIV Yield Reduction Assay

MT-2, an HTLV-1 transformed human T-cell line, was cultured in RPMI-1640 medium supplemented with 5%(v/v) heat inactivated fetal calf serum(FCS), L-glutamine(2 mM)and gentamycin(5 µg/ml). Human immunodeficiency virus HIV-1 (RF strain)was propagated in H-9 cells in RPMI with 5% FCS. Routine testing for mycoplasma (Chen, Exp. Cell Res. 104:255–262 (1977))assured that all experiments were performed with mycoplasma-free MT-2 and H9 cells. Poly-L-lysine(Sigma)coated cell culture plates were prepared according to the method of Harada et al., Science 229:563–566 (1985). MTT, 3-(4,5-dimethylthiazol-2yl)-2,5-diphenyl-tetrazolium bromide, was obtained from Sigma.

Test compounds were dissolved in dimethylsulfoxide to 5 mg/ml and serially diluted into RPMI medium to ten times the desired final concentration. The HIV yield reduction assay was carried out using MT-2 cells and in some cases human peripheral blood mononuclear cells (PBMCs). MT-2 cells($5\times10^5$/ml)in 2.3 ml were mixed with 0.3 ml of the appropriate test compound solution and allowed to sit for 30 minutes at room temperature. Virus(approximately $5\times10^5$ plaque forming units/ml)in 0.375 ml was added to the cell and compound mixtures and incubated for one hour at 36° C. The mixtures were centrifuged at 1,000 rpm for 10 minutes and the supernatant fluids containing unattached virus were discarded. The cell pellets were suspended in fresh RPMI containing the appropriate concentrations of test compounds and placed in a 36° C., 4% $CO_2$ incubator. Virus was allowed to replicate for 3 days. Cultures were centrifuged for 10 minutes at 1,000 rpm and the supernatant fluids containing cell-free progeny virus were removed for plaque assay. The virus titers of the progeny virus produced in the presence or absence of test compounds were determined by a plaque assay similar to that described by Nakashima et al., J. Virol. Methods 26:918–930 (1989). Progeny virus suspensions were serially diluted in RPMI and 1 ml of each dilution was added to 9 ml of MT-2 cells in RPMI. Cells and virus were incubated for 3 hours at 36° C. to allow for efficient attachment of the virus to cells. Each virus and cell mixture was divided equally into two wells of a six well poly-L-lysine coated culture plate and incubated overnight at 36° C., 4% $CO_2$. Liquid and unattached cells were removed prior to the addition of 1.5 ml of RPMI with 0.75% (w/v) Seaplaque agarose(FMC Corp.) and 5% FCS. Plates were incubated for 3 days and a second RPMI/agarose overlay was added. After an additional 3 days at 36° C., 4% $CO_2$, a final overlay of phosphate-buffered saline with 0.75% Seaplaque agarose and 1 mg MTT/ml was added. The plates were incubated overnight at 36° C. Clear plaques on a purple background were counted and the number of plaque forming units of virus was calculated for each sample. The anti-viral activity of test compounds was determined by the percent reduction in the virus titer with respect to virus grown in the absence of any inhibitors.

Cytotoxicity Assay

Cell viability was determined by the metabolism of the tetrazolium dye, XTT, 3,3'-[1-[phenylamino)carbonyl]-3,4-tetrazolium]bis-(4-methoxy-6-nitrobenzene-sulfonic acid-(Sigma)(Scudiero et al., Cancer Res. 48:4827–4833 (1988)). In this assay metabolically active cells transform the tetrazolium dye, XTT, to a soluble colored formazan product. Microtiter plates (96 wells) were seeded with $1 \times 10^5$ cells/well and graded concentrations of test compounds in RPMI 1640 plus 5% FCS. Cells (MT-2) were allowed to grow at 36° C. in the presence of compounds for 3 days. To each well was added 0.05 ml of 1 mg XTT/ml in phosphate buffered saline (PBS) containing 0.025 mM phenazine methosulfate. Plates were incubated an additional four hours at 36° C. and the $A_{450}$ was determined. The absorption was proportional to the number of viable cells in the well. The concentration of compound which produced a 50% reduction in the number of viable cells was designated the $TC_{50}$.

Antiviral Activity of Ex. No. 5U Combined with AZT

The effect of combining Ex. No. 5U and AZT on the replication of HIV-i(RF)was determined in the yield reduction assay. $IC_{90}$s were calculated from dose response curves for each compound alone and for fixed ratio (wt/wt) combinations of the compounds using the medium effect method of Chou and Talalay, Adv. Enzyme Regul. 22:27–55 (1984). From these values, the combination indices were calculated as described by Schinazi et al., Antimicrob. Agents Chemother. 30:491–498 (1986). A combination index value of 1 indicates that a combination is additive. A value <1.0 indicates a synergistic relationship, while a value >1.0 indicates an antagonistic relationship. FIG. 1 shows the combined results from two experiments. The data demonstrate that Ex. No. 5U and AZT act synergistically to reduce the yield of virus.

Cytotoxicity of Ex. No. 5U Combined with AZT

Figure 2A:
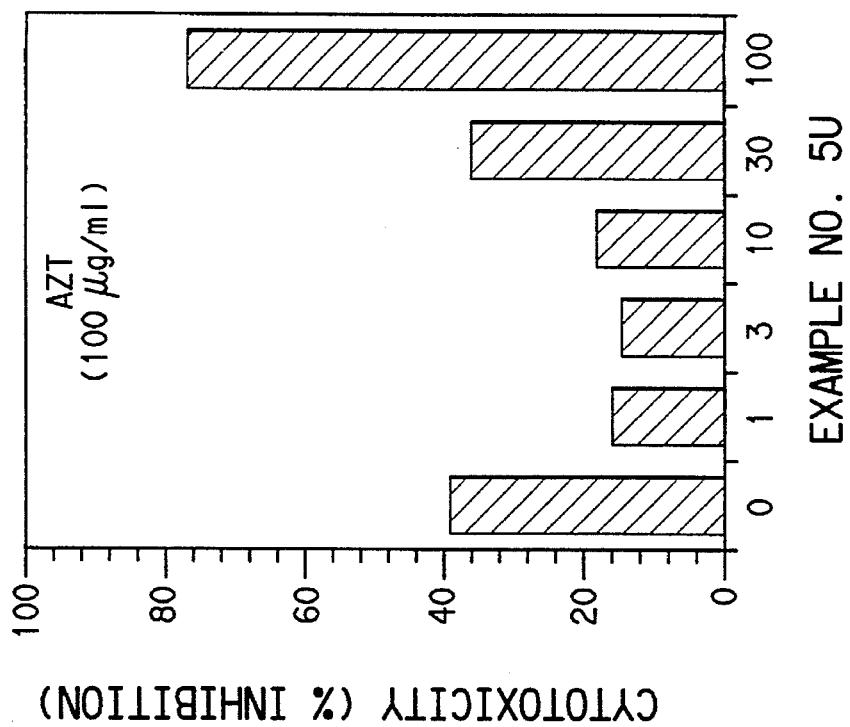
Figure 2B:
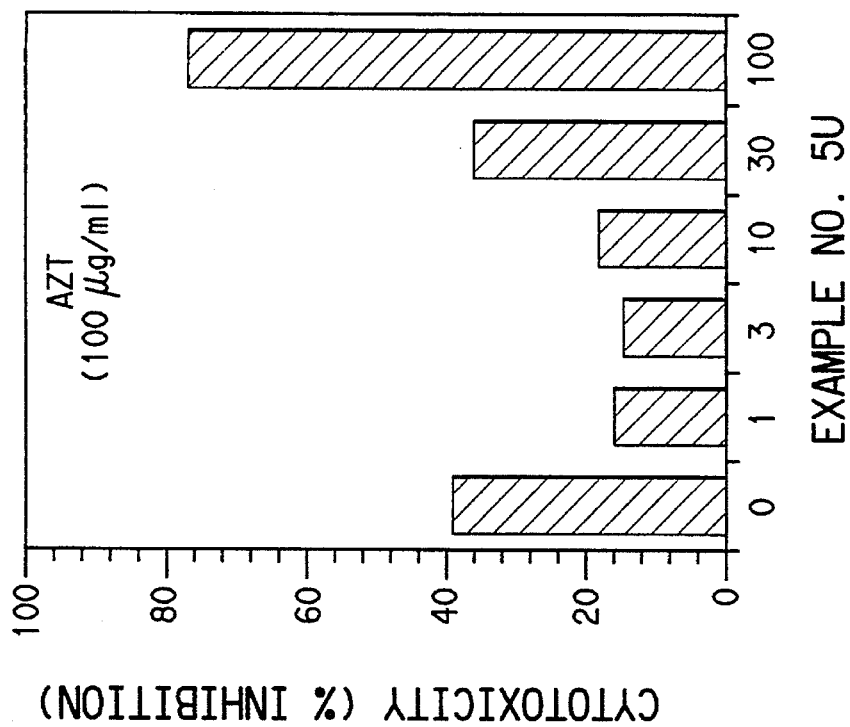
Figure 2A:
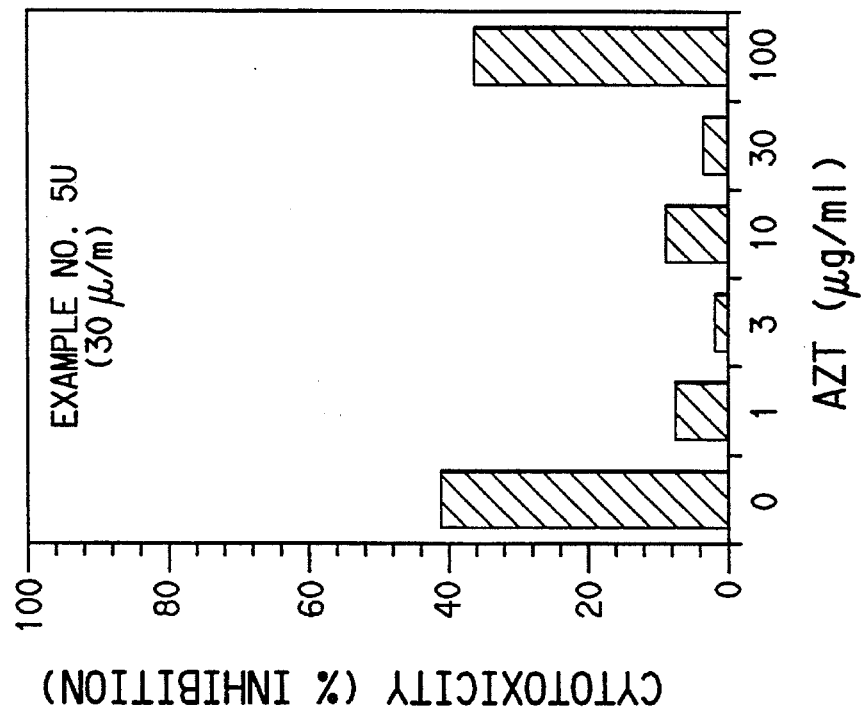

As shown in FIG. 1, Ex. No. 5U and AZT can act synergistically to inhibit HIV-1 replication. In order to determine how these combinations affect cell viability, a cytotoxicity assay was conducted on combinations of the two compounds over the range 0.3–100 µg/ml and the $TC_{50}$s calculated. The $TC_{50}$ for AZT alone was >100 µg/ml with 39% inhibition of cell growth at 100 µg/ml, while the $TC_{50}$ for Ex. No. 5U was 42 µg/ml. As shown in FIG. 2A, maintaining the concentration of Ex. No. 5U at 30 µg/ml and adding increasing amounts of AZT did not result in an increase in cytotoxicity. Maintaining AZT constant at 100 µg/ml and increasing the concentration of Ex. No. 5U (FIG. 2B) did not result in an increase in cytotoxicity except at 100 µg Ex. No. 5U/ml, a concentration greater than two times the $TC_{50}$. Indeed, several of the combinations appeared to be less toxic than either compound alone.

The results described herein demonstrate that a representative cyclic HIV protease inhibitor of Formula I, Ex. No. 5U, and a representative HIV RT inhibitor, AZT, act synergistically to reduce the yield of infectious HIV, without a corresponding increase in cytotoxicity. The data indicate that the concentrations of component (i) and component (ii) of the present invention (for example, Ex. No. 5U and AZT) could be reduced 3 to 5-fold relative to the concentration required when the agent is used alone as a single agent, and still achieve greater than 90% reduction in virus replication. The results presented indicate that a combination therapy comprising an cyclic HIV protease inhibitor of Formula (I) and an HIV RT inhibitor(for example, AZT) will be effective in treating patients infected with HIV with lower doses and, therefore, lower toxicity. The method and combination products of the present invention provide important advantages over single agent treatment.

What is claimed is:

1. A method of treating human immunodeficiency virus(HIV)infection in a mammal comprising administering in combination to the mammal a synergistically and therapeutically effective amount of: (i) at least one cyclic HIV protease inhibitor, and (ii) at least one HIV reverse transcriptase inhibitor selected from the group consisting of AZT, ddI, ddC, d4T, and 3TC;

wherein the HIV protease inhibitor is selected from compounds of the Formula (I):

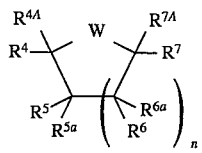

or a pharmaceutically acceptable salt thereof, wherein:

$R^4$ and $R^7$ are independently selected from the following groups:

hydrogen;

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

a $C_3$–$C_{14}$ carbocyclic ring system substituted with 0–3 $R^{11}$ or $R^{12}$;

a 5- to 10-membered heterocyclic ring system containing 1 to 4 heteroatoms independently selected from oxygen, nitrogen or sulfur, said heterocyclic ring system being substituted with 0–2 $R^{12}$;

—$OR^{13}$; —$SR^{13}$; $CO_2R^{13}$;

$R^{4A}$ and $R^{7A}$ are independently selected from the following groups:

hydrogen;

$C_1$–$C_4$ alkyl substituted with halogen or $C_1$–$C_2$ alkoxy;

benzyl substituted with halogen or $C_1$–$C_2$ alkoxy;

—$OR^{13}$; —$SR^{13}$; $CO_2R^{13}$;

$R^4$ and $R^{4A}$ can alternatively join to form a 5–7 membered carbocyclic ring substituted with 0–2 $R^{12}$;

$R^7$ and $R^{7A}$ can alternatively join to form a 5–7 membered carbocyclic ring substituted with 0–2 $R^{12}$;

n is 1;

$R^5$ is selected from H; halogen; $C_1$–$C_6$ alkyl substituted with 0–3 $R^{11}$; —$N(R^{20})_2$; —$SR^{20}$; or —$OR^{20}$;

$R^6$ is independently selected from: hydrogen, halogen, $C_1$–$C_6$ alkyl substituted with 0–3 $R^{11}$, —$N(R^{20})_2$, —$SR^{20}$, or —$OR^{21}$;

$R^5$ and $R^6$ can alternatively join to form an epoxide or aziridine ring; —$OCH_2SCH_2O$—; —$OS(=O)O$—; —$OC(=O)O$—; —$OCH_2O$—; —$OC(=S)O$—; —$OC(=O)C(=O)O$—; —$OC(CH_3)_2O$—; —$OC((CH_2)_3NH_2)(CH_3)O$—; —$OC(OCH_3)(CH_2CH_2CH_3)O$—; —$OS(=O)O$—; —$NHC(=O)NH$—; —$OC(=O)NH$—; —$NHC(=O)O$—; —$NHCH_2O$—; —$OCH_2NH$—; —$NHC(=S)O$—; —$OS(=O)NH$—; —$NHC(=O)C(=O)O$—; —$OC(=O)C(=O)NH$—; —$NHC(=O)C(=O)NH$—; —$OC(CH_3)_2O$—; —$NHC(CH_3)_2O$—; —$OC(CH_3)_2NH$— or any group that, when administered to a mammalian subject, cleaves to form a free dihydroxyl or diamino or hydroxyl and amino;

$R^{5a}$ is selected from hydrogen, halogen, $C_1$–$C_6$ alkyl, —$N(R^{20})_2$, —$SR^{20}$, or —$OR_{20}$;

$R^{6a}$ is selected from: hydrogen, halogen, $C_1$–$C_6$ alkyl, —$N(R^{20})_2$, —$SR^{20}$ or —$OR^{21}$;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
$C_1$–$C_6$ alkylaminocarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$; or any group that, when administered to a mammalian subject, cleaves to form a free hydroxyl, amino or sulfhydryl;

$R^{11}$ is selected from one or more of the following:
H, keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, or —$C(R^{14})=N(OR^{14})$;

1–3 amino acids linked together via amide bonds, and linked to $R^4$, $R^7$, $R^{20}$ or $R^{21}$ via the amine or carboxylate terminus;

—($C_1$–$C_3$ alkyl)aryl substituted with 0–2 $R^{12}$;

a $C_5$–$C_{14}$ carbocyclic residue substituted with 0–3 $R^{12}$;

a 5- to 10-membered heterocyclic ring system containing 1 to 4 heteroatoms independently selected from oxygen, nitrogen or sulfur, said heterocyclic ring system being substituted with 0–3 $R^{12}$;

$R^{11A}$ is selected from one or more of the following:
H, keto, halogen, cyano, —$CH_2NH_2$, —$NH_2$, —$CO_2H$, —$OC(=O)(C_1$–$C_3$ alkyl), —OH, $C_2$–$C_6$ alkoxyalkyl, —$C(=O)NH_2$, —$OC(=O)NH_2$, —$NHC(=O)NH_2$, —$SO_2NH_2$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, azido, aryl($C_1$–$C_3$ alkyl), a $C_5$–$C_{14}$ carbocyclic residue; a 5- to 10-membered heterocyclic ring system containing 1 to 4 heteroatoms independently selected from oxygen, nitrogen or sulfur, said heterocyclic ring system;

$R^{12}$ when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_0$ arylalkyl, $C_1$–$C_4$ alkoxy, —$CO_2H$, hydroxamic acid, hydrazide, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(O)_mR^{13}$, —$SO_2NR^{13}R^{14}$, —$NHSO_2R^{14}$, —$OCH_2CO_2H$, 2-(1-morpholino)ethoxy, —$C(R^{14})=N(OR^{14})$; or
a 5- or 6-membered heterocyclic ring containing from 1 to 4 heteroatoms independently selected from oxygen, nitrogen or sulfur;
or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{12}$ is attached to a saturated carbon atom, it may be =O or =S;

$R^{12}$ when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{13}$ is selected from:
H;
phenyl substituted with 0–3 $R^{11A}$;
benzyl substituted with 0–3 $R^{11A}$;
$C_1$–$C_6$ alkyl substituted with 0–3 $R^{11A}$;
$C_2$–$C_4$ alkenyl substituted with 0–3 $R^{11A}$;
$C_1$–$C_6$ alkylcarbonyl substituted with 0–3 $R^{11A}$;
$C_1$–$C_6$ alkoxycarbonyl substituted with 0–3 $R^{11A}$;
$C_1$–$C_6$ alkylaminocarbonyl substituted with 0–3 $R^{11A}$;
$C_3$–$C_6$ alkoxyalkyl substituted with 0–3 $R^{11A}$;
an amine protecting group when $R^{13}$ is bonded to N;
a hydroxy protecting group when $R^{13}$ is bonded to 0;

$R^{14}$, is OH; H; $CF_3$; $C_1$–$C_6$ alkyl substituted with 0–3 groups selected from OH, $C_1$–$C_4$ alkoxy, halogen, $NH_2$; $C_1$–$C_6$ alkoxy; $NH_2$; $C_2$–$C_6$ alkenyl; benzyl; an amine protecting group when $R^{14}$ is bonded to N; a hydroxy protecting group when $R^{14}$ is bonded to 0;

$R^{13}$ and $R^{14}$ can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

W is —$N(R^{22})C(=Z)N(R^{23})$—;

wherein:

Z is 0;

$R^{22}$ and $R^{23}$ are independently selected from the following:

hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;
—$OR^{22a}$; —$N(R^{22a})(R^{22b})$;

$R^{22a}$ and $R^{22b}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system containing 1 to 4 heteroatoms independently selected from oxygen, nitrogen or sulfur, said heterocyclic ring system being substituted with 0–2 $R^{32}$;

alternatively, $R^{22}$ can join with $R^4$ or $R^{4A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{23}$ can join with $R^7$ or $R^{7A}$ to form a 5- or 6-membered fused heterocyclic ring or carbocyclic ring substituted with 0–2 $R^{12}$, said heterocyclic ring containing 1–3 heteroatoms independently selected from N, S, or O; or alternatively, $R^{22}$ or $R^{23}$ can join with $R^5$ or $R^6$ to form a 0- to 7-membered bridge to form a carbocyclic or heterocyclic ring, said bridge being substituted with 0–2 $R^{12}$ and said bridge containing 0–3 heteroatoms independently selected from N, S, or O (i.e., a 0-membered bridge is formed when $R^{22}$ or $R^{23}$ are taken together with $R^5$ or $R^6$ to form a direct bond);

alternatively R23 can join with R7A to form a direct bond;
alternatively R22 can join with R4A to form a direct bond;

$R^{31}$ is selected from one or more of the following:
keto, halogen, cyano, —$CH_2NR^{13}R^{14}$, —$NR^{13}R^{14}$, —$CO_2R^{13}$, —$C(=O)R^{11}$, —$OC(=O)R^{13}$, —$OR^{13}$, $C_2$–$C_6$ alkoxyalkyl, —$S(O)_mR^{13}$, —$NHC(=NH)NHR^{13}$, —$C(=NH)NHR^{13}$, —$C(=O)NR^{13}R^{14}$, —$NR^{14}C(=O)R^{13}$, =$NOR^{14}$, —$NR^{14}C(=O)OR^{14}$, —$OC(=O)NR^{13}R^{14}$, —$NR^{13}C(=O)NR^{13}R^{14}$, —$NR^{14}SO_2NR^{13}R^{14}$, —$NR^{14}SO_2R^{13}$, —$SO_2NR^{13}R^{14}$, $C_1$–$C_4$ alkyl, $C_2$–$C_4$ alkenyl, $C_3$–$C_{10}$ cycloalkyl, $C_3$–$C_6$ cycloalkylmethyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2R^{13}$, 2-(1-morpholino)ethoxy, azido, —$C(R^{14})=N(OR^{14})$; or 1–3 amino acids, linked together via amide bonds, and linked to $R^{22}$, $R^{23}$, $R^{25}$, or $R^{27}$ via the amine or carboxylate terminus;

a $C_5$–$C_{14}$ carbocyclic residue substituted with 0–5 $R^{32}$; or a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$–$C_{10}$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)—$NR^{13}R^{14}$, —$C(=O)NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, or
—$C(=O)NR^{13}C(R^{11})_2NR^{13}R^{14}$;
—$C(=O)NR^{13}C(R^{11})_2NR^{13}NR^{14}$;
—$C(=O)NR^{13}C(R^{11})_2NR^{13}CO_2R^{13}$;
—$C(=O)NR^{13}$—($C_1$–$C_4$ alkyl)—$NR^{13}CO_2R^{13}$;
—$C(=O)N(R^{13})$—($C_1$–$C_4$ alkyl)—$R^{11}$; or
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$; —$C(=O)$—($C_1$–$C_4$ alkyl)—$NR^{13}R^{14}$; ($C_1$–$C_4$ alkyl)—$NR^{13}CO_2R^{13}$; or
$C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$, or OH;
$C_1$–$C_4$ alkyl substituted with 0–4 groups selected from: $R^{11}$, =$NR^{14}$, =$NNR^{13}C(=O)NR^{13}R^{14}$, or —$NR^{13}R^{14}$;
$C_2$–$C_4$ alkenyl substituted with 0–4 $R^{11}$;
$C_2$–$C_4$ alkynyl substituted with 0–4 $R^{11}$;
a 5- or 6-membered heterocyclic ring containing from 1 to 4 heteroatoms independently selected from oxygen, nitrogen or sulfur;
or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^{14}$; or, when $R^{32}$ is attached to a saturated carbon atom, it may be =O or =S;

$R^{32}$ when a substituent on nitrogen, is selected from one or more of the following:
phenyl, benzyl, phenethyl, hydroxy, $C_1$–$C_4$ hydroxyalkyl, $C_1C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, —$CO_2H$, $C_1$–$C_4$ alkylcarbonyloxy, $C_1$–$C_4$ alkylcarbonyl, —$C(R^{14})=N(OR^{14})$;

$R^{40}$ is selected from: H, $C_1$–$C_3$ alkyl;
$R^{41}$ is selected from:
—$C(=O)NR^{13}R^{14}$;
—$C(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$;
—$C(=O)H$;
—$C(=O)R^{11}$;
—$C(=O)$—($C_1$–$C_4$ alkyl)—$NR^{13}R^{14}$;

—C(=O)—($C_1$–$C_4$ alkyl)—$NR^{13}CO_2R^{13}$;
1–3 amino acids linked together via amide bonds, and linked to the N atom via the carboxylate terminus;
provided that:
$R^4$, $R^{4A}$, $R^7$ and $R^{7A}$ are not all hydrogen;
when $R^4$, $R^{4A}$ are hydrogen, at least $R^{22}$ is not hydrogen.

2. A method of claim 1 wherein the HIV protease inhibitor is a compound of Formula (I) wherein:

$R^4$ and $R^7$ are independently selected from the following groups:
hydrogen;
$C_1$–$C_4$ alkyl substituted with 0–3 $R^{11}$;
$C_3$–$C_4$ alkenyl substituted with 0–3 $R^{11}$;
$C_3$–$C_4$ alkynyl substituted with 0–3 $R^{11}$;

$R^{4A}$ and $R^{7A}$ are hydrogen;

$R^5$ is selected from fluoro or —$OR^{20}$;

$R^6$ is independently selected from: hydrogen, fluoro or —$OR^{21}$;

$R^5$ and $R^6$ can alternatively join to form an epoxide or aziridine ring; —$OCH_2SCH_2O$—; —$OS(=O)O$—; —$OC(=O)O$—; —$OCH_2$—; —$OC(=S)O$—; —$OC(=O)C(=O)O$—; —$OC(CH_3)_2O$—; —$OC(OCH_3)(CH_2CH_2CH_3)O$—; or any group that, when administered to a mammalian subject, cleaves to form a free dihydroxyl;

$R^{5a}$ is selected from hydrogen or fluoro;

$R^{6a}$ is selected from: hydrogen or fluoro;

$R^5$ and $R^{5a}$ can alternatively join to form =O, =S, or a ketal ring;

$R^6$ and $R^{6a}$ can alternatively join to form =O, =S, or a ketal ring;

$R^{20}$ and $R^{21}$ are independently selected from:
hydrogen;
$C_1$–$C_6$ alkylcarbonyl;
$C_1$–$C_6$ alkoxycarbonyl;
benzoyl; or
any group that, when administered to a mammalian subject, cleaves to form a free hydroxyl;

$R^{11}$ is selected from one or more of the following:
H, keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_4$ alkoxyalkyl, —$S(O)_mR^{13}$, $C_1$–$C_4$ alkyl, $C_2$–$C_4$ alkenyl, $C_3$–$C_{10}$ cycloalkyl;
a $C_5$–$C_{14}$ saturated or partially unsaturated carbocyclic residue substituted with 0–3 $R^{12}$;
aryl($C_1$–$C_3$ alkyl) substituted with 0–2 $R^{12}$;
aryl substituted with 0–3 $R^{12}$; or
a 5- to 10-membered heterocyclic ring system containing 1 to 4 heteroatoms independently selected from oxygen, nitrogen or sulfur, said heterocyclic ring system being substituted with 0–2 $R^{12}$;

$R^{12}$, when a substituent on carbon, is selected from one or more of the following:
phenyl, benzyl, phenethyl, phenoxy, benzyloxy, halogen, hydroxy, nitro, cyano, $C_1$–$C_4$ alkyl, $C_3$–$C_6$ cycloalkyl, $C_3$–$C_6$ cycloalkylmethyl, $C_7$–$C_{10}$ arylalkyl, $C_1$–$C_4$ alkoxy, —$CO_2H$, hydroxamic acid, hydrazide, oxime, boronic acid, sulfonamide, formyl, $C_3$–$C_6$ cycloalkoxy, —$OR^{13}$, $C_1$–$C_4$ alkyl substituted with —$NR^{13}R^{14}$, —$NR^{13}R^{14}$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1C_4$ alkylcarbonyl, $C_1$–$C_4$ alkylcarbonylamino, —$S(O)_mR^{13}$, —$SO_2NR^{13}R^{14}$, —$NHSO_2R^{14}$; or
a 5- or 6-membered heterocyclic ring containing from 1 to 4 heteroatoms independently selected from oxygen, nitrogen or sulfur;
or $R^{12}$ may be a 3- or 4- carbon chain attached to adjacent carbons on the ring to form a fused 5- or 6-membered ring, said 5- or 6- membered ring being optionally substituted on the aliphatic carbons with halogen, $C_1$–$C_4$ alkyl, $C_1$–$C_4$ alkoxy, hydroxy, or —$NR^{13}R^4$; or, when $R^{12}$ is attached to a saturated carbon atom, it may be =O or =S;

$R^{12}$, when a substituent on nitrogen, is selected from one or more of the following:
phenyl, benzyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethyl, —$CH_2NR^{13}R^{14}$, —$NR^{13}R^{14}$, $C_2$–$C_6$ alkoxyalkyl, $C_1$–$C_4$ haloalkyl, $C_1$–$C_4$ alkoxycarbonyl, $C_1$–$C_4$ alkylcarbonyloxy, $C_1$–$C_4$ alkylcarbonyl, —$CO_2H$;

$R^{13}$ is H, $C_1$–$C_6$ alkyl, $C_3$–$C_6$ alkoxyalkyl, $C_2$–$C_4$ alkenyl, phenyl, or benzyl;

$R^{14}$, is OH, H, $CF_3$, $C_1$–$C_4$ alkyl, $C_1$–$C_4$ alkoxy, $NH_2$, $C_2$–$C_4$ alkenyl, phenyl, or benzyl;

$R^{13}$ and $R^{14}$, can alternatively join to form —$(CH_2)_4$—, —$(CH_2)_5$—, —$CH_2CH_2N(R^{15})CH_2CH_2$—, or —$CH_2CH_2OCH_2CH_2$—;

$R^{15}$ is H or $CH_3$;

m is 0, 1 or 2;

$R^{22}$ and $R^{23}$ are independently selected from the following:
hydrogen;
$C_1$–$C_8$ alkyl substituted with 0–3 $R^{31}$;
$C_3$–$C_8$ alkenyl substituted with 0–3 $R^{31}$;
$C_3$–$C_8$ alkynyl substituted with 0–3 $R^{31}$;
$C_3$–$C_6$ cycloalkyl substituted with 0–3 $R^{31}$;

$R^{24a}$ is selected from —OH, $C_1$–$C_4$ alkoxy, mono- or di-($C_1$–$C_6$ alkyl)amino;

$R^{31}$ is selected from one or more of the following:
keto, halogen, cyano, —$CH_2NR^{13}R^{14}$, —$NR^{13}R^{14}$, —$CO_2R^{13}$, —$OC(=O)R^{13}$, —$OR^{13}$, $C_2$–$C_4$ alkoxyalkyl, —$S(O)_mR^{13}$, $C_1$–$C_4$ alkyl, $C_2$–$C_4$ alkenyl, $C_3$–$C_{10}$ cycloalkyl, benzyl, phenethyl, phenoxy, benzyloxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$NR^{13}R^{14}$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2CO_2H$, 2-(1-morpholino)ethoxy, —$C(R^{14})=N(OR^{14})$; or
a $C_5$–$C_{14}$ saturated or partially unsaturated carbocyclic residue substituted with 0–3 $R^{32}$;
aryl substituted with 0–3 $R^{32}$; or
a 5- to 10-membered heterocyclic ring system containing 1 to 4 heteroatoms independently selected from oxygen, nitrogen or sulfur, said heterocyclic ring system being substituted with 0–2 $R^{32}$;

$R^{32}$, when a substituent on carbon, is selected from one or more of the following:
phenethyl, phenoxy, $C_3$–$C_6$ cycloalkyl, $C_3$–$C_6$ cycloalkylmethyl, $C_7$–$C_{10}$ arylalkyl, hydrazide, oxime, boronic acid, $C_2$–$C_6$ alkoxyalkyl, methylenedioxy, ethylenedioxy, $C_1$–$C_4$ alkylcarbonyloxy, —$NHSO_2R^{14}$, benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$-$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2R^{13}$, phenyl, —$C(=O)NR^{13}$—$(C_1$-$C_4$ alkyl)—$NR^{13}R^{14}$, —$C(=O)NR^{40}R^{41}$, $C_1$-$C_4$ haloalkyl, $C_1$-$C_4$ haloalkoxy, $C_2$-$C_4$ haloalkenyl, $C_1$-$C_4$ haloalkynyl, or
—$C(=O)NR^{13}C(R^{11})_2NR^{13}R^{14}$;
—$C(=O)NR^{13}C(R^{11})_2NR^{13}NR^{14}$;
—$C(=O)NR^{13}C(R^{11})_2NR^{13}CO_2R^{13}$;
—$C(=O)NR^{13}$—$(C_1$-$C_4$ alkyl )—$NR^{13}CO_2R^{13}$; or
—$C(=O)C(R^{11})_2NR^{13}R^{14}$;
—$C(=O)C(R^{11})_2NR^{13}NR^{14}$;
—$C(=O)C(R^{11})_2NR^{13}CO_2R^{13}$; —$C(=O)$—$(C_1$-$C_4$ alkyl)—$NR^{13}R^{14}$; —$C(=O)$— $(C_1$-$C_4$ alkyl)—$NR^{13}CO_2R^{13}$; or $C_1$-$C_4$ alkoxy substituted with 0–3 groups selected from: $R^{11}$, $C_3$-$C_6$ cycloalkyl, —$CO_2R^{13}$, —$C(=O)NR^{13}R^{14}$, —$NR^{13}R^{14}$, or OH;

$C_1$-$C_4$ alkyl substituted with 0–3 groups selected from: $R^{11}$, =$NR^{14}$, =$NNR^{13}C(=O)NR^{13}R^{14}$, or —$NR^{13}R^{14}$;

$C_2$-$C_4$ alkenyl substituted with 0–3 $R^{11}$;

$C_2$-$C_4$ alkynyl substituted with 0–3 $R^{11}$;

a 5- or 6-membered heterocyclic ring containing from 1 to 4 heteroatoms independently selected from oxygen, nitrogen or sulfur;

or $R^{32}$ may be a 3- or 4- carbon chain attached to adjacent carbons on the ring to form a fused 5- or 6-membered ring, said 5- or 6- membered ring being optionally substituted on the aliphatic carbons with halogen, $C_1$-$C_4$ alkyl, $C_1$-$C_4$ alkoxy, hydroxy, or —$NR^{13}R^{14}$; or, when $R^{32}$ is attached to a saturated carbon atom, it may be =O or =S;

$R^{32}$, when a substituent on nitrogen, is selected from one or more of the following:

phenyl, benzyl, phenethyl, hydroxy, $C_1$-$C_4$ hydroxyalkyl, $C_1$-$C_4$ alkoxy, $C_1$-$C_4$ alkyl, $C_3$-$C_6$ cycloalkyl, $C_3$-$C_6$ cycloalkylmethyl, —$CH_2NR^{13}R^{14}$, —$NR^{13}R^{14}$, $C_1$-$C_6$ alkoxyalkyl, $C_1$-$C_4$ haloalkyl, $C_1$-$C_4$ alkoxycarbonyl, $C_1$-$C_4$ alkylcarbonyloxy, $C_1$-$C_4$ alkylcarbonyl, —$CO_2H$, —$C(R^{14})=N(OR^{14})$;

$R^{40}$ is selected from: H, $C_1$-$C_3$ alkyl;

$R^{41}$ is selected from:
—$C(=O)NR^{13}R^{14}$;
—$(=O)NR^{13}NR^{14}$;
—$C(=O)C(R^{11})_2NR^{13}R^{14}$;
—$C(=O)C(R^{11})_2NR^{13}NR^{14}$;
—$C(=O)C(R^{11})_2R^{13}CO_2R^{13}$;
—$C(=O)H$;
—$C(=O)R^{11}$;
—$C(=O)$—$(C_1$-$C_4$ alkyl)—$NR^{13}R^{11}$;
—$C(=O)$—$(C_1$-$C_4$ alkyl)—$NR^{13}CO_2R^{13}$;

1–3 amino acids linked together via amide bonds, and linked to the N atom via the carboxylate terminus.

3. A method of claim 1 wherein the HIV protease inhibitor is a compound of Formula (I) wherein:

$R^4$ and $R^7$ are independently selected from the following groups:
hydrogen;
$C_1$-$C_3$ alkyl substituted with 0–1 $R^{11}$;

$R^{4A}$ and $R^{7A}$ are hydrogen;

$R^5$ is —$OR^{20}$;

$R^{5A}$ and $R^{6A}$ are hydrogen;

$R^6$ is hydrogen or —$OR^{21}$;

$R^{20}$ and $R^{21}$ are independently hydrogen or any group that, when administered to a mammalian subject, cleaves to form a free hydroxyl;

$R^{11}$ is selected from one or more of the following:
H; halogen; —$OR^{13}$;
$C_3$-$C_{10}$ cycloalkyl substituted with 0–2 $R^{12}$;
$C_1$-$C_4$ alkyl substituted with 0–2 $R^{12}$;
aryl($C_1$-$C_3$ alkyl)substituted with 0–2 $R^{12}$; aryl substituted with 0–2 $R^{12}$; or
a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 $R^{12}$;

$R^{12}$, when a substituent on carbon, is selected from one or more of the following:
benzyloxy, halogen, methyl, $C_1$-$C_4$ alkoxy, $CF_3$, 2-(1-morpholino)ethoxy, —$CO_2H$, hydroxamic acid, hydrazide, —$C(R^{14})=N(OR^{14})$, cyano, boronic acid, sulfonamide, formyl, $C_3$-$C_6$ cycloalkoxy, $C_1$-$C_4$ alkyl substituted with —$NR^{13}R^{14}$, —$NR^{13}R^{14}$, hydroxy, hydroxymethyl; or $R^{12}$, when a substituent on nitrogen, is methyl;

$R^{13}$ is H, $C_1$-$C_4$ alkyl, $C_2$-$C_4$alkenyl, or benzyl;

$R^{14}$ is OH, H, $CF_3$, $C_1$-$C_4$ alkyl, $C_1$-$C_4$ alkoxy, $NH_2$, $C_2$-$C_4$ alkenyl, or benzyl;

$R^{13}$ and $R^{14}$, can alternatively join to form —$(CH_2)_4$—, —$(CH_2)_5$—, —$CH_2CH_2N(R^{15})CH_2CH_2$—, or —$CH_2CH_2O$ $CH_2CH_2$—;

$R^{15}$ is H or $CH_3$;

$R^{22}$ and $R^{23}$ are independently selected from the following:
hydrogen;
$C_1$-$C_8$ alkyl substituted with 0–3 $R^{31}$;
$C_2$-$C_6$ alkenyl substituted with 0–3 $R^{31}$;
$C_2$-$C_4$ alkynyl substituted with 0–3 $R^{31}$;

$R^{31}$ is selected from one or more of the following:
halogen, —$OR^{13}$, $C_1$-$C_4$ alkyl, $C_3$-$C_{10}$ cycloalkyl, —$C(R^{14})=N(OR^{14})$, —$CO_2R^{13}$, —$S(O)_mR^{13}$;
aryl substituted with 0–5 $R^{32}$; or
a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;

$R^{32}$, when a substituent on carbon, is selected from one or more of the following:
benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$-$C_6$ cycloalkoxy, —$NR^{13}R^{14}$, —$C(R^{14})=N(OR^{14})$, $NO_2$, —$OR^{13}$, —$NR^{40}R^{41}$, —$SO_mR^{13}$, —$SO_mNR^{13}R^{14}$, —$C(=O)NR^{13}R^{14}$, —$OC(=O)NR^{13}R^{14}$, —$C(=O)R^{11}$, —$OC(=O)R^{11}$, —$OCO_2^{R13}$, phenyl, —$C(=O)NR^{13}$—$(C_1$-$C_4$ alkyl)—$NR^{13}R^{14}$, —$C(=O)NR^{40}R^{41}$, $C_1$-$C_4$ haloalkyl, $C_1$-$C_4$ haloalkoxy, $C_2$-$C_4$ haloalkenyl, $C_1$-$C_4$ haloalkynyl, —$C(=O)NR^{13}R^{14}$; —$C(=O)C(R^{11})_2NR^{13}R^{14}$; —$C(=O)C(R^{11})_2NR^{13}NR^{14}$;
—$C(=O)C(R^{11})_2NR^{13}CO_2R^{13}$; —$C(=O)$—$(C_1$-$C_4$ alkyl)—$NR^{13}R^{14}$; —$C(=O)$ $(C_1$-$C_4$ alkyl)—$NR^{13}CO_2R^{13}$; or $C_1$–$C_4$ alkoxy substituted with 0–3 groups selected from: $R^{11}$, $C_3$–$C_6$ cycloalkyl, —C(═O)$NR^{13}R^{14}$, —$NR^{13}R^{14}$, or OH;

$C_1$–$C_4$ alkyl substituted with 0–3 groups selected from: $R^{11}$; ═$NR^{14}$; ═$NNR^{13}$C(═O)$NR^{13}R^{14}$, or —$NR^{13}R^{11}$;

$C_2$–$C_4$ alkenyl substituted with 0–3 $R^{11}$;

$C_2$–$C_4$ alkynyl substituted with 0–3 $R^{11}$;

a 5- or 6-membered heterocyclic ring containing from 1 to 4 heteroatoms independently selected from oxygen, nitrogen or sulfur;

$R^{32}$, when a substituent on nitrogen, is methyl;

m is 0, 1, or 2;

$R^{40}$ is selected from: H, $C_1$–$C_3$ alkyl;

$R^{41}$ is selected from:
—C(═O)$NR^{13}R^{14}$;
—C(═O)$NR^{13}NR^{14}$;
—C(═O)C($R^{11}$)$_2$$NR^{13}R^{14}$;
—C(═O)C($R^{11}$)$_2$$NR^{13}NR^{14}$;
—C(═O)C($R^{11}$)$_2$$NR^{13}CO_2R^{13}$;
—C(═O)H;
—C(═O)$R^{11}$;
—C(═O)—($C_1$–$C_4$ alkyl)—$NR^{13}R^{14}$;
—C(═O)—($C_1$–$C_4$ alkyl)—$NR^{13}CO_2R^{13}$;

1–3 amino acids linked together via amide bonds, and linked to the N atom via the carboxylate terminus;

provided that:

$R^4$ and $R^7$ are not both hydrogen;

when $R^{14}$, is hydrogen, $R^{22}$ is not hydrogen.

4. A method of claim 3 wherein the HIV protease inhibitor is a compound of Formula (I) wherein:

$R^4$ and $R^7$ are selected from benzyl, fluorobenzyl, pyrrolylmethyl, methoxybenzyl, isobutyl, nitrobenzyl or aminobenzyl;

$R^5$ is —OH;

$R^6$ is hydrogen or —OH;

$R^{13}$ is H, $C_1$–$C_4$ alkyl, $C_2$–$C_4$ alkenyl, or benzyl;

$R^{14}$, is OH, H, $CF_3$, $C_1$–$C_4$ alkyl, $C_1$–$C_4$ alkoxy, $NH_2$, $C_2$–$C_4$ alkenyl, or benzyl;

$R^{13}$ and $R^{14}$, can alternatively join to form —(CH$_2$)$_4$—, —(CH$_2$)$_5$—, —CH$_2$CH$_2$N($R^{15}$)CH$_2$CH$_2$—, or —CH$_2$CH$_2$OCH$_2$CH$_2$—;

$R^{22}$ and $R^{23}$ are independently selected from the following:
hydrogen;
$C_1$–$C_8$ alkyl substituted with 0–2 $R^{31}$;
$C_1$–$C_6$ alkenyl substituted with 0–2 $R^{31}$;
$C_2$–$C_4$ alkynyl substituted with 0–2 $R^{31}$;

$R^{31}$ is selected from one or more of the following:
halogen, —$OR^{13}$, $C_1$–$C_4$ alkyl, $C_3$–$C_{10}$ cycloalkyl, —C($R^{14}$)═N(O$R^{14}$), —$CO_2R^{13}$, —S(O)$_mR^{13}$;
aryl substituted with 0–5 $R^{32}$; or
a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;

$R^{32}$ when a substituent on carbon, is selected from one or more of the following:
—$CONH_2$, —$CO_2H$, —CHO, —$CH_2NHOH$, —$CH_2NR^{13}R^{14}$, —$NR^{13}R^{14}$, hydroxy, hydroxymethyl, —C($R^{14}$)═N(O$R^{14}$), halogen, methoxy, methyl, nitro, cyano, allyloxy, —$CO_2CH_3$, —NHCHO, —$NHCOCH_3$, —$OCO_2CH_3$, —CH═NCH$_2$CH$_2$OH, —OCONHCH$_2$C$_6$H$_5$, —OCONHCH$_3$, oxazolidinyl, —C≡C—CH$_2$OH, —COCH$_3$, hydroxyethyl, $C_1$–$C_3$ alkyl(said alkyl substituted with 0–4 halogen, or OH), tetrazolyl, —OCH$_2$CONH$_2$, —CONHNH$_2$, —CH═NNHCONH$_2$, —CONHOCH$_3$, —CH$_2$CH(OH)CH$_2$OH, adamantamido, hydroxyethoxy, dihydroxyethyl, —C(NH$_2$)═NH, —CONHCH$_3$, —B(OH)$_2$, benzyloxy, —CONHCH$_2$CH$_3$, —CON(CH$_2$CH$_3$)$_2$, methylthio, —SO$_2$CH$_3$, —NHCONH$_2$, —NHCONHCH$_3$, —NHCOCH$_2$N(CH$_3$)$_2$, —NHCOCH$_2$NHCH$_3$, —NHCOCH$_2$NHCO$_2$CH$_2$C$_6$H$_5$, —NHCOCH$_2$NH$_2$, —NHCOCH(CH$_3$)NHCO$_2$CH$_2$C$_6$H$_5$, —NHCOCH(CH$_2$C$_6$H$_5$)NHCO$_2$CH$_2$C$_6$H$_5$, —NHCOCH(CH$_3$)NH$_2$, —NHCOCH(CH$_2$C$_6$H$_5$)NH$_2$, —CO$_2$CH$_2$CH$_3$, —CONHCH$_2$CH$_3$, —CONHCH(CH$_3$)$_2$, —CH$_2$-imidazole, —COC(CH$_3$)$_3$, —CH(OH)CF$_3$, —CO-imidazole, —CO-pyrazolyl, oxadiazolidinonyl, —COCF$_3$, —COCH$_2$CH$_3$, —COCH$_2$CH$_2$CH$_3$, pyrazolyl, —SO$_2$NH$_2$, —C(CH$_2$CH$_3$)═N(OH) or —C(CF$_3$)═N(OH), phenyl, acetoxy, hydroxyamino, —N(CH$_3$)(CHO), cyclopropylmethoxy, —$CONR^{13}R^{14}$, —CONHOH, (diethylaminoethyl)aminocarbonyl, (N-ethyl, N-methylaminoethyl)aminocarbonyl, (4-methylpiperazinylethyl)aminocarbonyl, pyrrolidinylethyl)aminocarbonyl, (piperidinylethyl)aminocarbonyl, —NHCOCH$_2$NHCH$_3$, N-(2-(4-morpholino)ethyl)aminocarbonyl, N-(2-(N,N-dimethylamino)ethyl)aminocarbonyl;

$R^{32}$ when a substituent on nitrogen, is methyl.

5. A method of claim 1 wherein the HIV protease inhibitor is a compound of the Formula (II'):

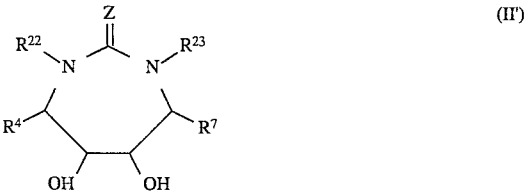

wherein:

$R^4$ and $R^7$ are independently selected from: benzyl, fluorobenzyl, pyrrolylmethyl, methoxybenzyl, isobutyl, nitrobenzyl or aminobenzyl;

$R^{22}$ and $R^{23}$ are independently selected from the group consisting of:
hydrogen, allyl, methyl, ethyl, propyl, cyclopropylmethyl, n-butyl, i-butyl, CH$_2$CH═C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(═O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))benzyl, (pyridylmethylaminocarbonyl)benzyl, (oxadiazolidinonyl)benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino )benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

6. A method of claim 1 wherein the HIV protease inhibitor is a compound of Formula (IIa):

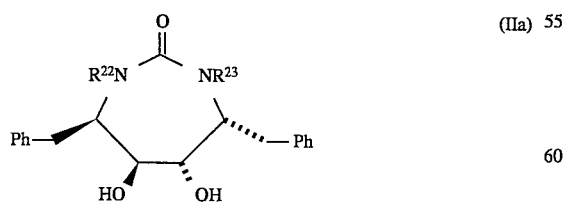

wherein R$^{22}$ and R$^{23}$ are independently selected from the group consisting of:

hydrogen, allyl, methyl, ethyl, propyl, cyclopropylmethyl, n-butyl, i-butyl, CH$_2$CH=C(CH$_3$)$_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyloxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, (H$_2$NC(=O))-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, (CH$_3$O$_2$CO)-benzyl, (HOCH$_2$CH$_2$N=CH)-benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethyl-boronic acid, N-hydroxylaminomethylbenzyl, (hydroxyl)ethylbenzyl, (CH$_3$C(=NOH))-benzyl, (H$_2$NNHC(=O))-benzyl, (H$_2$NC(=O)NHN=CH)-benzyl, (CH$_3$ONHC(=O))-benzyl, (HONHC(=O))-benzyl, (CH$_3$NHC(=O))-benzyl, N,N-dimethylaminocarbonylbenzyl, (HOCH$_2$CH(OH)CH$_2$O)benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, (CH$_3$CH$_2$NHC(=O))-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, (H$_2$NSO$_2$)-benzyl, dihydroxyethylbenzyl, (MeHNC(=O)NH)-benzyl, (H$_2$NC(=O)NH)-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, (CH$_3$CH$_2$C(=NOH))-benzyl, (trifluorohydroxyethyl)benzyl, (CF$_3$C(=NOH))-benzyl, (N-methylglycyl)aminobenzyl, ((4-morpholino)ethyl)aminocarbonylbenzyl, (N,N-dimethylaminoethyl)aminocarbonylbenzyl, (N,N-diethylaminoethyl)aminocarbonylbenzyl, (4-methylpiperazin-1-ylethyl)aminocarbonylbenzyl, (benzyl-NHC(=O)O)benzyl, (CH$_3$NHC(=O)O)benzyl, (NH$_2$C(=O)CH$_2$O)benzyl, (NH$_2$C(=NH))benzyl, ((N-phenylmethoxycarbonyl)glycylamino)benzyl, (imidazolylmethyl)benzyl, ((CH$_3$)$_3$C—C(=O))benzyl, (N-methyl-N-ethylaminoethyl)aminocarbonylbenzyl, (pyrrolidinylethyl)aminocarbonylbenzyl, (piperidinylethyl)aminocarbonylbenzyl.

7. A method of claim 6 wherein the HIV protease inhibitor is selected from the group of compounds consisting of:

the compound of Formula (IIa) where R$^{22}$ is allyl and R$^{23}$ is allyl;

the compound of Formula (IIa) wherein $R^{22}$ is propyl and $R^{23}$ is propyl;

the compound of Formula (IIa) wherein $R^{22}$ is cyclopropylmethyl and $R^{23}$ is cyclopropylmethyl;

the compound of Formula (IIa) wherein $R^{22}$ is n-hexyl and $R^{23}$ is n-hexyl;

the compound of Formula (IIa) wherein $R^{22}$ is n-butyl and $R^{23}$ is n-butyl;

the compound of Formula (IIa) wherein $R^{22}$ is $CH_2CH=C(CH_3)_2$ and $R^{23}$ is $CH_2CH=C(CH_3)_2$;

the compound of Formula (IIa) wherein $R^{22}$ is $CH_2CH=C(CH_3)_2$ and $R^{23}$ is H;

the compound of Formula (IIa) wherein $R^{22}$ is i-pentyl and $R^{23}$ is i-pentyl;

the compound of Formula (IIa) wherein $R^{22}$ is 2-methallyl and $R^{23}$ is 2-methallyl;

the compound of Formula (IIa) wherein $R^{22}$ is n-pentyl and $R^{23}$ is n-pentyl;

the compound of Formula (IIa) wherein $R^{22}$ is benzyl and $R^{23}$ is benzyl;

the compound of Formula (IIa) wherein $R^{22}$ is i-hexyl and $R^{23}$ is i-hexyl;

the compound of Formula (IIa) wherein $R^{22}$ is allyl and $R^{23}$ is isoprenyl;

the compound of Formula (IIa) wherein $R^{22}$ is 1-cinnamyl and $R^{23}$ is 1-cinnamyl;

the compound of Formula (IIa) wherein $R^{22}$ is 4-fluorobenzyl and $R^{23}$ is 4-fluorobenzyl;

the compound of Formula (IIa) wherein $R^{22}$ is cyclopropylmethyl and $R^{23}$ is benzyl;

the compound of Formula (IIa) wherein $R^{22}$ is allyl and $R^{23}$ is benzyl;

the compound of Formula (IIa) wherein $R^{22}$ is $CH_2CH=C(CH_3)_2$ and $R^{23}$ is cyclopropylmethyl;

the compound of Formula (IIa) wherein $R^{22}$ is 2-naphthylmethyl and $R^{23}$ is 2-napthylmethyl;

the compound of Formula (IIa) wherein $R^{22}$ is n-butyl and $R^{23}$ is benzyl;

the compound of Formula (IIa) wherein $R^{22}$ is allyl and $R^{23}$ is cyclopropylmethyl;

the compound of Formula (IIa) wherein $R^{22}$ is n-butyl and $R^{23}$ is cyclopropylmethyl;

the compound of Formula (IIa) wherein $R^{22}$ is $CH_2CH=C(CH_3)_2$ and $R^{23}$ is benzyl;

the compound of Formula (IIa) wherein $R^{22}$ is benzyl and $R^{23}$ is ethyl;

the compound of Formula (IIa) wherein $R^{22}$ is benzyl and $R^{23}$ is 4-pyridinylmethyl;

the compound of Formula (IIa) wherein $R^{22}$ is cyclopropylmethyl and $R^{23}$ is 4-pyridinylmethyl;

the compound of Formula (IIa) wherein $R^{22}$ is benzyl and $R^{23}$ is cyclopentylmethyl;

the compound of Formula (IIa) wherein $R^{22}$ is cyclopropylmethyl and $R^{23}$ is cyclopentylmethyl;

the compound of Formula (IIa) wherein $R^{22}$ is benzyl and $R^{23}$ is n-propyl;

the compound of Formula (IIa) wherein $R^{22}$ is cyclopropylmethyl and $R^{23}$ is cinnamyl;

the compound of Formula (IIa) wherein $R^{22}$ is cyclopropylmethyl and $R^{23}$ is 2-naphthylmethyl;

the compound of Formula (IIa) wherein $R^{22}$ is cyclopentylmethyl and $R^{23}$ is 2-naphthylmethyl;

the compound of Formula (IIa) wherein $R^{22}$ is benzyl and $R^{23}$ is 2-naphthylmethyl;

the compound of Formula (IIa) wherein $R^{22}$ is cyclopropylmethyl and $R^{23}$ is 2-pyridinylmethyl;

the compound of Formula (IIa) wherein $R^{22}$ is 3-cyanobenzyl and $R^{23}$ is 3-cyanobenzyl;

the compound of Formula (IIa) wherein $R^{22}$ is allyl and $R^{23}$ is 2-naphthylmethyl;

the compound of Formula (IIa) wherein $R^{22}$ is n-propyl and $R^{23}$ is 2-naphthylmethyl;

the compound of Formula (IIa) wherein $R^{22}$ is n-butyl and $R^{23}$ is 2-naphthylmethyl;

the compound of Formula (IIa) wherein $R^{22}$ is hydrogen and $R^{23}$ is 2-naphthylmethyl;

the compound of Formula (IIa) wherein $R^{22}$ is 4-pyridinylmethyl and $R^{23}$ is 2-naphthylmethyl;

the compound of Formula (IIa) wherein $R^{22}$ is allyl and $R^{23}$ is cyclopentylmethyl;

the compound of Formula (IIa) wherein $R^{22}$ is allyl and $R^{23}$ is 2-quinolinylmethyl;

the compound of Formula (IIa) wherein $R^{22}$ is 3-pyridinylmethyl and $R^{23}$ is cyclopropylmethyl;

the compound of Formula (IIa) wherein $R^{22}$ is 3-pyridinylmethyl and $R^{23}$ is 2-naphthylmethyl;

the compound of Formula (IIa) wherein $R^{22}$ is 3-hydroxybenzyl and $R^{23}$ is 3-hydroxybenzyl;

the compound of Formula (IIa) wherein $R^{22}$ is vinylbenzyl and $R^{23}$ is vinylbenzyl;

the compound of Formula (IIa) wherein $R^{22}$ is 3-allyloxybenzyl and $R^{23}$ is 3-hydroxybenzyl;

the compound of Formula (IIa) wherein $R^{22}$ is 3-pyridinylmethyl and $R^{23}$ is 3-pyridinylmethyl;

the compound of Formula (IIa) wherein $R^{22}$ is 2-naphthylmethyl and $R^{23}$ is 4-fluorobenzyl;

the compound of Formula (IIa) wherein $R^{22}$ is 4-hydroxybenzyl and $R^{23}$ is 4-hydroxybenzyl;

the compound of Formula (IIa) wherein $R^{22}$ is 3-hydroxymethylbenzyl and $R^{23}$ is 3-hydroxymethylbenzyl;

the compound of Formula (IIa) wherein $R^{22}$ is 3-carbomethoxybenzyl and $R^{23}$ is 3-carbomethoxybenzyl;

the compound of Formula (IIa) wherein $R^{22}$ is 4-hydroxymethylbenzyl and $R^{23}$ is 4-hydroxymethylbenzyl;

the compound of Formula (IIa) wherein $R^{22}$ is 3-formylbenzyl and $R^{23}$ is 3-formylbenzyl;

the compound of Formula (IIa) wherein $R^{22}$ is 4-cyanobenzyl and $R^{23}$ is 4-cyanobenzyl;

the compound of Formula (IIa) wherein $R^{22}$ is 4-formylbenzyl and $R^{23}$ is 4-formylbenzyl;

the compound of Formula (IIa) wherein $R^{22}$ is 4-hydroxybenzyl and $R^{23}$ is 2-propyl;

the compound of Formula (IIa) wherein $R^{22}$ is 3-hydroxybenzyl and $R^{23}$ is 2-propyl;

the compound of Formula (IIa) wherein $R^{22}$ is 3-carboxybenzyl and $R^{23}$ is 3-carboxybenzyl;

the compound of Formula (IIa) wherein $R^{22}$ is 3-formaldoximebenzyl and $R^{23}$ is 3-formaldoximebenzyl;

the compound of Formula (IIa) wherein $R^{22}$ is cyclopropylmethyl and $R^{23}$ is 3-hydroxybenzyl;

the compound of Formula (IIa) wherein $R^{22}$ is cyclopropylmethyl and $R^{23}$ is 4-hydroxybenzyl;

the compound of Formula (IIa) wherein $R^{22}$ is cyclobutylmethyl and $R^{23}$ is cyclobutylmethyl;

the compound of Formula (IIa) wherein $R^{22}$ is cyclopentylmethyl and $R^{23}$ is cyclopentylmethyl;

the compound of Formula (IIa) wherein $R^{22}$ is 3n-butyl and $R^{23}$ is $CH_2CH=C(CH_3)_2$;

the compound of Formula (IIa) wherein $R^{22}$ is n-butyl and $R^{23}$ is cyclopentylmethyl;

the compound of Formula (IIa) wherein $R^{22}$ is benzyl and $R^{23}$ is H;

the compound of Formula (IIa) wherein $R^{22}$ is 3-fluorobenzyl and $R^{23}$ is 3-fluorobenzyl;

the compound of Formula (IIa) wherein $R^{22}$ is 3-methoxybenzyl and $R^{23}$ is 3-methoxybenzyl;

the compound of Formula (IIa) wherein $R^{22}$ is 3,4-difluorobenzyl and $R^{23}$ is 3,4-difluorobenzyl;

the compound of Formula (IIa) wherein $R^{22}$ is 4-methylbenzyl and $R^{23}$ is 4-methylbenzyl;

the compound of Formula (IIa) wherein $R^{22}$ is 4-chlorobenzyl and $R^{23}$ is 4-chlorobenzyl;

the compound of Formula (IIa) wherein $R^{22}$ is cyclopropylmethyl and $R^{23}$ is 4-fluorobenzyl;

the compound of Formula (IIa) wherein $R^{22}$ is 3-chlorobenzyl and $R^{23}$ is 3-chlorobenzyl;

the compound of Formula (IIa) wherein $R^{22}$ is 3-nitrobenzyl and $R^{23}$ is 3-nitrobenzyl;

the compound of Formula (IIa) wherein $R^{22}$ is 3-methylbenzyl and $R^{23}$ is 3-methylbenzyl;

the compound of Formula (IIa) wherein $R^{22}$ is 3-bromobenzyl and $R^{23}$ is 3-bromobenzyl;

the compound of Formula (IIa) wherein $R^{22}$ is 4-fluorobenzyl and $R^{23}$ is H;

the compound of Formula (IIa) wherein $R^{22}$ is cyclopropylmethyl and $R^{23}$ is 3-chlorobenzyl;

the compound of Formula (IIa) wherein $R^{22}$ is 3-aminobenzyl and $R^{23}$ is 3-aminobenzyl;

the compound of Formula (IIa) wherein $R^{22}$ is 3-nitrobenzyl and $R^{23}$ is H;

the compound of Formula (IIa) wherein $R^{22}$ is 3-(NHCHO) benzyl and $R^{23}$ is 3-(NHCHO)benzyl;

the compound of Formula (IIa) wherein $R^{22}$ is 3-(NHCOCH$_3$)benzyl and $R^{23}$ is 3-(NHCOCH$_3$)benzyl;

the compound of Formula (IIa) wherein $R^{22}$ is 3,4-dihydroxybenzyl and $R^{23}$ is 3,4-dihydroxybenzyl;

the compound of Formula (IIa) wherein $R^{22}$ is 3-formaldoximebenzyl and $R^{23}$ is 3-(N-hydroxy)aminomethylbenzyl;

the compound of Formula (IIa) wherein $R^{22}$ is 3-(N-hydroxy)aminomethylbenzyl and $R^{23}$ is 3-(N-hydroxy)aminomethylbenzyl;

the compound of Formula (IIa) wherein $R^{22}$ is 3-(CH$_3$OC(=O)O—)benzyl and $R^{23}$ is 3-(CH$_3$OC(=O)O—)benzyl;

the compound of Formula (IIa) wherein $R^{22}$ is 3-(1hydroxyethyl)benzyl and $R^{23}$ is 3-(1-hydroxyethyl)benzyl;

the compound of Formula (IIa) wherein $R^{22}$ is 3-(HOCH$_2$CH$_2$N=CH)benzyl and $R^{23}$ is 3-(HOCH$_2$CH$_2$N=CH)benzyl;

the compound of Formula (IIa) wherein $R^{22}$ is 3-(HOCH$_2$CH$_2$N=CH)benzyl and $R^{23}$ is 3-(2-oxazolidinyl)benzyl;

the compound of Formula (IIa) wherein $R^{22}$ is 3-(C$_6$H$_5$CH$_2$NHC(=O)O)benzyl and $R^{23}$ is 3-(C$_6$H$_5$CH$_2$NHC(=O)O)benzyl;

the compound of Formula (IIa) wherein $R^{22}$ is 3-(CH$_3$NHC(=O)O)benzyl and $R^{23}$ is 3-(CH$_3$NHC(=O)O)benzyl;

the compound of Formula (IIa) wherein $R^{22}$ is 3-(HOCH$_2$CC)benzyl and $R^{23}$ is 3-bromobenzyl;

the compound of Formula (IIa) wherein $R^{22}$ is 3-acetylbenzyl and $R^{23}$ is 3-bromobenzyl;

the compound of Formula (IIa) wherein $R^{22}$ is 3-acetylbenzyl and $R^{23}$ is 3-acetylbenzyl;

the compound of Formula (IIa) wherein $R^{22}$ is 3-(CH$_3$C(=NOH)benzyl and $R^{23}$ is 3-(CH$_3$C(=NOH))benzyl;

the compound of Formula (IIa) wherein $R^{22}$ is 3-(1-hydroxyethyl)benzyl and $R^{23}$ is 3-bromobenzyl;

the compound of Formula (IIa) wherein $R^{22}$ is 3-(chloromethyl)benzyl and $R^{23}$ is 3-(chloromethyl)benzyl;

the compound of Formula (IIa) wherein $R^{22}$ is 3-(5-tetrazolyl)benzyl and $R^{23}$ is cyclopropylmethyl;

the compound of Formula (IIa) wherein $R^{22}$ is 3-cyanobenzyl and $R^{23}$ is 3-formylbenzyl;

the compound of Formula (IIa) wherein $R^{22}$ is 4-acetoxybenzyl and $R^{23}$ is 4-hydroxybenzyl;

the compound of Formula (IIa) wherein $R^{22}$ is 3-aminocarbonylbenzyl and $R^{23}$ is 3-aminocarbonylbenzyl;

the compound of Formula (IIa) wherein $R^{22}$ is 3-(H$_2$NCOCH$_2$O)benzyl and $R^{23}$ is 3-(H$_2$NCOCH$_2$O)benzyl;

the compound of Formula (IIa) wherein $R^{22}$ is 3-hydroxybenzyl and $R^{23}$ is H;

the compound of Formula (IIa) wherein $R^{22}$ is 3-methylbenzyl and $R^{23}$ is 3-hydroxybenzyl;

the compound of Formula (IIa) wherein $R^{22}$ is 2-naphthylmethyl and $R^{23}$ is 3-hydroxybenzyl;

the compound of Formula (IIa) wherein $R^{22}$ is 3-(H$_2$NNHC(=O)-benzyl and $R^{23}$ is 3-(H$_2$NNHC(=O))-benzyl;

the compound of Formula (IIa) wherein $R^{22}$ is 4-(H$_2$NNHC(=O)-benzyl and $R^{23}$ is 4-(H$_2$NNHC(=O))-benzyl;

the compound of Formula (IIa) wherein $R^{22}$ is 4-hydroxymethylbenzyl and $R^{23}$ is 3-hydroxybenzyl;

the compound of Formula (IIa) wherein $R^{22}$ is 3-(H$_2$NC(=O)NHN=CH)-benzyl and $R^{23}$ is 3-(H$_2$NC(=O)NHN=CH)benzyl;

the compound of Formula (IIa) wherein $R^{22}$ is 3-[(N-methoxy)aminocarbonyl]-benzyl and $R^{23}$ is 3-[(N-methoxy)aminocarbonyl]-benzyl;

the compound of Formula (IIa) wherein $R^{22}$ is 4-[(N-methoxy)aminocarbonyl]-benzyl and $R^{23}$ is 4-[(N-methoxy)aminocarbonyl]-benzyl;

the compound of Formula (IIa) wherein $R^{22}$ is 3-(HOCH$_2$CH(OH)CH$_2$O)benzyl and $R^{23}$ is 3-(HOCH$_2$CH(OH)CH$_2$O)benzyl;

the compound of Formula (IIa) wherein $R^{22}$ is 3-(2-hydroxyethoxy)benzyl and $R^{23}$ is 3-(2hydroxyethoxy)benzyl;

the compound of Formula (IIa) wherein $R^{22}$ is 3-(1,2-dihydroxyethyl)benzyl and $R^{23}$ is 4-(1,2-dihydroxyethyl)benzyl;

the compound of Formula (IIa) wherein $R^{22}$ is 3-aminocarbonylbenzyl and $R^{23}$ is 3-(H$_2$NC(=NH))benzyl;

the compound of Formula (IIa) wherein $R^{22}$ is 4-hydroxybenzyl and $R^{23}$ is 3-formyl-4-hydroxybenzyl;

the compound of Formula (IIa) wherein $R^{22}$ is 3-carbomethoxybenzyl and $R^{23}$ is 3-(N-methylaminocarbonyl)benzyl;

the compound of Formula (IIa) wherein $R^{22}$ is 3-(N-methylaminocarbonyl)benzyl and $R^{23}$ is 3-(N-methylaminocarbonyl)benzyl;

the compound of Formula (IIa) wherein $R^{22}$ is benzyl and $R^{23}$ is 3-hydroxybenzyl;

the compound of Formula (IIa) wherein $R^{22}$ is 2-naphthylmethyl and $R^{23}$ is 4-hydroxymethylbenzyl;

the compound of Formula (IIa) wherein $R^{22}$ is 3-(1,2-dihydroxyethyl)benzyl and $R^{23}$ is 3-(1,2-dihydroxyethyl)benzyl;

the compound of Formula (IIa) wherein $R^{22}$ is 4-(1,2-dihydroxyethyl)benzyl and $R^{23}$ is 4-(1,2-dihydroxyethyl)benzyl;

the compound of Formula (IIa) wherein $R^{22}$ is 3-hydroxymethylbenzyl and $R^{23}$ is 3-(N-methylaminocarbonylbenzyl;

the compound of Formula (IIa) wherein $R^{22}$ is 4-hydroxymethylbenzyl and $R^{23}$ is hydrogen;

the compound of Formula (IIa) wherein $R^{22}$ is 3-(boronic acid)benzyl and $R^{23}$ is 3-(boronic acid)benzyl;

the compound of Formula (IIa) wherein $R^{22}$ is 3-nitrobenzyl and $R^{23}$ is 3-benzyloxybenzyl;

the compound of Formula (IIa) wherein $R^{22}$ is 3-aminobenzyl and $R^{23}$ is 3-hydroxybenzyl;

the compound of Formula (IIa) wherein $R^{22}$ is 3-(N-ethylaminocarbonyl)benzyl and $R^{23}$ is 3-(Nethylaminocarbonyl)benzyl;

the compound of Formula (IIa) wherein $R^{22}$ is 3-carbomethoxybenzyl and $R^{23}$ is 3-(N,N-diethylaminocarbonyl)benzyl;

the compound of Formula (IIa) wherein $R^{22}$ is 3-carbomethoxybenzyl and $R^{23}$ is 3-(N-ethylaminocarbonyl)benzyl;

the compound of Formula (IIa) wherein $R^{22}$ is 6-hydroxy-1-hexyl and $R^{23}$ is hydrogen;

the compound of Formula (IIa) wherein $R^{22}$ is 6-hydroxy-1-hexyl and $R^{23}$ is 6-hydroxy-1-hexyl;

the compound of Formula (IIa) wherein $R^{22}$ is cyclopropylmethyl and $R^{23}$ is 6-hydroxy-1-hexyl;

the compound of Formula (IIa) wherein $R^{22}$ is 5-carboxy-1-pentyl and $R^{23}$ is 5-carboxy-1-pentyl;

the compound of Formula (IIa) wherein $R^{22}$ is 3-iodobenzyl and $R^{23}$ is 3-iodobenzyl;

the compound of Formula (IIa) wherein $R^{22}$ is benzyl and $R^{23}$ is 2-(hydroxymethyl)—cyclopropylmethyl;

the compound of Formula (IIa) wherein $R^{22}$ is 3-(thiomethyl)benzyl and $R^{23}$ is 3-(thiomethyl)benzyl;

the compound of Formula (IIa) wherein $R^{22}$ is 3-(methylsulfonyl)benzyl and $R^{23}$ is 3-(methylsulfonyl)benzyl;

the compound of Formula (IIa) wherein $R^{22}$ is 6-hexenyl and $R^{23}$ is 6-hexenyl;

the compound of Formula (IIa) wherein $R^{22}$ is 6-bromo-5-hydroxy-1-hexyl and $R^{23}$ is 6-bromo-5-hydroxy-1-hexyl;

the compound of Formula (IIa) wherein $R^{22}$ is 5-hydroxy-1-pentyl and $R^{23}$ is 5-hydroxy-1-pentyl;

the compound of Formula (IIa) wherein $R^{22}$ is 3-aminobenzyl and $R^{23}$ is 4-hydroxymethylbenzyl;

the compound of Formula (IIa) wherein $R^{22}$ is 3-($H_2$NC(=O)NH)benzyl and $R^{23}$ is 3-($H_2$NC(=O)NH)benzyl;

the compound of Formula (IIa) wherein $R^{22}$ is 3-(N-methylamino)benzyl and $R^{23}$ is 3-(N-methylamino)benzyl;

the compound of Formula (IIa) wherein $R^{22}$ is cyclopropylmethyl and $R^{23}$ is 3-aminobenzyl;

the compound of Formula (IIa) wherein $R^{22}$ is cyclopropylmethyl and $R^{23}$ is 3-nitrobenzyl;

the compound of Formula (IIa) wherein $R^{22}$ is 3-(N,N-dimethylamo)benzyl and $R^{23}$ is 3-(N,N-dimethylamino)benzyl;

the compound of Formula (IIa) wherein $R^{22}$ is 3-nitrobenzyl and $R^{23}$ is 4-hydroxymethylbenzyl;

the compound of Formula (IIa) wherein $R^{22}$ is 3-aminobenzyl and $R^{23}$ is 3-($CH_3$NHC(=O)NH)benzyl;

the compound of Formula (IIa) wherein $R^{22}$ is 3-($CH_3$NHC(=O)NH)benzyl and $R^{23}$ is 3-($CH_3$NHC(=O)NH)benzyl;

the compound of Formula (IIa) wherein $R^{22}$ is 3-(N-methylamino)benzyl and $R^{23}$ is 4-hydroxymethylbenzyl;

the compound of Formula (IIa) wherein $R^{22}$ is 3-((N,N-dimethylaminoglycyl)amino)benzyl and $R^{23}$ is 3-((N,N-dimethylaminoglycyl)amino)benzyl;

the compound of Formula (IIa) wherein $R^{22}$ is 3-((N-methylaminoglycyl)amino)benzyl and $R^{23}$ is 3-((N-methylaminoglycyl)amino)benzyl;

the compound of Formula (IIa) wherein $R^{22}$ is 3-((N,N-dimethylaminoglycyl)amino)benzyl and $R^{23}$ is 4-hydroxymethylbenzyl;

the compound of Formula (IIa) wherein $R^{22}$ is 3-((N-phenylmethoxycarbonylaminoglycyl)amino)benzyl and $R^{23}$ is 3-((N-Phenylmethoxycarbonylaminoglycyl)amino)benzyl;

the compound of Formula (IIa) wherein $R^{22}$ is 3-(glycylamino)benzyl and $R^{23}$ is 3-(glycylamino)benzyl;

the compound of Formula (IIa) wherein $R^{22}$ is 3-(glycylamino)benzyl and $R^{23}$ is 4-hydroxymethylbenzyl;

the compound of Formula (IIa) wherein $R^{22}$ is 3-((N-phenylmethoxycarbonylamino-L-alanyl)amino)benzyl and $R^{23}$is 3-((N-phenylmethoxycarbonylamino-L-alanyl)amino)benzyl;

the compound of Formula (IIa) wherein $R^{22}$ is 3-((N-phenylmethoxycarbonylamino-L-phenylalanyl)amino)benzyl and $R^{23}$ is 3-((N-Phenylmethoxycarbonylamino-L-phenylalanyl)amino)benzyl;

the compound of Formula (IIa) wherein $R^{22}$ is 3-(L-alanyl)amino)benzyl and $R^{23}$ is 3-(L-alanyl)amino)benzyl;

the compound of Formula (IIa) wherein $R^{22}$ is 3-(L-phenylalanyl)amino)benzyl and $R^{23}$ is 3-(L-phenylalanyl)amino)benzyl;

the compound of Formula (IIa) wherein $R^{22}$ is 5-hydroxy-1-pentyl and $R^{23}$ is hydrogen;

the compound of Formula (IIa) wherein $R^{22}$ is 5-hydroxy-1-pentyl and $R^{23}$ is 2-naphthylmethyl;

the compound of Formula (IIa) wherein $R^{22}$ is 5-hydroxy-1-pentyl and $R^{23}$ is benzyl;

the compound of Formula (IIa) wherein $R^{22}$ is 5-hydroxy-1-pentyl and $R^{23}$ is 4-hydroxymethylbenzyl;

the compound of Formula (IIa) wherein $R^{22}$ is 6-hydroxy-1-hexyl and $R^{23}$ is 2-naphthylmethyl;

the compound of Formula (IIa) wherein $R^{22}$ is 5-hydroxy-1-pentyl and $R^{23}$ is 3-hydroxybenzyl;

the compound of Formula (IIa) wherein $R^{22}$ is 5-hydroxy-1-pentyl and $R^{23}$ is(5-methylsulfonyl)-1-pentyl;

the compound of Formula (IIa) wherein $R^{22}$ is 5-hydroxy-1-pentyl and $R^{23}$ is 5-$(CH_3S(O))$-1-pentyl;

the compound of Formula (IIa) wherein $R^{22}$ is 5-hydroxy-1-pentyl and $R^{23}$ is cyclopropylmethyl;

the compound of Formula (IIa) wherein $R^{22}$ is 5-hydroxy-1-pentyl and $R^{23}$ is 5-methoxy-1-pentyl;

the compound of Formula (IIa) wherein $R^{22}$ is 5-hydroxy-1-pentyl and $R^{23}$ is 3-cyanobenzyl;

the compound of Formula (IIa) wherein $R^{22}$ is 5-hydroxy-1-pentyl and $R^{23}$ is 3-carboethoxybenzyl;

the compound of Formula (IIa) wherein $R^{22}$ is 4-hydroxy-1-hexyl and $R^{23}$ is 4-hydroxy-1-hexyl;

the compound of Formula (IIa) wherein $R^{22}$ is 4-hydroxy-1-hexyl and $R^{23}$ is 2-naphthylmethyl;

the compound of Formula (IIa) wherein $R^{22}$ is 4-oxime-1-hexyl and $R^{23}$ is 4-oxime-1-hexyl;

the compound of Formula (IIa) wherein $R^{22}$ is 5-hydroxy-1-pentyl and $R^{23}$ is 3-hydroxymethylbenzyl;

the compound of Formula (IIa) wherein $R^{22}$ is 6-amino-1-hexyl and $R^{23}$ is 4-hydroxymethylbenzyl;

the compound of Formula (IIa) wherein $R^{22}$ is 3-(N,N-diethylaminocarbonyl)benzyl and $R^{23}$ is 3-(N,N-diethylaminocarbonyl)benzyl;

the compound of Formula (IIa) wherein $R^{22}$ is 3-carbomethoxybenzyl and $R^{23}$ is 3-(N,N-diethylaminocarbonyl)benzyl;

the compound of Formula (IIa) wherein $R^{22}$ is 3-carbomethoxybenzyl and $R^{23}$ is 3-(N-ethylaminocarbonyl)benzyl;

the compound of Formula (IIa) wherein $R^{22}$ is 3-hydroxymethylbenzyl and $R^{23}$ is hydrogen;

the compound of Formula (IIa) wherein $R^{22}$ is 3-hydroxymethylbenzyl and $R^{23}$ is 3-(N,N-diethylaminocarbonyl)benzyl;

the compound of Formula (IIa) wherein $R^{22}$ is 3-hydroxymethylbenzyl and $R^{23}$ is 3-(N-ethylaminocarbonyl)benzyl;

the compound of Formula (IIa) wherein $R^{22}$ is 3-(N-propylaminocarbonyl)benzyl and $R^{23}$ is 3-(N-propylaminocarbonyl)benzyl;

the compound of Formula (IIa) wherein $R^{22}$ is 3-$(HO_2C)$benzyl and $R^{23}$ is 3-(N-isopropylaminocarbonyl)benzyl;

the compound of Formula (IIa) wherein $R^{22}$ is 3-$(HO_2C)$benzyl and $R^{23}$ is 3-(N-propylaminocarbonyl)benzyl;

the compound of Formula (IIa) wherein $R^{22}$ is 3-$(HO_2C)$benzyl and $R^{23}$ is benzyl;

the compound of Formula (IIa) wherein $R^{22}$ is 3-$(HO_2C)$benzyl and $R^{23}$ is cyclopropylmethyl;

the compound of Formula (IIa) wherein $R^{22}$ is 4-hydroxymethylbenzyl and $R^{23}$ is 3-$(HO_2C)$benzyl;

the compound of Formula (IIa) wherein $R^{22}$ is 3-hydroxymethylbenzyl and $R^{23}$ is 3-pyridinylmethyl;

the compound of Formula (IIa) wherein $R^{22}$ is 4-hydroxymethylbenzyl and $R^{23}$ is 3-aminocarbonylbenzyl;

the compound of Formula (IIa) wherein $R^{22}$ is 3-aminobenzyl and $R^{23}$ is 2-naphthylmethyl;

the compound of Formula (IIa) wherein $R^{22}$ is cyclopropylmethyl and $R^{23}$ is 3-aminocarbonylbenzyl;

the compound of Formula (IIa) wherein $R^{22}$ is 3-aminocarbonylbenzyl and $R^{23}$ is hydrogen;

the compound of Formula (IIa) wherein $R^{22}$ is 3-hydroxymethylbenzyl and $R^{23}$ is 3-(N-ethylaminocarbonyl)benzyl;

the compound of Formula (IIa) wherein $R^{22}$ is 3-hydroxymethylbenzyl and $R^{23}$ is 3-(N-methylamino)benzyl;

the compound of Formula (IIa) wherein $R^{22}$ is 3-(N-methylamino)benzyl and $R^{23}$ is 2-naphthylmethyl;

the compound of Formula (IIa) wherein $R^{22}$ is 4-formylbenzyl and $R^{23}$ is 4-hydroxymethylbenzyl;

the compound of Formula (IIa) wherein $R^{22}$ is 3-(1-hydroxy-1-ethyl)benzyl and $R^{23}$ is 3-(1hydroxyethyl)benzyl;

the compound of Formula (IIa) wherein $R^{22}$ is 3-pyridinylmethyl and $R^{23}$ is 4-hydroxymethylbenzyl;

the compound of Formula (IIa) wherein $R^{22}$ is 3-(N-imidazolylmethyl)benzyl and $R^{23}$ is 3-(N-imidazolylmethyl)benzyl;

the compound of Formula (IIa) wherein $R^{22}$ is 3-(2,2-dimethyl-1-propionyl)benzyl and $R^{23}$ is 3-(2,2-dimethyl-1-propionyl)benzyl;

the compound of Formula (IIa) wherein $R^{22}$ is 3-(2,2,2-trifluoro-1-hydroxyethyl)benzyl and $R^{23}$ is 3-(2,2,2-trifluoro-1-hydroxyethyl)benzyl;

the compound of Formula (IIa) wherein $R^{22}$ is 3-(2-imidazolyl-C(=O))benzyl and $R^{23}$ is 3-(2-imidazolyl-C(=O))benzyl;

the compound of Formula (IIa) wherein $R^{22}$ is 3-(3-hydroxy-1-propyn-1-yl)benzyl and $R^{23}$ is 3-(3-hydroxy-1-propyn-1-yl )benzyl;

the compound of Formula (IIa) wherein $R^{22}$ is 3-(2,2,2-trifluoroacetyl)benzyl and $R^{23}$ is 3-(2,2,2-trifluoroacetyl)benzyl;

the compound of Formula (IIa) wherein $R^{22}$ is 3-propionylbenzyl and $R^{23}$ is 3-propionylbenzyl;

the compound of Formula (IIa) wherein $R^{22}$ is 3-(4-pyrazolyl)benzyl and $R^{23}$ is 3-(4-pyrazolyl)benzyl;

the compound of Formula (IIa) wherein $R^{22}$ is 3-$(CH_3CH_2C(=N\text{-}OH))$benzyl and $R^{23}$ is 3-$(CH_3CH_2C(=NOH))$benzyl;

the compound of Formula (IIa) wherein $R^{22}$ is 3-sulfonamidobenzyl and $R^{23}$ is 3-sulfonamidobenzyl;

the compound of Formula (IIa) wherein $R^{22}$ is 3-$(CF_3CH_2C(=N\text{—}OH))$benzyl and $R^{23}$ is 3-$(CF_3CH_2C(=N\text{—}OH))$benzyl;

the compound of Formula (IIa) wherein $R^{22}$ is 4-fluoromethylbenzyl and $R^{23}$ is 4-fluoromethylbenzyl;

the compound of Formula (IIa) wherein $R^{22}$ is 4-(1-hydroxyethyl)benzyl and $R^{23}$ is 4-(1-hydroxyethyl)benzyl;

the compound of Formula (IIa) wherein $R^{22}$ is 3-(5-methyl-1, 2,3-oxadiazolyl)benzyl and $R^{23}$ is 3-(5-methyl-1,2,3-oxadiazolyl)benzyl.

8. A method according to claim 7 wherein the HIV protease inhibitor is([4R-(4a, 5a, 6b, 7b)]hexahydro-5,6-bis(hydroxy)-1,3-bis [(4-hydroxymethyl)phenyl]-methyl)-4, 7-bis(phenylmethy10-2H-1, 3-diazepin-2-one.

9. A method of claim 1 wherein the HIV protease inhibitor is a compound of the Formula (IIaa):

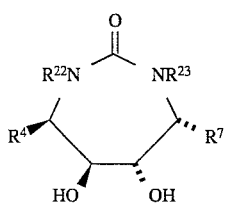

(IIaa)

or a pharmaceutically acceptable salt or prodrug form thereof wherein:

$R^4$ and $R^7$ are independently selected from: benzyl, fluorobenzyl, pyrrolylmethyl, methoxybenzyl, isobutyl, nitrobenzyl or aminobenzyl;

$R^{22}$ and $R^{23}$ are independently selected from:
hydrogen, allyl, methyl, ethyl, propyl, cyclopropylmethyl, n-butyl, i-butyl, $CH_2CH=C(CH_3)_2$, pyridinylmethyl, methallyl, n-pentyl, i-pentyl, hexyl, benzyl, isoprenyl, propargyl, picolinyl, methoxyethyl, cyclohexylmethyl, dimethyl-butyl, ethoxyethyl, methyl-oxazolinylmethyl, naphthylmethyl, methyloxazolinylmethyl, vinyloxyethyl, pentafluorobenzyl, quinolinylmethyl, carboxybenzyl, chloro-thienyl, benzyloxybenzyl, phenylbenzyl, adamantylethyl, cyclopropylmethoxybenzyl, methoxybenzyl, methylbenzyl, ethoxybenzyl, hydroxybenzyl, hydroxymethylbenzyl, aminobenzyl, formylbenzyl, cyanobenzyl, cinnamyl, allyloxybenzyl, fluorobenzyl, difluorobenzyl, chlorobenzyl, chloromethylbenzyl, fluoromethylbenzyl, iodobenzyl, bromobenzyl, cyclobutylmethyl, formaldoximebenzyl, cyclopentylmethyl, nitrobenzyl, $(H_2NC(=O))$-benzyl, carbomethoxybenzyl, carboethoxybenzyl, tetrazolylbenzyl, and dimethylallyl, aminomethylbenzyl, (O-benzyl-formaldoxime)benzyl, (O-methyl-formaldoxime)benzyl, $(CH_3O_2CO)$-benzyl, $(HOCH_2CH_2N=CH)$—benzyl, N-benzylaminocarbonylbenzyl, N-methylaminobenzyl, N-ethylaminobenzyl, N-ethylaminomethylbenzyl, acetylbenzyl, acetoxybenzyl, N-hydroxylaminobenzyl, phenylmethylboronic acid, N-hydroxylaminomethylbenzyl, (hydroxyl)ethylbenzyl, $(CH_3C(=NOH))$-benzyl, $(H_2NNHC(=O))$-benzyl, $(H_2NC(=O)NHN=CH)$-benzyl, $(CH_3ONHC(=O))$-benzyl, $(HONHC(=O))$-benzyl, $(CH_3NHC(=O))$-benzyl, N,N-dimethylaminocarbonylbenzyl, $(HOCH_2CH(OH)CH_2O)$-benzyl, hydroxyethoxybenzyl(oxazolidinyl)-benzyl, (hydroxyl)hexyl, hexenyl, (hydroxy)octyl, (hydroxyl)pentyl, (carboxy)pentyl, (carbomethoxy)pentyl, (methylthio)benzyl, (methylsulfonyl)benzyl, N,N-dimethylaminomethylbenzyl, N-methylaminomethylbenzyl, glycylaminobenzyl, N,N-dimethylglycylaminobenzyl, alanylaminobenzyl, (N-phenylmethoxycarbonyl)alanylaminobenzyl, phenylalanylaminobenzyl, (N-phenylmethoxycarbonyl) phenylalanylaminobenzyl, $(CH_3CH_2NHC(=O))$-benzyl, N,N-diethylaminocarbonylbenzyl, N-ethylaminocarbonylbenzyl, N-propylaminocarbonylbenzyl, N,N-diisopropylaminocarbonylbenzyl, N,N-di-n-propylaminocarbonylbenzyl, (hydroxypropynyl)benzyl, (imidazolyl-C(=O))-benzyl, (pyrazolyl-C(=O))-benzyl, (pyridylmethylaminocarbonyl)benzyl, (oxadiazolidinonyl)benzyl, trifluoroacetylbenzyl, (pyrazolyl)benzyl, $(H_2NSO_2)$-benzyl, dihydroxyethylbenzyl, (MeHNC(=O)NH)-benzyl, $(H_2NC(=O)NH)$-benzyl, (HC(=O)NH)-benzyl, methanesulfonylpentyl, methoxypentyl, N-formyl-N-methylaminobenzyl, acetylaminobenzyl, propionylbenzyl, butyrylbenzyl, $(CH_3CH_2C(=NOH))$-benzyl, (trifluorohydroxyethyl)benzyl, $(CF_3C(=NOH))$-benzyl, (N-methylglycyl)aminobenzyl, ((4-morpholino)ethyl )aminocarbonylbenzyl, (N,N-dimethylaminoethyl )aminocarbonylbenzyl, (N,N-diethylaminoethyl )aminocarbonylbenzyl, (4-methylpiperazin-1-ylethyl)aminocarbonylbenzyl, (benzyl—NHC(=O)O)benzyl, $(CH_3NHC(=O)O)$benzyl, $(NH_2C(=O)CH_2O)$benzyl, $(NH_2C(=NH))$benzyl, ((N-phenylmethoxycarbonyl)glycylamino )benzyl, (imidazolylmethyl)benzyl, $((CH_3)_3C—C(=O))$benzyl, (N-methyl-N-ethylaminoethyl)aminocarbonylbenzyl, (pyrrolidinylethyl)aminocarbonylbenzyl, (piperidinylethyl)aminocarbonylbenzyl.

10. A method according to claim 9 wherein a compound of Formula (IIaa) is selected from the group consisting of:

the compound of Formula (IIaa) wherein $R^4$ and $R^7$ are isobutyl, $R^{22}$ and $R^{23}$ are cyclopropylmethyl;

the compound of Formula (IIaa) wherein $R^4$ and $R^7$ are isobutyl, $R^{22}$ and $R^{23}$ are allyl;

the compound of Formula (IIaa) wherein $R^4$ is 4-nitrobenzyl, $R^7$ is 2-nitrobenzyl, $R^{22}$ and $R^{23}$ are cyclopropylmethyl;

the compound of Formula (IIaa) wherein $R^4$ and $R^7$ are 4-nitrobenzyl, $R^{22}$ and $R^{23}$ are cyclopropylmethyl;

the compound of Formula (IIaa) wherein $R^4$ is 4-nitrobenzyl, $R^7$ is 2-nitrobenzyl, $R^{22}$ and $R^{23}$ are n-butyl;

the compound of Formula (IIaa) wherein $R^4$ is 4-aminobenzyl, $R^7$ is 2-aminobenzyl, $R^{22}$ $R^{23}$ are cyclopropylmethyl;

the compound of Formula (IIaa) wherein $R^4$ and $R^7$ are 4-fluorobenzyl, $R^{22}$ and $R^{23}$ are 3-hydroxybenzyl;

the compound of Formula (IIaa) wherein $R^4$ and $R^7$ are 4-fluorobenzyl, $R^{22}$ and $R^{23}$ are cyclopropylmethyl;

the compound of Formula (IIaa) wherein $R^4$ and $R^7$ are 4-fluorobenzyl, $R^{22}$ and $R^{23}$ are 4-hydroxymethylbenzyl;

the compound of Formula (IIaa) wherein $R^4$ and $R^7$ are 4-fluorobenzyl, $R^{22}$ and $R^{23}$ are 3-aminocarbonylbenzyl;

the compound of Formula (IIaa) wherein $R^4$ and $R^7$ are 4-fluorobenzyl, $R^{22}$ and $R^{23}$ are 3-acetylbenzyl;

the compound of Formula (IIaa) wherein $R^4$ and $R^7$ are 4-fluorobenzyl, $R^{22}$ and $R^{23}$ are 3-butyrylbenzyl;

the compound of Formula (IIaa) wherein $R^4$ and $R^7$ are 4-fluorobenzyl, $R^{22}$ and $R^{23}$ are 3-hydroxymethylbenzyl;

the compound of Formula (IIaa) wherein $R^4$ and $R^7$ are 4-fluorobenzyl, $R^{22}$ and $R^{23}$ are 3-$(CH_3C(=N—OH))$benzyl;

the compound of Formula (IIaa) wherein $R^4$ and $R^7$ are 3-methoxybenzyl, $R^{22}$ and $R^{23}$ are benzyl.

11. A method according to claim 5 wherein the HIV reverse transcriptase inhibitor is AZT.

12. The method according to claim 5, wherein the reverse transcriptase inhibitor is ddI.

13. The method according to claim 5, wherein the reverse transcriptase inhibitor is ddC.

14. The method according to claim 5, wherein the reverse transcriptase inhibitor is d4T.

15. The method according to claim 5, wherein the reverse transcriptase inhibitor is 3TC.

16. The method according to claim 7, wherein the reverse transcriptase inhibitor is AZT.

17. The method according to claim 7, wherein the reverse transcriptase inhibitor is ddI.

18. The method according to claim 7, wherein the reverse transcriptase inhibitor is ddC.

19. The method according to claim 7, wherein the reverse transcriptase Inhibitor ms d4T.

20. The method according to claim 7, wherein the reverse transcriptase inhibitor is 3TC.

21. The method according to claim 7, wherein the HIV protease inhibitor is [4R-(4a, 5a, 6b, 7b)]-1,2-bis[(3-aminophenyl)methyl]hexahydro-5, 6-dihydroxy-4,7-bis(phenylmethyl)-2H-1,3-diazepin-2-one.

22. The method according to claim 21, wherein the reverse transcriptase inhibitor is AZT.

23. The method according to claim 21, wherein the reverse transcriptase inhibitor is ddI.

24. The method according to claim 21, wherein the reverse transcriptase inhibitor is ddC.

25. The method according to claim 21, wherein the reverse transcriptase inhibitor is d4T.

26. The method according to claim 21, wherein the reverse transcriptase inhibitor is 3TC.

* * * * *